US008252979B2

(12) United States Patent
Gupta et al.

(10) Patent No.: US 8,252,979 B2
(45) Date of Patent: Aug. 28, 2012

(54) MANIPULATION OF AMMONIUM TRANSPORTERS (AMTS) TO IMPROVE NITROGEN USE EFFICIENCY IN HIGHER PLANTS

(75) Inventors: Rajeev Gupta, Johnston, IA (US); Juan Liu, Johnston, IA (US); Kanwarpal S. Dhugga, Johnston, IA (US); Carl R. Simmons, Des Moines, IA (US)

(73) Assignee: Pioneer Hi Bred International Inc., Johnston, IA (US)

( * ) Notice: Subject to any disclaimer, the term of this patent is extended or adjusted under 35 U.S.C. 154(b) by 0 days.

(21) Appl. No.: 13/043,109

(22) Filed: Mar. 8, 2011

(65) Prior Publication Data
US 2011/0225675 A1 Sep. 15, 2011

Related U.S. Application Data

(63) Continuation of application No. 12/045,098, filed on Mar. 10, 2008, now abandoned.

(60) Provisional application No. 60/893,901, filed on Mar. 9, 2007.

(51) Int. Cl.
*A01H 1/00* (2006.01)
*C07H 21/04* (2006.01)
*C07K 14/415* (2006.01)
*C12N 15/00* (2006.01)

(52) U.S. Cl. ......... 800/295; 435/6.1; 435/468; 435/419; 435/320.1; 435/69.1; 530/370; 536/23.6; 800/278

(58) Field of Classification Search .................. 435/6.1, 435/69.1, 468, 419, 320.1; 530/370; 536/23.6; 800/278, 295
See application file for complete search history.

(56) References Cited

U.S. PATENT DOCUMENTS

| 7,368,634 | B2 | 5/2008 | Allen et al. | |
|---|---|---|---|---|
| 7,589,257 | B2 | 9/2009 | Hershey et al. | |
| 2004/0034888 | A1 * | 2/2004 | Liu et al. | 800/289 |
| 2004/0214272 | A1 | 10/2004 | La Rosa et al. | |

OTHER PUBLICATIONS

Canabes, G., et al.; "Ammonium transport and CitAMT1 expression are regulated by N in Citrus plants"; Planta (2009) 229:331-342; Springer-Verlag; Berlin/Heidelberg, Germany.
Couturier, J., et al.; "The expanded family of ammonium transporters in the perennial poplar plant", New Phytologist (2007) 174:137-150; John Wiley & Sons, Inc.; Hoboken, NJ, US.
Engineer, C., et al.; "Reciprocal Leaf and Root Expression of AtAmt1.1 and Root Architectural Changes in Response to Nitrogen Starvation"; Plant Physiology (Jan. 2007) 143:236-250; American Society of Plant Biologists; Rockville, MD, US.
Andrade S.L.A. and Einsle, O.; "The Amt/Mep/Rh family of ammonium transport proteins (Review)"; Molecular Membrane Biology (Sep.-Dec. 2007) 24(5-6):357-365; Informa UK Ltd.; UK.
Kang, L-K, et al.; "Influences of nitrogen deficiency on the transcript levels of ammonium transporter, nitrate transporter and glutamine synthetase genes in *Isochrysis galbana* (Isochrysidales, Haptophyta)"; Phycologia (2007) 46 (5):521-533; International Phycological Society; Lawrence, KS, US.
Loque, D., et al.; "A cytosolic trans-activation domain essential for ammonium uptake"; Nature (Mar. 2007) 446:195-198; Nature Publishing Group; London, UK.
Ludewig, U., et al.; "Molecular mechanisms of ammonium transport and accumulation in plants"; FEBS Letters (2007) 581:2301-2308; Federation of European Biochemical Societies; Elsevier; Amsterdam, The Netherlands.
Merigout, P., et al.; "Physiological and Transcriptomic Aspects of Urea Uptake and Assimilation in *Arabidopsis* Plants"; Plant Physiology (Jul. 2008) 147:1225-1238; American Society of Plant Biologists; Rockville, MD, US.
Rogato, A., et al.; "Tissue-specific down-regulation of LjAMT1;1 comprises nodule function and enhances nodulation in *Lotus japonicus*"; Plant Mol Biol (2008) 68:585-595; Springer; The Netherlands.
Yao, S-G. et al.; "Promoter analysis of OsAMT1 ;2 and OsAMT1; 3 implies their distinct roles in nitrogen utilization in rice"; Breeding Science (2008)58:201-207; Japanese Society of Breeding; Japan.
Yuan, L., et al.; "The Organization of High-Affinity Ammonium Uptake in *Arabidopsis* Roots Depends on the Spatial Arrangement and Biochemical Properties of AMT1-Type Transporters"; The Plant Cell (Aug. 2007) 19:2636-2652; American Society of Plant Biologists; Rockville, MD, US.
Yuan, L., et al.; "AtAMT1;4, a Pollen-Specific High-Affinity Ammonium Transporter of the Plasma Membrane in *Arabidposis*"; Plant Cell Physiology (2009) 50(1):13-25; Oxford University Press; Oxford, UK.
Yuan, L., et al.; "Nitrogen-Dependent Posttranscriptional Regulation of the Ammonium Transporter AtAMT1;1"; Plant Physiology (Feb. 2007) 143:732-744; American Society of Plant Biologists; Rockville, MD US.
Zhao, X.Q., et al.; "Enhancemtn of NH+4 Uptake by NO-3 in Relation to Expression of Nitrate-Induced Genes in Rice (*Oryza sativa*) Roots"; Pedosphere (2008) 18(1):86-91; Elsevier; Amsterdam, The Netherlands.
Duan, Y.H., et al.; "Mechanisms of Enhanced Rice Growth and Uptake by Nitrate"; Pedosphere (2007) 17(6):697-705; Elsevier; Amsterdam, The Netherlands.

* cited by examiner

*Primary Examiner* — Phuong T Bui
(74) *Attorney, Agent, or Firm* — Pioneer Hi-Bred Int'l Inc.

(57) ABSTRACT

The present invention provides polynucleotides and related polypeptides of the protein AMT. The invention provides genomic sequence for the AMT gene. AMT is responsible for controlling nitrogen utilization efficiency in plants.

8 Claims, 6 Drawing Sheets

| Seq id | Root | Mesocotyl/Coleoptile | Leaf | Stalk | Apical Meristem | Immature Ear | Ovary/R1-Kernel | Embryo | Endosperm | Pericarp | Silk | Tassel Spikelet | Pollen |
|---|---|---|---|---|---|---|---|---|---|---|---|---|---|
| ZmAMT_01_ins | 55.8 | 0 | 36.2 | 14.6 | 0 | 0.9 | 0 | 0 | 0 | 0 | 33 | 40.5 | 0 |
| ZmAMT_02_ins | 10.6 | 0 | 17.6 | 0.8 | 0 | 0 | 0 | 0 | 0 | 0 | 0 | 0.2 | 0 |
| ZmAMT_04_ins | 55.1 | 0 | 0.7 | 0 | | 0 | 0 | 0 | 0 | 0 | 0 | 0 | |
| ZmAMT_05_ins | 0.3 | 0 | 0.4 | 2.4 | | 0 | 0 | 0 | 0 | 3.7 | 0 | 0 | 0 |
| ZmAMT_06_ins | | | | | | | | | | | | | |
| ZmAMT_07_ins | 70 | 0 | 11.2 | 15.7 | 0 | 0.8 | 0 | 0 | 0 | 0 | 84 | 42.5 | 0 |

```
                              151                                                 200
         AtAMT1.2       (151) GTCGACAACACGTATCTCCTCTTCTCCGCCTACCTTGTCTTTGCCATGCA
           AtAMT1       (121) ATAGACAACACTTACCTTCTCTTCTCCGCCTACCTTGTCTTCTCTATGCA
         AtAMT1.3       (133) ATAGACAACACCTACCTCCTCTTCTCTGCCTACCTTGTCTTCGCCATGCA
AtAMT3(At3g24290)       (133) ATAGACAACACGTACCTCCTCTTCTCTGCCTATCTTGTCTTTGCGATGCA
AtAMT4(At4g28700)       (148) ATCGACAACACTTACCTTCTCTTCTCTGCTTACCTCGTTTTCGCGATGCA
        Consensus       (151) ATAGACAACAC TACCTCCTCTTCTCTGCCTACCTTGTCTTCGC ATGCA
                              201                                                 250
         AtAMT1.2       (201) GCTCGGTTTCGCTATGCTTTGTGCTGGATCAGTCCGAGCCAAGAACACTA
           AtAMT1       (171) GCTTGGCTTCGCTATGCTCTGTGCCGGTTCCGTGAGAGCCAAGAATACTA
         AtAMT1.3       (183) GCTCGGCTTCGCTATGCTTTGTGCTGGTTCTGTTAGAGCCAAGAATACGA
AtAMT3(At3g24290)       (183) GCTCGGCTTCGCTATGCTTTGTGCTGGCTCCGTTAGAGCTAAGAACACGA
AtAMT4(At4g28700)       (198) GCTCGGTTTCGCCATGCTCTGTGCCGGATCCGTACGTGCAAAAAACACGA
        Consensus       (201) GCTCGGCTTCGCTATGCTTTGTGCTGG TCCGT AGAGCCAAGAACACGA
                              251                                                 300
         AtAMT1.2       (251) TGAACATCATGCTTACCAATGTCCTTGATGCTGCCGCTGGAGCCATCTCT
           AtAMT1       (221) TGAACATCATGCTTACCAACGTCCTTGACGCTGCAGCCGGTGGTCTCTTC
         AtAMT1.3       (233) TGAACATCATGCTTACCAATGTCCTTGACGCTGCAGCCGGAGGACTCTTC
AtAMT3(At3g24290)       (233) TGAACATCATGCTCACTAATGTCCTTGATGCTGCAGCCGGAGGACTCTTC
AtAMT4(At4g28700)       (248) TGAACATTATGCTCACGAACGTCATCGACGCTGCAGCCGGAGGTCTCTTC
        Consensus       (251) TGAACATCATGCTTACCAATGTCCTTGACGCTGCAGCCGGAGG CTCTTC
                              301                                                 350
         AtAMT1.2       (301) TACTACCTCTTCGGATTCGCATTCGCCTTTGGTACACCTTCCAACGGATT
           AtAMT1       (271) TATTATCTGTTTGGCTACGCCTTTGCCTTTGGATCTCCGTCCAATGGTTT
         AtAMT1.3       (283) TACTATCTCTTTGGTTACGCCTTTGCCTTTGGAGGATCCTCCGAAGGGTT
AtAMT3(At3g24290)       (283) TACTACCTCTTTGGTTATGCATTTGCCTTTGGTGAATCCTCCGATGGATT
AtAMT4(At4g28700)       (298) TATTATCTCTTCGGTTTCGCTTTTGCTTTTGGATCTCCTTCTAATGGATT
        Consensus       (301) TACTATCTCTTTGGTTACGC TTTGCCTTTGGA CACC TCCAATGGATT
```

B

AtAMT2 acttggtggaataatgacagggttgt
ttgcacaccctgatctctgcgttttg
gtacttcctctcccagcgaccagagg
agctttctacggtggcaatggcggcg
gaataatgacagggttgtttgcacac
cctgatctctgcgttttggtacttcc
tctcccagcgaccagaggagctttct
acggtggcaatggcggcaaacagctt
ttgaaacagttggctggagctgcctt
cattgccgtctggaatgtggtgtcga
ctactatcattctactcgctattagg
gtgttcataccattgagaatggctga
ggaagag

Figure 4

```
ZmAMT_01_orf  (243) GCTCTTCTACTACCTCTTCGGCTTCGCCTTCGCCTTCGGCACGCCCTCCA
ZmAMT_05_orf  (243) GCTCTTCTACTACCTATTCGGCTTCGCCTTCGCCTACGGCACCCCGTCCA
   Consensus  (243) GCTCTTCTACTACCT TTCGGCTTCGCCTTCGCCT CGGCAC CC TCCA
                    293                                              342
ZmAMT_01_orf  (293) ACGGCTTCATCGGCAAGCAGTTCTTCGGGCTCAAGCACCTGCCCAGGACC
ZmAMT_05_orf  (293) ACGGCTTCATCGGCAAGCACTTCTTCGGCCTCAAGCGCCTGCCCAAGACC
   Consensus  (293) ACGGCTTCATCGGCAAGCA TTCTTCGG CTCAAGC CCTGCCCA GACC
                    343                                              392
ZmAMT_01_orf  (343) GGCTTCGACTACGACTTCTTCCTCTACCAGTGGGCCTTCGCCATCGCCGC
ZmAMT_05_orf  (343) GGCTTCGACTACGACTTCTTCCTATACCAGTGGGCCTTCGCCATCGCCGC
   Consensus  (343) GGCTTCGACTACGACTTCTTCCT TACCAGTGGGCCTTCGCCATCGCCGC
                    393                                              442
ZmAMT_01_orf  (393) CGCGGGCATCACGTCGGGCTCCATCGCCGAGCGGACCCAGTTCGTCGCCT
ZmAMT_05_orf  (393) CGCCGGCATCACGTCCGGCTCCATCGCCGAGAGCACCCAGTTCGTCGCCT
   Consensus  (393) CGC GGCATCACGTC GGCTCCATCGCCGAG G ACCCAGTTCGTCGCCT
                    443                                              492
ZmAMT_01_orf  (443) ACCTCATCTACTCCGCGTTCCTGACGGGGTTCGTCTACCCCGTGGTGTCG
ZmAMT_05_orf  (443) ACCTCATCTACTCCGCCTTCCTCACCGGCTTCGTGTACCCCGTGGCGTCC
   Consensus  (443) ACCTCATCTACTCCGC TTCCT AC GG TTCGT TACCCCGTGG GTC
                    493        507
ZmAMT_01_orf  (493) CACTGGTTCTGGTCC
ZmAMT_05_orf  (493) CACTGGGTCTGGTCC
   Consensus  (493) CACTGG TCTGGTCC 241                                              290
ZmAMT_04_orf  (241) CTCTTCTACTACCTATTCGGCTTCGCCTTCGCGTACGGGACCCCGTCCAA
ZmAMT_04_orf  (291) CGGCTTCATCGGCAAGCACTTCTTCGGCCTCAAGCGGCTTCCCCAGGTCG
ZmAMT_04_orf  (341) GGTTCGACTACGACTTCTTCCTCTTCCAGTGGGCTTTCGCCATCGCCGCC
ZmAMT_04_orf  (391) GCCGGGATACGTCCGGCTCCATCGCCGAGCGCACGCAGTTCGTGGCGTA
ZmAMT_04_orf  (441) CCTCATCTACTCCGCCTTCCTCACCGGCTTCGTGTACCCGGTGGTGTCCC
ZmAMT_04_orf  (491) ACTGGGTCTGGTCCGCCGACGGCTGGGCCTCGCCGTCACGGACGTCGGGG
ZmAMT_04_orf  (541) AAGCTCCTCTTCGGCTCCGGCATCATCGACTTCGCCGGGTCCAGCGTTGT
ZmAMT_03_orf    (1) ------------------------------------------CGTTGT
   Consensus  (541)                                           CGTTGT
                    591                                              638
ZmAMT_04_orf  (591) CCACATGGTGGGCGGAATCGCCGGCCTCTGGGGCGCCCTCATCGAGGG
ZmAMT_03_orf    (7) CCACATGGTGGGCGGAATCGCCGGCCTCTGGGGCGCCCTCATCGAGGG
   Consensus  (591) CCACATGGTGGGCGGAATCGCCGGCCTCTGGGGCGCCCTCATCGAGGG
```

Figure 5a

```
ZmAMT_07_orf   (49)  GAGTGGCTGAACAAGGGCGACAACGCGTGGCAGCTGACGGCGGCGACGCT
ZmAMT_02_orf   (46)  GACTGGCTGAACAAGGGCGACAATGCGTGGCAGATGACGTCCGCGACGCT
ZmAMT_06_orf   (61)  GAGTGGCTGAACAAGGGCGACAACGCGTGGCAGCTGACGGCGGCGACGCT
   Consensus   (65)  GAGTGGCTGAACAAGGGCGACAACGCGTGGCAGCTGACGGCGGCGACGCT
                     115                                              164
ZmAMT_07_orf   (99)  GGTGGGCATCCAGTCGATGCCGGGGCTGGTGGTGCTGTACGGCAGCATCG
ZmAMT_02_orf   (96)  GGTGGGCCTGCAGAGCATGCCCGGGCTGGTGATCCTGTACGGCAGCATCG
ZmAMT_06_orf  (111)  GGTGGGGCTGCAGAGCTTCCCGGGTCTGGTGGTCCTGTACGGCGGCGTGG
   Consensus  (115)  GGTGGGCCTGCAGAGCATGCCGGGGCTGGTGGTCCTGTACGGCAGCATCG
                     165                                              214
ZmAMT_07_orf  (149)  TGAAGAAGAAGTGGGCGGTGAACTCGGCGTTCATGGCGCTGTACGCCTAC
ZmAMT_02_orf  (146)  TGAAGAAGAAGTGGGCCATCAACTCGGCGTTCATGGCGCTGTACGCCTTC
ZmAMT_06_orf  (161)  TGAAGAAGAAGTGGGCCGTGAACTCGGCCTTCATGGCGCTGTACGCGTTC
   Consensus  (165)  TGAAGAAGAAGTGGGCCGTGAACTCGGCGTTCATGGCGCTGTACGCCTTC
                     215                                              264
ZmAMT_07_orf  (199)  GCGTCGTCGCTGCTGGTGTGGGTGCTGGCGGGGTTCCGCATGGCGTTCGG
ZmAMT_02_orf  (196)  GCCGCCGTCTGGCTCTGCTGGGTGGTGTGGGCCTACAACATGTCGTTCGG
ZmAMT_06_orf  (211)  GCGGCGGTGTGGATCTGCTGGGTGACCTGGGCCTACAACATGTCCTTCGG
   Consensus  (215)  GCGGCGGTGTGGCTCTGCTGGGTG TGTGGGCCTACAACATGTCGTTCGG
                     265                                              314
ZmAMT_07_orf  (249)  GGAGCGGCTGCTCCCGTTCTGGGGCAAGGCCGGGGTGGCGCTCTCCCAGG
ZmAMT_02_orf  (246)  CGACCGGCTGCTGCCCTTCTGGGGCAAGGCGAGGCCGGCGCTCGGGCAGC
ZmAMT_06_orf  (261)  CGACAGGCTGCTGCCGCTGTGGGGCAAGGCGCGGCCGGCGCTGAGCCAGG
   Consensus  (265)  CGACCGGCTGCTGCCGTTCTGGGGCAAGGCG GGCCGGCGCTC GCCAGG
                     315                                              364
ZmAMT_07_orf  (299)  GCTACCTGGTCCGGCGCGCCTCGCTCTCGGCGACCGC---GCA-------
ZmAMT_02_orf  (296)  GCTTCCTGGTGGCGCAGTCCCAGCTCACGGCCACCGCCGTGCGGTACCGC
ZmAMT_06_orf  (311)  GCGGGCTGGTGGGGCAGGCCGGCCTCCCCGCCACGGCGCACCACTTCGCC
   Consensus  (315)  GCT CCTGGTGGGGCAGGCC  GCTC CGGCCACCGC   GCA T C  C
                     365                                              414
ZmAMT_07_orf  (339)  --CGGGGCC----ACGCCCCG--CACCGAGCCCCTGTACCCGGAGGCGAC
ZmAMT_02_orf  (346)  GACGGGTCGCTCGAGGCGGAGATGCTCCACCCCTTCTACCCGGCCGCCAC
ZmAMT_06_orf  (361)  AGCGGCGCCCTGGAGACCCCGGCCGCGGAGCCGCTGTACCCGATGGCCAC
   Consensus  (365)     CGGGGCCCT GAGGCCCCG  C CCGAGCCCCTGTACCCGG GGCCAC
                     415                                              464
ZmAMT_07_orf  (381)  GCTGGTGCTGTTCCAGTTCGAGTTCGCCGCCATCACGCTGGTGCTCCTGG
ZmAMT_02_orf  (396)  CATGGTGTACTTCCAGTGCGTGTTCGCCAGCATCACCGTCATCATCCTCG
ZmAMT_06_orf  (411)  GGTGGTGTACTTCCAGTGCGTGTTCGCGGCCATCACCCTGGTGCTGGTCG
   Consensus  (415)  G TGGTGTACTTCCAGTGCGTGTTCGCCGCCATCACCCTGGTGCTCCTCG
```

Figure 5b

MANIPULATION OF AMMONIUM TRANSPORTERS (AMTS) TO IMPROVE NITROGEN USE EFFICIENCY IN HIGHER PLANTS

CROSS REFERENCE

This utility application is a continuation of U.S. patent application Ser. No. 12/045,098 filed Mar. 10, 2008 now abandoned which claims the benefit of U.S. Provisional Application No. 60/893,901, filed Mar. 9, 2007, both of which are incorporated herein by reference.

FIELD OF THE INVENTION

The invention relates generally to the field of molecular biology.

BACKGROUND OF THE INVENTION

Nitrogen (N) is the most abundant inorganic nutrient taken up from the soil by plants for growth and development. Maize roots absorb most of the N from the soil in the form of nitrate, the majority of which is transported to the leaf for reduction and assimilation. Nitrate is reduced to nitrite by nitrate reductase (NR) in the cytosol and then nitrite is transported into chloroplast where it is reduced by nitrite reductase (NiR) to ammonium. Ammonium is assimilated into glutamine by the glutamine synthase-glutamate synthase system (Crawford and Glass, (1998) *Trends in Plant Science* 3:389-395.). Also, it has long been known that significant amounts of N are lost from the plant aerial parts by volatilization (Glyan'ko, et al., (1980) *Agrokhimiya* 8:19-26; Hooker, et al., (1980) *Agronomy Journal* 72(5):789-792; Silva, et al., (1981) *Crop Science* 21(6): 913-916; Stutte, et al., (1981) *Crop Science* 21(4):596-600; Foster, et al., (1986) *Annals of Botany* 57(3): 305-307; Parton, et al., (1988) *Agronomy Journal* 80(3):419-425; Kamiji, et al., (1989) *Japanese Journal of Crop Science* 58(1):140-142; Morgan, et al., (1989) *Crop Science* 29(3): 726-731; O'Deen, (1989) *Agronomy Journal* 81(6):980-985; Guindo, et al., (1994) *Arkansas Farm Research* 43(1):12-13; Heckathorn, et al., (1995) *Oecologia* 101(3):361-365; Cabezas, et al., (1997) *Revista Brasileira de Ciencia do Solo* 21(3): 481-487). Experimental evidence supports the loss of N through ammonium and not through N oxides (Hooker, et al., 1980). Treatment with chemicals that inhibit glutamine or glutamate synthase activities led to increased loss of ammonium through volatilization (Foster, et al., 1986). Loss of N is not only limited to C-3 species as C-4 plants have also been reported to lose N through volatilization (Heckathorn, et al., 1995).

Manipulation of AMTs can be utilized to improve NUE by causing increased dry matter, thereby contributing to an increase in plant yield. Two of the ways to improved dry matter accumulation are: 1) reduce N loss through volatilization and 2) reduce N content of the plant so that more dry matter can be accumulated in the form of low-energy constituents, e.g., starch or cellulose.

For ammonium to be lost from the leaf, it must first pass through a facilitated channel since it is highly hydrophilic. Ammonium transporters (AMTs) were originally discovered as ammonium transporters but some recent studies have shown that at least in some cases AMTs can act as gas channels (Soupene, et al., (2002) *Proc Natl Acad Sci USA* 99:3926-3931; Kustu and Inwood, (2006) *Transfus Clin Biol* 13:103-110). An amtB knock-out mutant of *Salmonella* grows better on poor N source, apparently because it can sequester more N by keeping it from leaking back out (Soupene, et al., 2002). This application details an invention which is used to manipulate AMTs in higher plants to improve NUE. The inventors identified chloroplast-specific and/or leaf-preferred AMT(s) and knocked them out/down to minimize the loss of ammonium, which resulting in better N assimilation/NUE. In addition, work was not limited only to the chloroplast-localized AMTs but will also down-regulation of the AMTs that are localized to other organelles/membranes.

SUMMARY OF THE INVENTION

The present invention provides polynucleotides, related polypeptides and all conservatively modified variants of the present AMT sequences. The invention provides sequences for the AMT genes. Six *Arabidopsis*, 7 maize, 17 rice, and 11 soybean AMT genes were identified. Table 1 lists these genes and their seq id numbers.

TABLE 1

| SEQUENCE ID NUMBER | IDENTITY |
|---|---|
| SEQ ID NOS: 1 | AtAMT 1 polynucleotide |
| SEQ ID NOS: 2 | AtAMT 1 polypeptide |
| SEQ ID NO: 3 | AtAMT 1; 2 polynucleotide |
| SEQ ID NO: 4 | AtAMT 1; 2 polypeptide |
| SEQ ID NO: 5 | AtAMT 1; 3 polynucleotide |
| SEQ ID NO: 6 | AtAMT 1; 3 polypeptide |
| SEQ ID NO: 7 | AtAMT 2 polynucleotide |
| SEQ ID NO: 8 | AtAMT 2 polypeptide |
| SEQ ID NO: 9 | AtAMT 3 polynucleotide |
| SEQ ID NO: 10 | AtAMT 3 polypeptide |
| SEQ ID NO: 11 | AtAMT 4 polynucleotide |
| SEQ ID NO: 12 | AtAMT 4 polypeptide |
| SEQ ID NO: 13 | ZmAMT 1 polynucleotide |
| SEQ ID NO: 14 | ZmAMT 1 polypeptide |
| SEQ ID NO: 15 | ZmAMT 2 polynucleotide |
| SEQ ID NO: 16 | ZmAMT 2 polypeptide |
| SEQ ID NO: 17 | ZmAMT 3 polynucleotide |
| SEQ ID NO: 18 | ZmAMT 3 polypeptide |
| SEQ ID NO: 19 | ZmAMT 4 polynucleotide |
| SEQ ID NO: 20 | ZmAMT 4 polypeptide |
| SEQ ID NO: 21 | ZmAMT 5 polynucleotide |
| SEQ ID NO: 22 | ZmAMT 5 polypeptide |
| SEQ ID NO: 23 | ZmAMT 6 polynucleotide |
| SEQ ID NO: 24 | ZmAMT 6 polypeptide |
| SEQ ID NO: 25 | ZmAMT 7 polynucleotide |
| SEQ ID NO: 26 | ZmAMT 7 polypeptide |
| SEQ ID NO: 27 | OsAMT 1 polynucleotide |
| SEQ ID NO: 28 | OsAMT 1 polypeptide |
| SEQ ID NO: 29 | OsAMT 2 polynucleotide |
| SEQ ID NO: 30 | OsAMT 2 polypeptide |
| SEQ ID NO: 31 | OsAMT 3 polynucleotide |
| SEQ ID NO: 32 | OsAMT 3 polypeptide |
| SEQ ID NO: 33 | OsAMT 4 polynucleotide |
| SEQ ID NO: 34 | OsAMT 4 polypeptide |
| SEQ ID NO: 35 | OsAMT 5 polynucleotide |
| SEQ ID NO: 36 | OsAMT 5 polypeptide |
| SEQ ID NO: 37 | OsAMT 6 polynucleotide |
| SEQ ID NO: 38 | OsAMT 6 polypeptide |
| SEQ ID NO: 39 | OsAMT 7 polynucleotide |
| SEQ ID NO: 40 | OsAMT 7 polypeptide |
| SEQ ID NO: 41 | OsAMT 8 polynucleotide |
| SEQ ID NO: 42 | OsAMT 8 polypeptide |
| SEQ ID NO: 43 | OsAMT 9 polynucleotide |
| SEQ ID NO: 44 | OsAMT 9 polypeptide |
| SEQ ID NO: 45 | OsAMT 10 polynucleotide |
| SEQ ID NO: 46 | OsAMT 10 polypeptide |
| SEQ ID NO: 47 | OsAMT 11 polynucleotide |
| SEQ ID NO: 48 | OsAMT 11 polypeptide |
| SEQ ID NO: 49 | OsAMT 12 polynucleotide |
| SEQ ID NO: 50 | OsAMT 12 polypeptide |
| SEQ ID NO: 51 | OsAMT 13 polynucleotide |
| SEQ ID NO: 52 | OsAMT 13 polypeptide |
| SEQ ID NO: 53 | OsAMT 14 polynucleotide |

TABLE 1-continued

| SEQUENCE ID NUMBER | IDENTITY |
|---|---|
| SEQ ID NO: 54 | OsAMT 14 polypeptide |
| SEQ ID NO: 55 | OsAMT 15 polynucleotide |
| SEQ ID NO: 56 | OsAMT 15 polypeptide |
| SEQ ID NO: 57 | OsAMT 16 polynucleotide |
| SEQ ID NO: 58 | OsAMT 16 polypeptide |
| SEQ ID NO: 59 | OsAMT 17 polynucleotide |
| SEQ ID NO: 60 | OsAMT 17 polynucleotide |
| SEQ ID NO: 61 | GmAMT 1 polynucleotide |
| SEQ ID NO: 62 | GmAMT 1 polypeptide |
| SEQ ID NO: 63 | GmAMT 2 polynucleotide |
| SEQ ID NO: 64 | GmAMT 2 polypeptide |
| SEQ ID NO: 65 | GmAMT 3 polynucleotide |
| SEQ ID NO: 66 | GmAMT 3 polypeptide |
| SEQ ID NO: 67 | GmAMT 4 polynucleotide |
| SEQ ID NO: 68 | GmAMT 4 polypeptide |
| SEQ ID NO: 69 | GmAMT 5 polynucleotide |
| SEQ ID NO: 70 | GmAMT 5 polypeptide |
| SEQ ID NO: 71 | GmAMT 6 polynucleotide |
| SEQ ID NO: 72 | GmAMT 6 polypeptide |
| SEQ ID NO: 73 | GmAMT 7 polynucleotide |
| SEQ ID NO: 74 | GmAMT 7 polypeptide |
| SEQ ID NO: 75 | GmAMT 8 polynucleotide |
| SEQ ID NO: 76 | GmAMT 8 polypeptide |
| SEQ ID NO: 77 | GmAMT 9 polynucleotide |
| SEQ ID NO: 78 | GmAMT 9 polypeptide |
| SEQ ID NO: 79 | GmAMT 10 polynucleotide |
| SEQ ID NO: 80 | GmAMT 10 polypeptide |
| SEQ ID NO: 81 | GmAMT 11 polynucleotide |
| SEQ ID NO: 82 | GmAMT 11 polypeptide |

Therefore, in one aspect, the present invention relates to an isolated nucleic acid comprising an isolated polynucleotide sequence encoding an AMT protein. One embodiment of the invention is an isolated polynucleotide comprising a nucleotide sequence selected from the group consisting of: (a) the nucleotide sequence comprising SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79 or 81; (b) the nucleotide sequence encoding an amino acid sequence comprising SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80 or 82 and (c) the nucleotide sequence comprising at least 70% sequence identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79 or 81, wherein said polynucleotide encodes a polypeptide having AMT transporter activity.

Compositions of the invention include an isolated polypeptide comprising an amino acid sequence selected from the group consisting of: (a) the amino acid sequence comprising SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80 or 82 and (b) the amino acid sequence comprising at least 70% sequence identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80 or 82, wherein said polypeptide has AMT transporter activity.

In another aspect, the present invention relates to a recombinant expression cassette comprising a nucleic acid as described. Additionally, the present invention relates to a vector containing the recombinant expression cassette. Further, the vector containing the recombinant expression cassette can facilitate the transcription and translation of the nucleic acid in a host cell. The present invention also relates to the host cells able to express the polynucleotide of the present invention. A number of host cells could be used, such as but not limited to, microbial, mammalian, plant or insect.

In yet another embodiment, the present invention is directed to a transgenic plant or plant cells, containing the nucleic acids of the present invention. Preferred plants containing the polynucleotides of the present invention include but are not limited to maize, soybean, sunflower, sorghum, canola, wheat, alfalfa, cotton, rice, barley, tomato, switchgrass, myscanthus, triticale and millet. In another embodiment, the transgenic plant is a maize plant or plant cells. Another embodiment is the transgenic seeds from the transgenic plant. Another embodiment of the invention includes plants comprising an amt polypeptide of the invention operably linked to a promoter that drives expression in the plant. The plants of the invention can have altered AMT as compared to a control plant. In some plants, the AMT is altered in a vegetative tissue, a reproductive tissue, or a vegetative tissue and a reproductive tissue. Plants of the invention can have at least one of the following phenotypes including but not limited to: increased leaf size, increased ear size, increased seed size, increased endosperm size, alterations in the relative size of embryos and endosperms leading to changes in the relative levels of protein, oil and/or starch in the seeds, absence of tassels, absence of functional pollen bearing tassels or increased plant size.

Another embodiment of the invention would be plants that have been genetically modified at a genomic locus, wherein the genomic locus encodes an amt polypeptide of the invention.

Methods for increasing the activity of an amt polypeptide in a plant are provided. The method can comprise introducing into the plant an amt polynucleotide of the invention. Providing the polypeptide can decrease the number of cells in plant tissue, modulating the tissue growth and size.

Methods for reducing or eliminating the level of an amt polypeptide in the plant are provided. The level or activity of the polypeptide could also be reduced or eliminated in specific tissues, causing increased AMT in said tissues. Reducing the level and/or activity of the AMT polypeptide increases the number of cells produced in the associated tissue.

Compositions further include plants and seed having a DNA construct comprising a nucleotide sequence of interest operably linked to a promoter of the current invention. In specific embodiments, the DNA construct is stably integrated into the genome of the plant. The method comprises introducing into a plant a nucleotide sequence of interest operably linked to a promoter of the invention.

Figure 1:
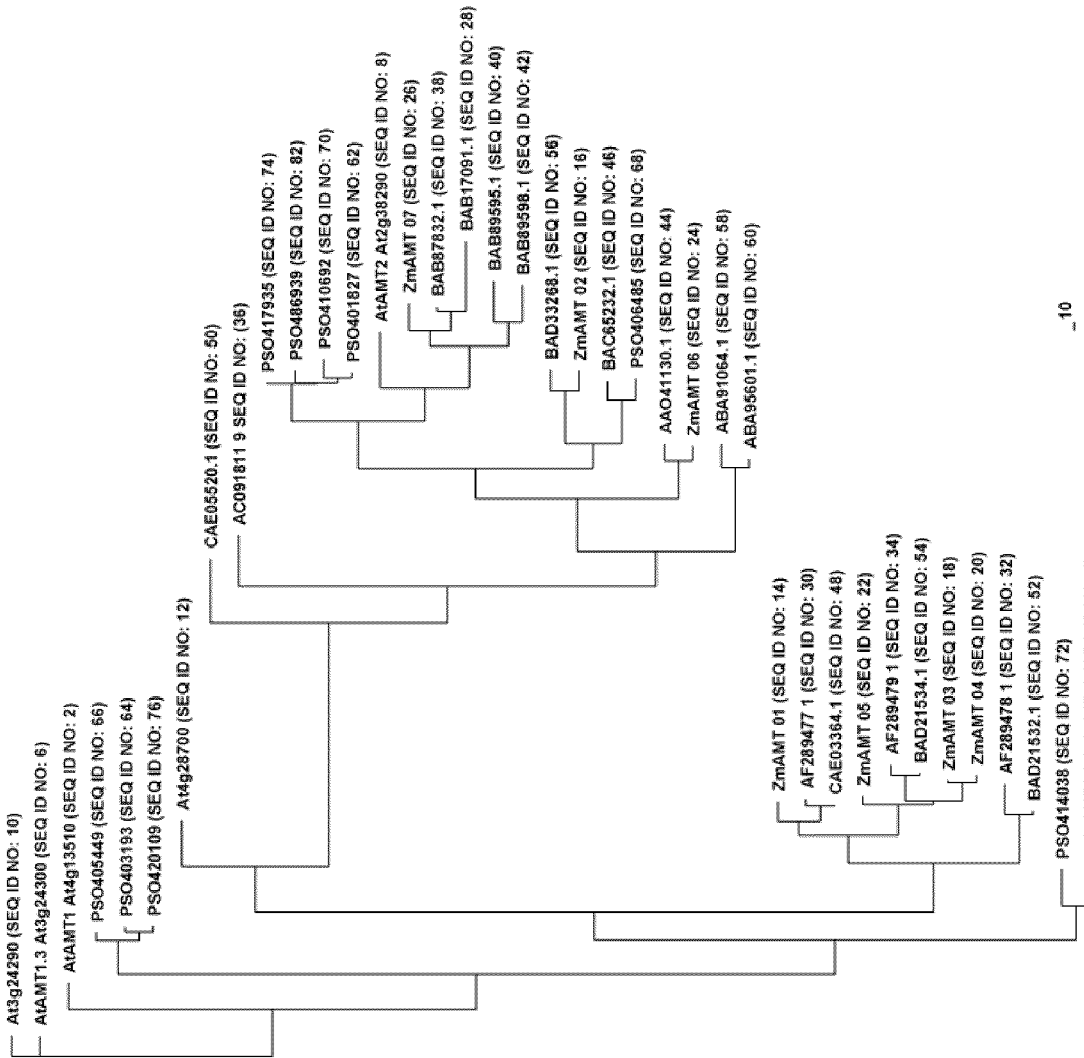
FIG. 1: Phylogentic tree of AMTs from *Arabidopsis*, rice, soybean and maize

Phylogenetic analyses of all the AMTs from *Arabidopsis*, rice, maize and soybean are shown in FIG. 1. The length of the line at the base of the figure represents an equivalent of 10 amino acid differences and could be used to approximate the amino acid differences between different ammonium transporter proteins from the individual branch lengths.

FIG. 2: Expression analysis of ZM-AMTs

In order to identify leaf specific/preferred/expressed AMT(s) in maize, Lynx MPSS expression analyses in ~300 libraries reveal that ZmAMT1 (SEQ ID NO: 14), 2, 7 are expressed both in roots and leaves whereas ZmAMT4 (SEQ ID NO: 20) is a root preferred AMT. ZmAMT6 (SEQ ID NO: 24) expresses at very low level in comparison to other Zm-AMTs. In case of ZmAMT5 there was no specific Lynx tag available.

Figure 3:
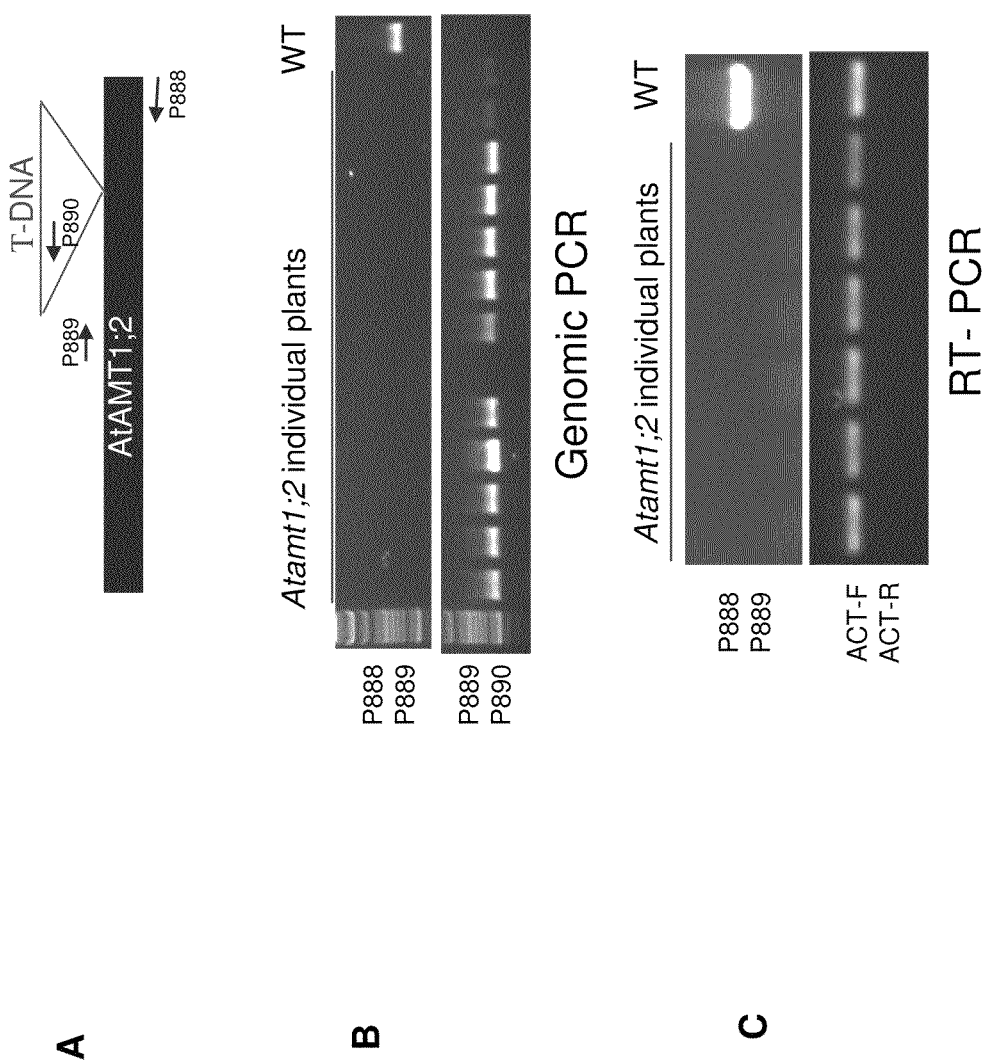

FIG. 3: Characterization of atamt1;2 T-DNA knock-out mutant

In cTP prediction analyses, AtAMT1;2 (SEQ ID NO: 4) possess a putative cTP. For functional analyses of AtAMT1;2 (SEQ ID NO: 4) and to determine it's role in N-assimilation, analyses identified a T-DNA mutant line (SM__3.15680) from the *Arabidopsis* T-DNA mutant data base. In this mutant line T-DNA was inserted in c-terminal of AtAMT1;2 (SEQ ID NO: 4) gene (FIG. 4A). Genomic PCRs using AtAMT1;2 (SEQ ID NO: 4) gene and T-DNA specific primers show that T-DNA is indeed inserted in the AtAMT1;2 (SEQ ID NO: 4) (FIG. 4B). AtAMT1;2 (SEQ ID NO: 4) gene specific primers flanking the T-DNA insert couldn't amplify any DNA region in mutant plants where as an expected PCR product was detected in wild type plant (FIG. 4B, upper panel). Similarly, genomic PCR with AtAMT1;2 (SEQ ID NO: 4) specific forward primer and T-DNA specific reverse primers amplify an expected product in mutant lines and nothing in wild type plants as expected (FIG. 4B, lower panel). Saturated RT-PCRs (35 cycles) analyses couldn't detect a full length atamt1;2 mRNA in mutant (FIG. 4C, upper panel) suggesting that AtAMT1;2 (SEQ ID NO: 4) is completely knocked out in this T-DNA mutant. Actin control RT-PCR worked fine in both mutant and wild type plants (FIG. 4C, lower panel).

FIG. 4: Knock-out of multiple AMTs in *Arabidopsis* by single RNAi vector

Six AMT genes are present in *Arabidopsis* genome. Hence, it is very likely that due to functional redundancy one might need to manipulate the expression of multiple AMTs simultaneously. Analyses of the DNA sequence of all these AMTs was performed which identified the high homology regions among them. There is a stretch of ~200 bp among AtAMT1;2 (SEQ ID NO: 4), AtAMT1 (SEQ ID NO: 2), AMT1;3 (SEQ ID NO: 6), At3g24290 (SEQ ID NO: 10) and At4g28700 (SEQ ID NO: 12) where as AMT2 (SEQ ID NO: 8) stood independent. Amplification of these regions was accomplished (bold and underlined in FIG. 4) by PCR from AtAMT1;2 (SEQ ID NO: 4) and AtAMT2 (SEQ ID NO: 8) and a multi-way ligation was performed to make an inverted repeat using ADH-intron as a spacer. The RNAi cassette of these hybrid inverted repeats is driven by constitutive or root specific or leaf specific promoter.

FIG. 5: Knock-out/down of multiple AMTs in Maize by single RNAi vector

Detailed analyses of all 7 maize AMTs were performed to identify the DNA regions showing high homology among different ZmAMTs. This analysis reveals that ZmAMT1 (SEQ ID NO: 14) and ZmAMT5 (SEQ ID NO: 22), ZmAMT3 (SEQ ID NO: 18) and ZmAMT4 (SEQ ID NO: 20) and ZmAMT2 (SEQ ID NO: 16), ZmAMT6 (SEQ ID NO: 24) and ZmAMT7 (SEQ ID NO: 26) form three separate groups and there is a very high homology in stretches of DNA sequences with in each group. Three DNA fragments (bold and underlined in FIG. 5) from ZmAMT 1, 4 and 7 (SEQ ID NOS: 14, 20 and 26) representing each of the different groups were amplified by PCR. Multi-way ligations were performed to make inverted repeats with hybrid of these 3 fragments and ADH intron as a spacer to facilitate the formation of stem-loop structure. This RNAi cassette of 'ZmAMT1 (SEQ ID NO: 14):ZmAMT4 (SEQ ID NO: 20):ZmAMT7 (SEQ ID NO: 26)' inverted repeats was driven by a constitutive (Zm-UBI promoter) or leaf-specific promoter. MOPAT driven by Zm-UBI promoter was used as herbicide resistance marker for selected. In addition to that RFP driven by a pericarp specific promoter LTP2 was also used to sort out the transgenic seeds (red) from there segregating non-transgenic seeds.

DETAILED DESCRIPTION OF THE INVENTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, BOTANY: PLANT BIOLOGY AND ITS RELATION TO HUMAN AFFAIRS, John Wiley (1982); CELL CULTURE AND SOMATIC CELL GENETICS OF PLANTS, vol. 1, Vasil, ed. (1984); Stanier, et al., THE MICROBIAL WORLD, $5^{th}$ ed., Prentice-Hall (1986); Dhringra and Sinclair, BASIC PLANT PATHOLOGY METHODS, CRC Press (1985); Maniatis, et al., MOLECULAR CLONING: A LABORATORY MANUAL (1982); DNA CLONING, vols. I and II, Glover, ed. (1985); OLIGONUCLEOTIDE SYNTHESIS, Gait, ed. (1984); NUCLEIC ACID HYBRIDIZATION, Hames and Higgins, eds. (1984); and the series METHODS IN ENZYMOLOGY, Colowick and Kaplan, eds, Academic Press, Inc., San Diego, Calif.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence is based amplification (NASBA, Cangene, Mississauga, Ontario), Q-Beta Replicase systems, transcription-based amplification system (TAS), and strand displacement amplification (SDA). See, e.g., DIAGNOSTIC MOLECULAR MICROBIOLOGY: PRINCIPLES AND APPLICATIONS, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., 1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for it's native substrate. Conservative substitution tables providing functionally similar amino acids are well known in is the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) *Proc. Natl. Acad. Sci. USA* 82:2306-9) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet, switchgrass, myscanthus, triticale and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "AMT nucleic acid" means a nucleic acid comprising a polynucleotide ("AMT polynucleotide") encoding a full length or partial length AMT polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, GUIDE TO MOLECULAR CLONING TECHNIQUES, from the series METHODS IN ENZYMOLOGY, vol. 152, Academic Press, Inc., San Diego, Calif. (1987); Sambrook, et al., MOLECULAR CLONING: A LABORATORY MANUAL, $2^{nd}$ ed., vols. 1-3 (1989); and CURRENT PROTOCOLS IN MOLECULAR BIOLOGY, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium and Triticum. A particularly preferred plant is Zea mays.

As used herein, "yield" may include reference to bushels per acre of a grain crop at harvest, as adjusted for grain moisture (15% typically for maize, for example). Grain moisture is measured in the grain at harvest. The adjusted test weight of grain is determined to be the weight in pounds per bushel, adjusted for grain moisture level at harvest.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions.

The term "AMT polypeptide" refers to one or more amino acid sequences. The term is also inclusive of fragments, variants, homologs, alleles or precursors (e.g., preproproteins or proproteins) thereof. A "AMT protein" comprises an amt polypeptide. Unless otherwise stated, the term "AMT nucleic acid" means a nucleic acid comprising a polynucleotide ("AMT polynucleotide") encoding an amt polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention; or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

The term "residue" or "amino acid residue" or "amino acid" are used interchangeably herein to refer to an amino acid that is incorporated into a protein, polypeptide or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-84: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part I, chapter 2, "Overview of principles of hybridization and the strategy of nucleic acid probe assays," Elsevier, N.Y. (1993); and CURRENT PROTOCOLS IN MOLECULAR BIOLOGY, chapter 2, Ausubel, et al., eds, Greene Publishing and Wiley-Interscience, New York (1995). Unless otherwise stated, in the present application high stringency is defined as hybridization in 4×SSC, 5× Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package®, Version 8 (available from Genetics Computer Group (GCG® programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65, and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, CURRENT PROTOCOLS IN MOLECULAR BIOLOGY, Chapter 19, Ausubel, et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The invention discloses AMT polynucleotides and polypeptides. The novel nucleotides and proteins of the invention have an expression pattern which indicates that they regulate ammonium transport and thus play an important role in plant development. The polynucleotides are expressed in various plant tissues. The polynucleotides and polypeptides thus provide an opportunity to manipulate plant development to alter seed and vegetative tissue development, timing or composition. This may be used to create a plant with altered N composition in source and sink.

Nucleic Acids

The present invention provides, inter alia, isolated nucleic acids of RNA, DNA and analogs and/or chimeras thereof, comprising an amt polynucleotide.

The present invention also includes polynucleotides optimized for expression in different organisms. For example, for expression of the polynucleotide in a maize plant, the sequence can be altered to account for specific codon preferences and to alter GC content as according to Murray, et al., supra. Maize codon usage for 28 genes from maize plants is listed in Table 4 of Murray et al., supra.

The AMT nucleic acids of the present invention comprise isolated AMT polynucleotides which are inclusive of:
  (a) a polynucleotide encoding an AMT polypeptide and conservatively modified and polymorphic variants thereof;
  (b) a polynucleotide having at least 70% sequence identity with polynucleotides of (a) or (b);
  (c) complementary sequences of polynucleotides of (a) or (b).

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb and frequently less than 10 kb. Use of cloning vectors, expression vectors, adapters and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEOβ-GAL, pRS403, pRS404, pRS405, pRS406, pRS413, pRS414, pRS415, pRS416, lambda MOSSlox and lambda MOSElox. Optional vectors for the present invention, include but are not limited to, lambda ZAP II and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20): 1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68 and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.*15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395; or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT Publication Number 96/19256. See also, Zhang, et al., (1997) *Proc. Natl. Acad. Sci. USA* 94:4504-9 and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated or cell- or tissue-specific/selective expression), a transcription initiation start site, a ribosome binding site, an RNA processing signal, a transcription termination site and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683, 439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30) and maize H3 histone (Lepetit, et al., (1992) *Mol. Gen. Genet.* 231:276-85 and Atanassvoa, et al., (1992) *Plant Journal* 2(3): 291-300); ALS promoter, as described in PCT Application Number WO 96/30530 and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes or alternatively from another plant gene or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50 and An, et al., (1989) *Plant Cell* 1:115-22) and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2, and 6, the Bronze-1 intron are known in the art. See generally, THE MAIZE HANDBOOK, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell*, 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference) or signal peptides which target proteins to the plastids such as that of rapeseed enoyl-Acp reductase (Verwaert, et al., (1994) *Plant Mol. Biol.* 26:189-202) are useful in the invention. The barley alpha amylase signal sequence fused to the AMT polynucleotide is the preferred construct for expression in maize for the present invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11, and Berger, et al., (1989) *Proc. Natl. Acad. Sci. USA*, 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about $1/10,000$ transcripts to about $1/100,000$ transcripts to about $1/500,000$ transcripts. Conversely, a "strong promoter" drives expression of a coding sequence at a "high level," or about $1/10$ transcripts to about $1/100$ transcripts to about $1/1,000$ transcripts.

One of skill would recognize that modifications could be made to a protein of the present invention without diminishing its biological activity. Some modifications may be made to facilitate the cloning, expression or incorporation of the targeting molecule into a fusion protein. Such modifications are well known to those of skill in the art and include, for example, a methionine added at the amino terminus to provide an initiation site or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., METHODS IN YEAST GENETICS, Cold Spring Harbor Laboratory (1982) is a well recognized work describing the various methods available to produce the protein in yeast. Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect or plant origin. Mammalian cell systems often will be in the form of monolayers of cells although mammalian cell suspensions may also be used. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins of the present invention are available, for instance, from the American Type Culture Collection Catalogue of Cell Lines and Hybridomas ($7^{th}$ ed., 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included.

An example of a splicing sequence is the VP1 intron from SV40 (Sprague, et al., (1983) *J. Virol.* 45:773-81). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in DNA CLONING: A PRACTICAL APPROACH, vol. II, Glover, ed., IRL Press, Arlington, Va., pp. 213-38 (1985)).

In addition, the gene for AMT placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert an amt polynucleotide into a plant host, including biological and physical plant transformation protocols. See, e.g., Miki, et al., "Procedure for Introducing Foreign DNA into Plants," in METHODS IN PLANT MOLECULAR BIOLOGY AND BIOTECHNOLOGY, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch, et al., (1985) *Science* 227: 1229-31), electroporation, micro-injection, and biolistic bombardment.

Expression cassettes and vectors and in vitro culture methods for plant cell or tissue transformation and regeneration of plants are known and available. See, e.g., Gruber, et al., "Vectors for Plant Transformation," in METHODS IN PLANT MOLECULAR BIOLOGY AND BIOTECHNOLOGY, supra, pp. 89-119.

The isolated polynucleotides or polypeptides may be introduced into the plant by one or more techniques typically used for direct delivery into cells. Such protocols may vary depending on the type of organism, cell, plant or plant cell, i.e., monocot or dicot, targeted for gene modification. Suitable methods of transforming plant cells include microinjection (Crossway, et al., (1986) *Biotechniques* 4:320-334 and U.S. Pat. No. 6,300,543), electroporation (Riggs, et al., (1986) *Proc. Natl. Acad. Sci. USA* 83:5602-5606, direct gene transfer (Paszkowski, et al., (1984) *EMBO J.* 3:2717-2722) and ballistic particle acceleration (see, for example, Sanford, et al., U.S. Pat. No. 4,945,050; WO 91/10725 and McCabe, et al., (1988) *Biotechnology* 6:923-926). Also see, Tomes, et al., Direct DNA Transfer into Intact Plant Cells Via Microprojectile Bombardment. pp. 197-213 in Plant Cell, Tissue and Organ Culture, Fundamental Methods. eds. O. L. Gamborg & G. C. Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839 and Gordon-Kamm, et al., (1990) *Plant Cell* 2:603-618 (maize); Hooydaas-Van Slogteren and Hooykaas (1984) *Nature* (London) 311:763-764; Bytebier, et al., (1987) *Proc. Natl. Acad. Sci. USA* 84:5345-5349 (Liliaceae); De Wet, et al., (1985) *In The Experimental Manipulation of Ovule Tissues,* ed. G. P. Chapman, et al., pp. 197-209 Longman, N.Y. (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693, 512 (sonication); D'Halluin, et al., (1992) *Plant Cell* 4:1495-1505 (electroporation); Li, et al., (1993) *Plant Cell Reports* 12:250-255 and Christou and Ford, (1995) Annals of Botany 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185), all of which are herein incorporated by reference.

Agrobacterium-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658, 082; U.S. patent application Ser. No. 913,914, filed Oct. 1, 1986, as referenced in U.S. Pat. No. 5,262,306, issued Nov. 16, 1993 and Simpson, et al., (1986) *Plant Mol. Biol.* 6:403-15 (also referenced in the '306 patent), all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon, switchgrass, myscanthus, triticale and pepper.

The selection of either *A. tumefaciens* or *A. rhizogenes* will depend on the plant being transformed thereby. In general *A. tumefaciens* is the preferred organism for transformation. Most dicotyledonous plants, some gymnosperms and a few monocotyledonous plants (e.g., certain members of the *Liliales* and *Arales*) are susceptible to infection with *A. tumefaciens. A. rhizogenes* also has a wide host range, embracing most dicots and some gymnosperms, which includes members of the Leguminosae, Compositae and Chenopodiaceae. Monocot plants can now be transformed with some success. EP Patent Application Number 604 662 A1 discloses a method for transforming monocots using *Agrobacterium*. EP Application Number 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra and U.S. patent application Ser. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206 and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731 and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161 and Draper, et al., (1982) *Plant Cell Physiol.* 23:451.

Electroporation of protoplasts and whole cells and tissues has also been described. See, e.g., Donn, et al., (1990) in *Abstracts of the VIIth Int'l. Congress on Plant Cell and Tissue Culture IAPTC*, A2-38, p. 53; D'Halluin, et al., (1992) *Plant Cell* 4:1495-505 and Spencer, et al., (1994) *Plant Mol. Biol.* 24:51-61.

Increasing the Activity and/or Level of an amt Polypeptide

Methods are provided to increase the activity and/or level of the AMT polypeptide of the invention. An increase in the level and/or activity of the AMT polypeptide of the invention can be achieved by providing to the plant an amt polypeptide. The AMT polypeptide can be provided by introducing the amino acid sequence encoding the AMT polypeptide into the plant, introducing into the plant a nucleotide sequence encoding an amt polypeptide or alternatively by modifying a genomic locus encoding the AMT polypeptide of the invention.

As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having AMT transporter activity. It is also recognized that the methods of the invention may employ a polynucleotide that is not capable of directing, in the transformed plant, the expression of a protein or an RNA. Thus, the level and/or activity of an amt polypeptide may be increased by altering the gene encoding the AMT polypeptide or its promoter. See, e.g., Kmiec, U.S. Pat. No. 5,565,350; Zarling, et al., PCT/US93/03868. Therefore mutagenized plants that carry mutations in AMT genes, where the mutations increase expression of the AMT gene or increase the AMT transporter activity of the encoded AMT polypeptide are provided.

Reducing the Activity and/or Level of an amt Polypeptide

Methods are provided to reduce or eliminate the activity of an amt polypeptide of the invention by transforming a plant cell with an expression cassette that expresses a polynucleotide that inhibits the expression of the AMT polypeptide. The polynucleotide may inhibit the expression of the AMT polypeptide directly, by preventing transcription or translation of the AMT messenger RNA, or indirectly, by encoding a polypeptide that inhibits the transcription or translation of an amt gene encoding an amt polypeptide. Methods for inhibiting or eliminating the expression of a gene in a plant are well known in the art, and any such method may be used in the present invention to inhibit the expression of an amt polypeptide.

In accordance with the present invention, the expression of an amt polypeptide is inhibited if the protein level of the AMT polypeptide is less than 70% of the protein level of the same AMT polypeptide in a plant that has not been genetically modified or mutagenized to inhibit the expression of that AMT polypeptide. In particular embodiments of the invention, the protein level of the AMT polypeptide in a modified plant according to the invention is less than 60%, less than 50%, less than 40%, less than 30%, less than 20%, less than 10%, less than 5% or less than 2% of the protein level of the same AMT polypeptide in a plant that is not a mutant or that has not been genetically modified to inhibit the expression of that AMT polypeptide. The expression level of the AMT polypeptide may be measured directly, for example, by assaying for the level of AMT polypeptide expressed in the plant cell or plant, or indirectly, for example, by measuring the AMT transporter activity of the AMT polypeptide in the plant cell or plant, or by measuring the AMT in the plant. Methods for performing such assays are described elsewhere herein.

In other embodiments of the invention, the activity of the AMT polypeptides is reduced or eliminated by transforming a plant cell with an expression cassette comprising a polynucleotide encoding a polypeptide that inhibits the activity of an amt polypeptide. The AMT transporter activity of an amt polypeptide is inhibited according to the present invention if the AMT transporter activity of the AMT polypeptide is less than 70% of the AMT transporter activity of the same AMT polypeptide in a plant that has not been modified to inhibit the AMT transporter activity of that AMT polypeptide. In particular embodiments of the invention, the AMT transporter activity of the AMT polypeptide in a modified plant according to the invention is less than 60%, less than 50%, less than 40%, less than 30%, less than 20%, less than 10% or less than 5% of the AMT transporter activity of the same AMT polypeptide in a plant that that has not been modified to inhibit the expression of that AMT polypeptide. The AMT transporter activity of an amt polypeptide is "eliminated" according to the invention when it is not detectable by the assay methods described elsewhere herein. Methods of determining the AMT transporter activity of an amt polypeptide are described elsewhere herein.

In other embodiments, the activity of an amt polypeptide may be reduced or eliminated by disrupting the gene encoding the AMT polypeptide. The invention encompasses mutagenized plants that carry mutations in AMT genes, where the mutations reduce expression of the AMT gene or inhibit the AMT transporter activity of the encoded AMT polypeptide.

Thus, many methods may be used to reduce or eliminate the activity of an amt polypeptide. In addition, more than one method may be used to reduce the activity of a single AMT polypeptide. Non-limiting examples of methods of reducing or eliminating the expression of AMT polypeptides are given below.

1. Polynucleotide-Based Methods:

In some embodiments of the present invention, a plant is transformed with an expression cassette that is capable of expressing a polynucleotide that inhibits the expression of an amt polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one AMT polypeptide is an expression cassette capable of producing an RNA molecule that inhibits the transcription and/or translation of at least one AMT polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an amt polypeptide are given below.

i. Sense Suppression/Cosuppression

In some embodiments of the invention, inhibition of the expression of an amt polypeptide may be obtained by sense suppression or cosuppression. For cosuppression, an expression cassette is designed to express an RNA molecule corresponding to all or part of a messenger RNA encoding an amt polypeptide in the "sense" orientation. Over expression of the RNA molecule can result in reduced expression of the native gene. Accordingly, multiple plant lines transformed with the cosuppression expression cassette are screened to identify those that show the greatest inhibition of AMT polypeptide expression.

The polynucleotide used for cosuppression may correspond to all or part of the sequence encoding the AMT polypeptide, all or part of the 5' and/or 3' untranslated region of an amt polypeptide transcript or all or part of both the coding sequence and the untranslated regions of a transcript encoding an amt polypeptide. In some embodiments where the polynucleotide comprises all or part of the coding region for the AMT polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657; each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

ii. Antisense Suppression

In some embodiments of the invention, inhibition of the expression of the AMT polypeptide may be obtained by antisense suppression. For antisense suppression, the expression cassette is designed to express an RNA molecule complementary to all or part of a messenger RNA encoding the AMT polypeptide. Over expression of the antisense RNA molecule can result in reduced expression of the native gene. Accordingly, multiple plant lines transformed with the antisense suppression expression cassette are screened to identify those that show the greatest inhibition of AMT polypeptide expression.

The polynucleotide for use in antisense suppression may correspond to all or part of the complement of the sequence encoding the AMT polypeptide, all or part of the complement of the 5' and/or 3' untranslated region of the AMT transcript or all or part of the complement of both the coding sequence and the untranslated regions of a transcript encoding the AMT polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the invention, inhibition of the expression of an amt polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of AMT polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 99/49029, WO 99/53050, WO 99/61631 and WO 00/49035, each of which is herein incorporated by reference.

iv. Hairpin RNA Interference and Intron-Containing Hairpin RNA Interference

In some embodiments of the invention, inhibition of the expression of an amt polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295, and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Natl. Acad. Sci.* 99(4): 16499-16506; Sijen, et al., *Curr. Biol.* (2001) 11:436-440), herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the AMT polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the AMT polypeptide. Thus, the polynucleotide causes the degradation of the endogenous messenger RNA, resulting in reduced expression of the AMT polypeptide. This method is described, for example, in U.S. Pat. No. 4,987,071, herein incorporated by reference.

vii. Small Interfering RNA or Micro RNA

In some embodiments of the invention, inhibition of the expression of an amt polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of AMT expression, the 22-nucleotide sequence is selected from an amt transcript sequence and contains 22 nucleotides of said AMT sequence in sense orientation and 21 nucleotides of a corresponding antisense sequence that is complementary to the sense sequence. miRNA molecules are highly efficient at inhibiting the expression of endogenous genes and the RNA interference they induce is inherited by subsequent generations of plants.

2. Polypeptide-Based Inhibition of Gene Expression

In one embodiment, the polynucleotide encodes a zinc finger protein that binds to a gene encoding an amt polypeptide, resulting in reduced expression of the gene. In particular embodiments, the zinc finger protein binds to a regulatory region of an amt gene. In other embodiments, the zinc finger protein binds to a messenger RNA encoding an amt polypeptide and prevents its translation. Methods of selecting sites for targeting by zinc finger proteins have been described, for example, in U.S. Pat. No. 6,453,242 and methods for using zinc finger proteins to inhibit the expression of genes in plants are described, for example, in US Patent Application Publication Number 2003/0037355, each of which is herein incorporated by reference.

3. Polypeptide-Based Inhibition of Protein Activity

In some embodiments of the invention, the polynucleotide encodes an antibody that binds to at least one AMT polypeptide and reduces the AMT transporter activity of the AMT polypeptide. In another embodiment, the binding of the antibody results in increased turnover of the antibody-AMT complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an amt polypeptide is reduced or eliminated by disrupting the gene encoding the AMT polypeptide. The gene encoding the AMT polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced AMT transporter activity.

i. Transposon Tagging

In one embodiment of the invention, transposon tagging is used to reduce or eliminate the AMT activity of one or more AMT polypeptide. Transposon tagging comprises inserting a transposon within an endogenous AMT gene to reduce or eliminate expression of the AMT polypeptide. "AMT gene" is intended to mean the gene that encodes an amt polypeptide according to the invention.

In this embodiment, the expression of one or more AMT polypeptide is reduced or eliminated by inserting a transposon within a regulatory region or coding region of the gene encoding the AMT polypeptide. A transposon that is within an exon, intron, 5' or 3' untranslated sequence, a promoter or any other regulatory sequence of an amt gene may be used to reduce or eliminate the expression and/or activity of the encoded AMT is polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (AMT transporter activity) of the encoded protein are well known in the art. Insertional mutations in gene exons usually result in null-mutants. Mutations in conserved residues are particularly effective in inhibiting the AMT transporter activity of the encoded protein. Conserved residues of plant AMT polypeptides suitable for mutagenesis with the goal to eliminate AMT transporter activity have been described. Such mutants can be isolated according to well-known procedures, and mutations in different AMT loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more AMT polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731, 181; 5,756,325; 5,760,012; 5,795,972 and 5,871,984, each of which are herein incorporated by reference. See also, WO 98/49350, WO 99/07865, WO 99/25821 and Beetham, et al., (1999) *Proc. Natl. Acad. Sci. USA* 96:8774-8778, each of which is herein incorporated by reference.

iii. Modulating AMT Transporter Activity

In specific methods, the level and/or activity of an amt regulator in a plant is decreased by increasing the level or activity of the AMT polypeptide in the plant. Methods for increasing the level and/or activity of AMT polypeptides in a plant are discussed elsewhere herein. Briefly, such methods comprise providing an amt polypeptide of the invention to a plant and thereby increasing the level and/or activity of the AMT polypeptide. In other embodiments, an amt nucleotide sequence encoding an amt polypeptide can be provided by introducing into the plant a polynucleotide comprising an amt nucleotide sequence of the invention, expressing the AMT sequence, increasing the activity of the AMT polypeptide and thereby decreasing the ammonium uptake or transport in the plant or plant part. In other embodiments, the AMT nucleotide construct introduced into the plant is stably incorporated into the genome of the plant.

As discussed above, one of skill will recognize the appropriate promoter to use to modulate the level/activity of an amt transporter in the plant. Exemplary promoters for this embodiment have been disclosed elsewhere herein.

Accordingly, the present invention further provides plants having a modified number of cells when compared to the number of cells of a control plant tissue. In one embodiment, the plant of the invention has an increased level/activity of the AMT polypeptide of the invention and thus has an increased Ammonium transport in the plant tissue. In other embodiments, the plant of the invention has a reduced or eliminated level of the AMT polypeptide of the invention and thus has an increased NUE in the plant tissue. In other embodiments, such plants have stably incorporated into their genome a nucleic acid molecule comprising an amt nucleotide sequence of the invention operably linked to a promoter that drives expression in the plant cell.

iv. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development or radial expansion.

Methods for modulating root development in a plant are provided. The methods comprise modulating the level and/or activity of the AMT polypeptide in the plant. In one method, an amt sequence of the invention is provided to the plant. In another method, the AMT nucleotide sequence is provided by introducing into the plant a polynucleotide comprising an amt nucleotide sequence of the invention, expressing the AMT sequence and thereby modifying root development. In still other methods, the AMT nucleotide construct introduced into the plant is stably incorporated into the genome of the plant.

In other methods, root development is modulated by altering the level or activity of the AMT polypeptide in the plant. A decrease in AMT activity can result in at least one or more of the following alterations to root development, including, but not limited to, larger root meristems, increased in root growth, enhanced radial expansion, an enhanced vasculature system, increased root branching, more adventitious roots and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by decreasing the activity and/or level of the AMT polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by decreasing the level and/or activity of the AMT polypeptide also finds use in promoting in vitro propagation of explants.

Furthermore, higher root biomass production due to an decreased level and/or activity of AMT activity has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has an increased level/activity of the AMT polypeptide of the invention and has enhanced root growth and/or root biomass. In other embodiments, such plants have stably incorporated into their genome a nucleic acid molecule comprising an amt nucleotide sequence of the invention operably linked to a promoter that drives expression in the plant cell.

v. Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and US Patent Application Publication Number 2003/0074698, each of which is herein incorporated by reference.

The method for modulating shoot and/or leaf development in a plant comprises modulating the activity and/or level of an AMT polypeptide of the invention. In one embodiment, an amt sequence of the invention is provided. In other embodiments, the AMT nucleotide sequence can be provided by introducing into the plant a polynucleotide comprising an amt nucleotide sequence of the invention, expressing the AMT sequence, and thereby modifying shoot and/or leaf development. In other embodiments, the AMT nucleotide construct introduced into the plant is stably incorporated into the genome of the plant.

In specific embodiments, shoot or leaf development is modulated by increasing the level and/or activity of the AMT polypeptide in the plant. An increase in AMT activity can result in at least one or more of the following alterations in shoot and/or leaf development, including, but not limited to, reduced leaf number, reduced leaf surface, reduced vascular, shorter internodes and stunted growth and retarded leaf senescence, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters and leaf-preferred promoters. Exemplary promoters have been disclosed elsewhere herein.

Increasing AMT activity and/or level in a plant results in shorter internodes and stunted growth. Thus, the methods of the invention find use in producing dwarf plants. In addition, as discussed above, modulation AMT activity in the plant modulates both root and shoot growth. Thus, the present invention further provides methods for altering the root/shoot ratio. Shoot or leaf development can further be modulated by decreasing the level and/or activity of the AMT polypeptide in the plant.

Accordingly, the present invention further provides plants having modulated shoot and/or leaf development when compared to a control plant. In some embodiments, the plant of the invention has an increased level/activity of the AMT polypeptide of the invention. In other embodiments, the plant of the invention has a decreased level/activity of the AMT polypeptide of the invention.

vi Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the AMT polypeptide has not been modulated. "Modulating floral development" further includes any alteration in the timing of the development of a plant's reproductive tissue (i.e., a delayed or a accelerated timing of floral development) when compared to a control plant in which the activity or level of the AMT polypeptide has not been modulated. Macroscopic alterations may include changes in size, shape, number or location of reproductive organs, the developmental time period that these structures form or the ability to maintain or proceed through the flowering process in times of environmental stress. Microscopic alterations may include changes to the types or shapes of cells that make up the reproductive organs.

The method for modulating floral development in a plant comprises modulating AMT activity in a plant. In one method, an AMT sequence of the invention is provided. AN AMT nucleotide sequence can be provided by introducing into the plant a polynucleotide comprising an amt nucleotide sequence of the invention, expressing the AMT sequence and thereby modifying floral development. In other embodiments, the AMT nucleotide construct introduced into the plant is stably incorporated into the genome of the plant.

In specific methods, floral development is modulated by increasing the level or activity of the AMT polypeptide in the plant. An increase in AMT activity can result in at least one or more of the following alterations in floral development, including, but not limited to, retarded flowering, reduced number of flowers, partial male sterility and reduced seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S111-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters and inflorescence-preferred promoters.

In other methods, floral development is modulated by decreasing the level and/or activity of the AMT sequence of the invention. Such methods can comprise introducing an amt nucleotide sequence into the plant and decreasing the activity of the AMT polypeptide. In other methods, the AMT nucleotide construct introduced into the plant is stably incorporated into the genome of the plant. Decreasing expression of the AMT sequence of the invention can modulate floral development during periods of stress. Such methods are described elsewhere herein. Accordingly, the present invention further provides plants having modulated floral development when compared to the floral development of a control plant. Compositions include plants having a decreased level/activity of the AMT polypeptide of the invention and having an altered floral development. Compositions also include plants having a decreased level/activity of the AMT polypeptide of the invention wherein the plant maintains or proceeds through the flowering process in times of stress.

Methods are also provided for the use of the AMT sequences of the invention to increase nitrogen use efficiency. The method comprises decreasing or increasing the activity of the AMT sequences in a plant or plant part, such as the roots, shoot, epidermal cells, etc.

As discussed above, one of skill will recognize the appropriate promoter to use to manipulate the expression of AMTs. Exemplary promoters of this embodiment include constitutive promoters, inducible promoters and root or shoot or leaf preferred promoters.

vii. Method of Use for AMT Promoter Polynucleotides

The polynucleotides comprising the AMT promoters disclosed in the present invention, as well as variants and fragments thereof, are useful in the genetic manipulation of any host cell, preferably plant cell, when assembled with a DNA construct such that the promoter sequence is operably linked to a nucleotide sequence comprising a polynucleotide of interest. In this manner, the AMT promoter polynucleotides of the invention are provided in expression cassettes along with a polynucleotide sequence of interest for expression in the host cell of interest. As discussed in Example XX below, the AMT promoter sequences of the invention are expressed in a variety of tissues and thus the promoter sequences can find use in regulating the temporal and/or the spatial expression of polynucleotides of interest.

Synthetic hybrid promoter regions are known in the art. Such regions comprise upstream promoter elements of one polynucleotide operably linked to the promoter element of another polynucleotide. In an embodiment of the invention, heterologous sequence expression is controlled by a synthetic hybrid promoter comprising the AMT promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton, et al., (1998) *Curr. Opin. Plant Biol.* 1:311-315. Alternatively, a synthetic AMT promoter sequence may comprise duplications of the upstream promoter elements found within the AMT promoter sequences.

It is recognized that the promoter sequence of the invention may be used with its native AMT coding sequences. A DNA construct comprising the AMT promoter operably linked with its native AMT gene may be used to transform any plant of interest to bring about a desired phenotypic change, such as, modulating root, shoot, leaf, floral and embryo development, stress tolerance and any other phenotype described elsewhere herein.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics and commercial products. Genes of interest include, generally, those involved in oil, starch, carbohydrate or nutrient metabolism as well as those affecting kernel size, sucrose loading, and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232, 529); balanced amino acids (e.g., hordothionins (U.S. Pat. Nos. 5,990,389; 5,885,801; 5,885,802 and 5,703,409); barley high lysine (Williamson, et al., (1987) *Eur. J. Biochem.* 165: 99-106 and WO 98/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12: 123)); increased digestibility (e.g., modified storage proteins (U.S. patent application Ser. No. 10/053,410, filed Nov. 7, 2001) and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366, 892; 5,747,450; 5,737,514; 5723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene) and glyphosate resistance (EPSPS gene)) and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)) and polymers or bioplastics (e.g., U.S. Pat. No. 5.602,321; beta-ketothiolase, polyhydroxybutyrate synthase and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see, U.S. Pat. No. 5,583,210), stalk strength, flowering time or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias, et al., (1996) *Plant Cell* 8:1533-44); AKT1, a component of the potassium uptake apparatus in *Arabidopsis,* (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem* 27:16749-16752, Arredondo-Peter, et al., (1997) *Plant Physiol.* 115: 1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch and protein content can be genetically altered in addition to using traditional breeding methods. Modifications include increasing content of oleic acid, saturated and unsaturated oils, increasing levels of lysine and sulfur, providing essential amino acids and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016 and the chymotrypsin inhibitor from barley, described in Williamson, et al., (1987)

*Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996 and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359; both of which are herein incorporated by reference) and rice (Musumura, et al., (1989) *Plant Mol. Biol.* 12:123, herein incorporated by reference). Other agronomically important genes encode latex, Floury 2, growth factors, seed storage factors and transcription factors.

Insect resistance genes may encode resistance to pests that have great yield drag such as rootworm, cutworm, European Corn Borer and the like. Such genes include, for example, *Bacillus thuringiensis* toxic protein genes (U.S. Pat. Nos. 5,366,892; 5,747,450; 5,736,514; 5,723,756; 5,593,881 and Geiser, et al., (1986) *Gene* 48:109); and the like.

Genes encoding disease resistance traits include detoxification genes, such as against fumonosin (U.S. Pat. No. 5,792,931); avirulence (avr) and disease resistance (R) genes (Jones, et al., (1994) *Science* 266:789; Martin, et al., (1993) *Science* 262:1432 and Mindrinos, et al., (1994) *Cell* 78:1089), and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene) or other such genes known in the art. The bar gene encodes resistance to the herbicide basta, the nptII gene encodes resistance to the antibiotics kanamycin and geneticin and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase) and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones and the like. The level of proteins, particularly modified proteins having improved amino acid distribution to improve the nutrient value of the plant, can be increased. This is achieved by the expression of such proteins having enhanced amino acid content.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

Isolation of AMT Sequences

A routine for identifying all members of a given species' ammonium transporter (AMT) gene family was employed. First, a diverse set of all the known available members of the gene family as protein sequences was prepared from public and proprietary sources. This data could include orthologous sequences from other species besides these four. Then, as in the example of maize, these protein query sequences were BLAST algorithm searched against a combination of proprietary and public maize, genomic or transcript, nucleotide sequence datasets and a non-redundant set of candidate AMTs or 'hits' was identified. These sequences were combined with any existing maize gene family sequences and then curated and edited to arrive at a new working set of unique maize AMT gene or transcript sequences and their translations. This search for gene family members was repeated. If there were recovered new sequences whose nucleotide sequences were unique (not same-gene matches), the process repeated until completion, that is until no new and distinct nucleotide sequences were found. In this way it was determined that the maize AMT family of genes consisted of at least seven members. Eleven distinct soybean sequences were found. Without the complete genome sequences of maize or soybean available, researchers were less certain of the exact gene family size, than they were for *Arabidopsis* (6 members) and rice (17 members). The availability of complete genome sequences for *Arabidopsis* and rice simplified the search, aided also by availability of fairly mature gene models and annotations for these species.

Example 2

Transformation and Regeneration of Transgenic Plants

Immature maize embryos from greenhouse donor plants are bombarded with a plasmid containing the AMT sequence operably linked to the drought-inducible promoter RAB17 promoter (Vilardell, et al., (1990) *Plant Mol Biol* 14:423-432) and the selectable marker gene PAT, which confers resistance to the herbicide Bialaphos. Alternatively, the selectable marker gene is provided on a separate plasmid. Transformation is performed as follows. Media recipes follow below.

Preparation of Target Tissue:

The ears are husked and surface sterilized in 30% Clorox® bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA:

A plasmid vector comprising the AMT sequence operably linked to an ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment:

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment:

Following bombardment, the embryos are kept on 560Y medium for 2 days, then transferred to 560R selection medium containing 3 mg/liter Bialaphos and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for increased drought tolerance. Assays to measure improved drought tolerance are routine in the art and include, for example, increased kernel-earring capacity yields under drought conditions when compared to control maize plants under identical environmental conditions. Alternatively, the transformed plants can be monitored for a modulation in meristem development (i.e., a decrease in spikelet formation on the ear). See, for example, Bruce, et al., (2002) *Journal of Experimental Botany* 53:1-13.

Bombardment and Culture Media:

Bombardment medium (560Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D and 2.88 g/l L-proline (brought to volume with D-I $H_2O$ following adjustment to pH 5.8 with KOH); 2.0 g/l Gelrite® (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite® (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose and 1.0 ml/l of 0.1 mM abscisic acid (brought to volume with polished D-I $H_2O$ after adjusting to pH 5.6); 3.0 g/l Gelrite® (added after bringing to volume with D-I $H_2O$) and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL and 0.40 g/l glycine brought to volume with polished D-I $H_2O$), 0.1 g/l myo-inositol and 40.0 g/l sucrose (brought to volume with polished D-I $H_2O$ after adjusting pH to 5.6) and 6 g/l bacto™-agar (added after bringing to volume with polished D-I $H_2O$), sterilized and cooled to 60° C.

Example 3

*Agrobacterium*-Mediated Transformation

For *Agrobacterium*-mediated transformation of maize with an antisense sequence of the AMT sequence of the present invention, preferably the method of Zhao is employed (U.S. Pat. No. 5,981,840 and PCT Patent Publication Number WO98/32326, the contents of which are hereby incorporated by reference). Briefly, immature embryos are isolated from maize and the embryos contacted with a suspension of *Agrobacterium*, where the bacteria are capable of transferring the antisense AMT sequences to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step) and preferably calli grown on selective medium are cultured on solid medium to regenerate the plants. Plants are monitored and scored for a modulation in tissue development.

Example 4

Soybean Embryo Transformation

Soybean embryos are bombarded with a plasmid containing an antisense AMT sequences operably linked to an ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette comprising an antisense AMT sequence operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 5

Sunflower Meristem Tissue Transformation

Sunflower meristem tissues are transformed with an expression cassette containing an antisense AMT sequences operably linked to a ubiquitin promoter as follows (see also, European Patent Number EP 0 486233, herein incorporated by reference and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox® bleach solution with the addition of two drops of Tween® 20 per 50 ml of solution. The seeds are rinsed twice with sterile distilled water.

Split embryonic axis explants are prepared by a modification of procedures described by Schrammeijer, et al. (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.*, 15:473-497), Shepard's vitamin additions (Shepard, (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the AMT gene operably linked to the ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bacto® peptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$ and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite®, pH 5.6) and grown under conditions described for explant culture. The upper portion of the seedling is removed, a 1 cm vertical slice is made in the hypocotyl and the transformed shoot inserted into the cut. The entire area is wrapped with parafilm® to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by AMT activity analysis of leaf extracts while transgenic seeds harvested from NPTII-positive $T_0$ plants are identified by AMT activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox® bleach solution with the addition of two to three drops of Tween® 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bacto®peptone, and 5 g/l NaCl, pH 7.0) in the presence of 50 μg/l kanamycin is resuspended in an inoculation medium (12.5 mM 2-mM 2-(N-morpholino)ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E) and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive (i.e., a decrease in AMT expression) explants are identified, those shoots that fail to exhibit a decrease in AMT activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for a decreased AMT expression are grafted to Pioneer hybrid 6440 in vitro-grown sunflower seedling rootstock. The rootstocks are prepared in the following manner. Seeds are dehulled and surface-sterilized for 20 minutes in a 20% Clorox® bleach solution with the addition of two to three drops of Tween® 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite® pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm®. After one week of culture on the medium, grafted plants are transferred to soil. In the first two weeks, they are maintained under high humidity conditions to acclimatize to a greenhouse environment.

Example 6

Identification, Phylogenetic Analysis and Chloroplast Targeting Peptide (cTP) Predictions of AMTs in *Arabidopsis*, Rice, Soybean and Maize Taking a 'genomic' approach AMTs were identified in several higher plants. In *Arabidopsis* 6 AMTs have been identified, and phylogenetic analyses reveals that AtAMT1 (SEQ ID NO: 2) AtAMT1;2 (SEQ ID NO: 4), AtAMT1;3 (SEQ ID NO: 6) and At3g24290 (SEQ ID NO: 10) cluster in one group where as AtAMT2 (SEQ ID NO: 8) and At4g28700 (SEQ ID NO: 12) are independent. Chloroplast targeting peptide (cTP) prediction by ChloroP program reveals that AtAMT1;2 (SEQ ID NO: 4) have a putative cTP (with 55% probability) where as all other AtAMTs did not contain any predicted cTP In rice, soybean and maize, 17, 11, 7 AMTs have been identified, respectively. cTP prediction in AMTs proteins from maize and soybean didn't identify any AMT candidate with a putative cTP, however in rice one AMT has putative cTP with more than 50% probability. Phylogenetic analyses of all the AMTs from *Arabidopsis*, rice, maize and soybean are shown in FIG. 1.

Example 7

Expression Analysis of AMTs in Maize

In order to identify leaf specific/preferred/expressed AMT(s) in maize, Lynx MPSS expression analyses in ~300 libraries reveal that ZmAMT1 (SEQ ID NO: 14), 2, 7 are expressed both in roots and leaves (FIG. 2) whereas ZmAMT4 (SEQ ID NO: 20) is a root preferred AMT. ZmAMT6 (SEQ ID NO: 24) expresses at very low level in comparison to other ZmAMTs. In case of ZmAMT5 there was no specific Lynx tag available. Researchers also performed RT-PCR on leaf and roots of B73 maize and the results confirm Lynx analysis results that there is no leaf specific AMT in maize, although ZMAMT1, 2, 7 (SEQ ID NOS: 14, 16 and 26) are expressed in leaves and roots.

Example 8

CTP Predictions in Chloroplast Outer Envelope Proteins

Initial cTP prediction couldn't detect a putative cTP in most of the higher plant AMTs analyzed. The chloroplast localized AMT (if any) has to be in the outer envelope of the chloroplast. In order to determine whether proteins localized in outer envelop of the chloroplast have any predicted cTP, researchers searched the NCBI database using 'thloroplast outer envelop/membrane' as keyword and identified the 14, 14 and 5 proteins from *Arabidopsis*, rice and maize, respectively that are suppose to be localized in outer envelop of chloroplast. Some of these are well characterized proteins and known to be localized in the outer membrane of chloroplast. ChloroP program was used to identify putative cTP in these 33 candidate proteins and interestingly none of these proteins show any putative cTP with high probability. These observations suggest that either a cTP is not required or not identified/characterized for these proteins so far. This also suggests that although most of the AMTs don't have a predicted cTP but some of them might be localized in the chloroplast outer membrane.

Example 9

Isolation and Characterization of AtAMT1;2 (SEQ ID NO: 4) T-DNA Mutant

In cTP prediction analyses, AtAMT1;2 (SEQ ID NO: 4) possess a putative cTP. For functional analyses of AtAMT1;2 (SEQ ID NO: 4) and to determine it's role in N-assimilation, researchers identified a T-DNA mutant line (SM_3.15680) from the *Arabidopsis* T-DNA mutant data base. The T-DNA mutant line was ordered from ABRC and the homozygous plants were subjected to molecular analyses. In this mutant line T-DNA was inserted in c-terminal of AtAMT1;2 (SEQ ID NO: 4) gene (FIG. 3A). Genomic PCRs using AtAMT1;2 (SEQ ID NO: 4) gene and T-DNA specific primers show that T-DNA is indeed inserted in the AtAMT1;2 (SEQ ID NO: 4) (FIG. 3B). AtAMT1;2 (SEQ ID NO: 4) gene specific primers flanking the T-DNA insert couldn't amplify any DNA region in mutant plants where as an expected PCR product was detected in wild type plant (FIG. 4B, upper panel). Similarly, genomic PCR with AtAMT1;2 (SEQ ID NO: 4) specific forward primer and T-DNA specific reverse primers amplify an expected product in mutant lines and nothing in wild type plants as expected (FIG. 4B, lower panel). Saturated RT-PCRs (35 cycles) analyses couldn't detect a full length atamt1;2 mRNA in mutant (FIG. 4C, upper panel) suggesting that AtAMT1;2 (SEQ ID NO: 4) is completely knocked out in this T-DNA mutant. Actin control RT-PCR worked fine in both mutant and wild type plants (FIG. 3C, lower panel).

Example 10

Generation and Molecular Characterization of AtAMT1;2 (SEQ ID NO: 4) RNAi Lines In addition to T-DNA mutant, another parallel approach was also undertaken for functional analysis of AtAMT1;2 (SEQ ID NO: 4). A RNAi vector containing ZM-UBI promoter driven RNAi cassette consisting of inverted repeats of AtAMT1;2 (SEQ ID NO: 4) specific DNA regions and ADH intron as a spacer was constructed. Wild type *Arabidopsis* (Columbia-0) was transformed with this RNAi vector by *Agrobacterium* mediated 'floral-dip' method. Several transgenic lines were identified by selecting the T0 seeds for herbicide resistance in soil. Molecular characterization of these transgenic lines were performed by RT-PCR for Actin, AtAMT1;2 (SEQ ID NO: 4) RNAi cassette, endogenous AtAMT1;2 (SEQ ID NO: 4) and presence of gDNA in RNA preparations. Several lines with a significant reduced levels of AtAMT1;2 (SEQ ID NO: 4) were identified after molecular analysis.

Example 11

Sub-Cellular Localization and Regulation of Expression of AtAMT1;2 (SEQ ID NO: 4)

cTP prediction analyses indicate that AtAMT1;2 (SEQ ID NO: 4) contains a putative predicted cTP (but with only 55% probability). The objectives of the experiments described in this example are to determine sub-cellular localization and regulation of expression the endogenous AtAMT1;2 (SEQ ID NO: 4). The coding sequence of AtAMT1;2 (SEQ ID NO: 4) was tagged with green fluorescent protein (GFP) as an in-frame C-terminal fusion under the control of AtAMT1;2 (SEQ ID NO: 4) native promoter and a strong constitutive (ZM-UBI) promoter. *Arabidopsis* transgenic lines were generated and analyzed for GFP expression by confocal microscopy. Analyses show that AtAMT1;2:GFP is localized in the plasma membrane of endodermis and the cortex in roots.

Example 12

Knock-Out/Knock-Down of Zm-AMTs in Maize

ESTs corresponding to all seven maize AMTs were identified and annotated and full length cDNA clones were obtained. Experiments to knock-out/knock-down of all these individual ZmAMTs by RNAi are in progress. TUSC screening experiments were used to identify knock-out mutants for three leaf expressed ZmAMT1 (SEQ ID NO: 14), ZmAMT2 (SEQ ID NO: 16) and ZmAMT7 (SEQ ID NO: 26).

Example 13

Knock-Out/Knock-Down of Multiple AtAMTs with Single RNAi Vector in *Arabidopsis*

Six AMT genes are present in *Arabidopsis* genome. Hence, it is very likely that due to functional redundancy one might need to manipulate the expression of multiple AMTs simultaneously. The DNA sequence of all these AMTs was analyzed and identified the high homology regions among them. For example there is such a stretch of ~200 bp among AtAMT1;2 (SEQ ID NO: 4), AtAMT1 (SEQ ID NO: 2), AMT1;3 (SEQ ID NO: 6), At3g24290 (SEQ ID NO: 10) and At4g28700 (SEQ ID NO: 12) where as AMT2 (SEQ ID NO: 8) stood independent (FIG. 4). These regions were amplified (bold and underlined in FIG. 4) by PCR from AtAMT1;2 (SEQ ID NO: 4) and AtAMT2 (SEQ ID NO: 8) and performed a multi-way ligation to make an inverted repeat using ADH-intron as a spacer. The RNAi cassette of these hybrid inverted repeats is driven by a constitutive or root-specific or leaf-specific promter. Several transgenic Arabidopsis lines were generated for these three constructs. Molecular analyses of these lines were performed by genomic and RT-PCR. Several lines were identified that expressed significantly reduced levels of multiple AtAMTs. These transgenic lines show a methyl ammonium (ammonium analog toxic to plants) tolerant/better growth phenotype as compared to wild type control when grown on MS media supplemented with 10-30 mM of methyl ammonium. These results indicate multiple AMTs were knocked-down in these lines, resulting in reduced uptake of methyl ammonium.

Example 14

Knock-Out/Knock-Down of Multiple ZmAMTs in Maize by Single RNAi Vector

In maize at least 7 AMT like genes were identified and at least 3 of them are expressed both in leaf and root (see, Example 2). For improving NUE by reducing loss of ammonia by volatilization, one might have to knock-out/knock-down multiple AMTs. Detailed analyses of all 7 maize AMTs were performed to identify the DNA regions showing high homology among different ZmAMTs. This analysis reveals that ZmAMT1 (SEQ ID NO: 14) and ZmAMT5 (SEQ ID NO: 22), ZmAMT3 (SEQ ID NO: 18) and ZmAMT4 (SEQ ID NO: 20) and ZmAMT2 (SEQ ID NO: 16), ZmAMT6 (SEQ ID NO: 24) and ZmAMT7 (SEQ ID NO: 26) form three separate groups and there is a very high homology in stretches of DNA sequences with in each group (FIG. 5). Three DNA fragments (bold and underlined in FIG. 5) from ZmAMT 1, 4 and 7 (SEQ ID NOS: 14, 20 and 26) representing each of the different groups were amplified by PCR. Multi-way ligations were performed to make inverted repeats with hybrid of these 3 fragments and ADH intron as a spacer to facilitate the formation of stem-loop structure. This hybrid RNAi cassette of 'ZmAMT1 (SEQ ID NO: 14):ZmAMT4 (SEQ ID NO: 20):ZmAMT7 (SEQ ID NO: 26)' inverted repeats was driven by Zm-UBI promoter and a leaf-specific promoter. MOPAT driven by Zm-UBI promoter was used as herbicide resistance marker for selected. In addition to that RFP driven by a pericarp specific promoter LTP2 was also used to sort out the transgenic seeds (red) from there segregating non-transgenic seeds. Transgenic lines for the constructs were generated, with molecular analyses of the TO events performed by genomic and RT-PCR. Several lines with significantly reduced expression of individual/multiple ZmAMTs have been identified and characterized.

Example 15

Variants of AMT Sequences

A. Variant Nucleotide Sequences of AMT That Do Not Alter the Encoded Amino Acid Sequence The AMT nucleotide sequences are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequence of the variants are altered, the amino acid sequence encoded by the open reading frames do not change.

B. Variant Amino Acid Sequences of AMT Polypeptides

Variant amino acid sequences of the AMT polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using the protein alignment set forth in FIG. 2, an appropriate amino acid can be changed. Once the targeted amino acid is identified, the procedure outlined in the following section C is followed. Variants having about 70%, 75%, 80%, 85%, 90% and 95% nucleic acid sequence identity are generated using this method.

C. Additional Variant Amino Acid Sequences of AMT Polypeptides

In this example, artificial protein sequences are created having 80%, 85%, 90% and 95% identity relative to the reference protein sequence. This latter effort requires identifying conserved and variable regions from the alignment set forth in FIG. 2 and then the judicious application of an amino acid substitutions table. These parts will be discussed in more detail below.

Largely, the determination of which amino acid sequences are altered is made based on the conserved regions among AMT protein or among the other AMT polypeptides. Based on the sequence alignment, the various regions of the AMT polypeptide that can likely be altered are represented in lower case letters, while the conserved regions are represented by capital letters. It is recognized that conservative substitutions can be made in the conserved regions below without altering function. In addition, one of skill will understand that functional variants of the AMT sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 2.

TABLE 2

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |

TABLE 2-continued

Substitution Table

| Amino Acid | Strongly Similar and Optimal Substitution | Rank of Order to Change | Comment |
|---|---|---|---|
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the AMT polypeptides are generating having about 80%, 85%, 90%, and 95% amino acid identity to the starting unaltered ORF nucleotide sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79 or 81.

Example 16

Over-Expression of AMTs in Plants to Improve NUE

The over-expression of AMTs has been demonstrated with strong constitutively or organ-specific (e.g. in roots) expression which improves ammonium uptake (especially in low ammonium soils in anaerobic conditions typical of rice field conditions) leading to improved nitrogen use efficiency. In other plants, such as maize, typically most of the N is absorbed by roots in the form of nitrate, the available source in most soil, however there is still a considerable proportion of N available as ammonium. Over-expression of AMTs in these conditions leads to improved nitrogen utilization. Since nitrate needs to be reduced to ammonium by an energy expensive reaction before it is assimilated, ammonium is a preferable source of N when available to the plant.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. An isolated polynucleotide selected from the group consisting of:
   a. the polynucleotide of SEQ ID NO:15, wherein the polynucleotide encodes a polypeptide that functions as an ammonium transporter;
   b. a polynucleotide encoding the polypeptide of SEQ ID NO:16; and
   c. a polynucleotide which is fully complementary to the polynucleotide of (a) or (b).

2. A recombinant expression cassette comprising the polynucleotide of claim 1, wherein the polynucleotide is operably linked in sense orientation to a promoter.

3. A host cell comprising the expression cassette of claim 2.

4. A transgenic plant comprising the recombinant expression cassette of claim 2.

5. The transgenic plant of claim 4, wherein said plant is a monocot.

6. The transgenic plant of claim 4, wherein said plant is a dicot.

7. The transgenic plant of claim 4, wherein said plant is selected from the group consisting of: maize, soybean, sunflower, sorghum, canola, wheat, alfalfa, cotton, rice, barley, millet, peanut, switchgrass, myscanthus, triticale and cocoa.

8. A transgenic seed from the transgenic plant of claim 4.

* * * * *

SEQUENCE LISTING

<160> NUMBER OF SEQ ID NOS: 82

<210> SEQ ID NO 1
<211> LENGTH: 1736
<212> TYPE: DNA
<213> ORGANISM: Arabidopsis thaliana

<400> SEQUENCE: 1

```
agcctctctg tttcatcttc ttctctaaac tctcaacatg tcttgctcgg ccaccgatct      60
cgctgtcctg ttgggtccta atgccacggc ggcggccaac tacatctgtg gccagttagg     120
cgacgtcaac aacaaattta tcgacaccgc tttcgctata gacaacactt accttctctt     180
ctccgcctac cttgtcttct ctatgcagct tggcttcgct atgctctgtg ccggttccgt     240
gagagccaag aatactatga acatcatgct taccaacgtc cttgacgctg cagccggtgg     300
tctcttctat tatctgtttg gctacgcctt tgcctttgga tctccgtcca atggtttcat     360
cggtaaacac tactttggtc tcaaagacat ccccacggcc tctgctgact actccaactt     420
tctctaccaa tgggcctttg caatcgctgc ggctggaatc acaagtggct cgatcgctga     480
acggacacag ttcgtggctt acctaatcta ttcctctttc ttaaccgggt tgtttaccc      540 ggtcgtctct cactggttct ggtcagttga tggatgggcc agcccgttcc gtaccgatgg     600
agatttgctt ttcagcaccg gagcgataga tttcgctggg tccggtgttg ttcatatggt     660
cggaggtatc gctggactct ggggtgcgct catcgaaggt ccacgacttg gccggttcga     720
```

-continued

```
taacggaggc cgtgccatcg ctcttcgtgg ccactcggcg tcacttgttg tccttggaac    780
attcctcctc tggtttggat ggtacggatt taacccgggt tccttcaaca agatcctagt    840
cacgtacgag acaggcacat acaacggcca gtggagcgcg gtcggacgga cagctgtcac    900
aacaacgtta gctggctgca ccgcggcgct gacaacccta tttgggaaac gtctactctc    960
gggacattgg aacgtcactg atgtatgcaa cggcctcctc ggagggtttg cagccataac   1020
tggtggctgc tctgtcgttg agccatgggc tgcgatcatc tgcgggttcg tggcggccct   1080
agtcctcctc ggatgcaaca agctcgctga aagctcaaa tacgacgacc tcttgaggc    1140
agcacaacta cacggtggtt gcggtgcgtg gggactaata ttcacggctc tcttcgctca   1200
agaaaagtac ttgaaccaga tttacggcaa caaacccgga aggccacacg gtttgtttat   1260
gggcggtgga ggaaaactac ttggagctca gctgattcag atcattgtga tcacgggttg   1320
ggtaagtgcg accatgggga cacttttctt catcctcaag aaaatgaaat tgttgcggat   1380
atcgtccgag gatgagatgg ccggtatgga tatgaccagg cacggtggtt ttgcttatat   1440
gtactttgat gatgatgagt ctcacaaagc cattcagctt aggagagttg agccacgatc   1500
tccttctcct tctggtgcta atactacacc tactccggtt tgatttggat ttttactttt   1560
attctctatt ttctagagta ttatttaaa tgatgttttg tgatacttaa atattgtttt    1620
ggatattttt ttgcatttca gtaatgtttt agatgtacag tttcatgggg ttgtgatgat   1680
aatatctatg tggtcatttg tgttctcttt ggagtttttt ctataacgct ttttc        1736
```

<210> SEQ ID NO 2
<211> LENGTH: 501
<212> TYPE: PRT
<213> ORGANISM: Arabidopsis thaliana

<400> SEQUENCE: 2

```
Met Ser Cys Ser Ala Thr Asp Leu Ala Val Leu Leu Gly Pro Asn Ala
 1               5                  10                  15

Thr Ala Ala Ala Asn Tyr Ile Cys Gly Gln Leu Gly Asp Val Asn Asn
            20                  25                  30

Lys Phe Ile Asp Thr Ala Phe Ala Ile Asp Asn Thr Tyr Leu Leu Phe
        35                  40                  45

Ser Ala Tyr Leu Val Phe Ser Met Gln Leu Gly Phe Ala Met Leu Cys
    50                  55                  60

Ala Gly Ser Val Arg Ala Lys Asn Thr Met Asn Ile Met Leu Thr Asn
65                  70                  75                  80

Val Leu Asp Ala Ala Ala Gly Gly Leu Phe Tyr Tyr Leu Phe Gly Tyr
                85                  90                  95

Ala Phe Ala Phe Gly Ser Pro Ser Asn Gly Phe Ile Gly Lys His Tyr
            100                 105                 110

Phe Gly Leu Lys Asp Ile Pro Thr Ala Ser Ala Asp Tyr Ser Asn Phe
        115                 120                 125

Leu Tyr Gln Trp Ala Phe Ala Ile Ala Ala Gly Ile Thr Ser Gly
    130                 135                 140

Ser Ile Ala Glu Arg Thr Gln Phe Val Ala Tyr Leu Ile Tyr Ser Ser
145                 150                 155                 160

Phe Leu Thr Gly Phe Val Tyr Pro Val Val Ser His Trp Phe Trp Ser
                165                 170                 175

Val Asp Gly Trp Ala Ser Pro Phe Arg Thr Asp Gly Asp Leu Leu Phe
            180                 185                 190

Ser Thr Gly Ala Ile Asp Phe Ala Gly Ser Gly Val Val His Met Val
```

195                 200                 205
Gly Gly Ile Ala Gly Leu Trp Gly Ala Leu Ile Glu Gly Pro Arg Leu
            210                 215                 220
Gly Arg Phe Asp Asn Gly Gly Arg Ala Ile Ala Leu Arg Gly His Ser
225                 230                 235                 240
Ala Ser Leu Val Val Leu Gly Thr Phe Leu Leu Trp Phe Gly Trp Tyr
                245                 250                 255
Gly Phe Asn Pro Gly Ser Phe Asn Lys Ile Leu Val Thr Tyr Glu Thr
            260                 265                 270
Gly Thr Tyr Asn Gly Gln Trp Ser Ala Val Gly Arg Thr Ala Val Thr
        275                 280                 285
Thr Thr Leu Ala Gly Cys Thr Ala Ala Leu Thr Thr Leu Phe Gly Lys
    290                 295                 300
Arg Leu Leu Ser Gly His Trp Asn Val Thr Asp Val Cys Asn Gly Leu
305                 310                 315                 320
Leu Gly Gly Phe Ala Ala Ile Thr Gly Gly Cys Ser Val Val Glu Pro
                325                 330                 335
Trp Ala Ala Ile Ile Cys Gly Phe Val Ala Ala Leu Val Leu Leu Gly
            340                 345                 350
Cys Asn Lys Leu Ala Glu Lys Leu Lys Tyr Asp Asp Pro Leu Glu Ala
        355                 360                 365
Ala Gln Leu His Gly Gly Cys Gly Ala Trp Gly Leu Ile Phe Thr Ala
    370                 375                 380
Leu Phe Ala Gln Glu Lys Tyr Leu Asn Gln Ile Tyr Gly Asn Lys Pro
385                 390                 395                 400
Gly Arg Pro His Gly Leu Phe Met Gly Gly Gly Lys Leu Leu Gly
                405                 410                 415
Ala Gln Leu Ile Gln Ile Ile Val Ile Thr Gly Trp Val Ser Ala Thr
            420                 425                 430
Met Gly Thr Leu Phe Phe Ile Leu Lys Lys Met Lys Leu Leu Arg Ile
        435                 440                 445
Ser Ser Glu Asp Glu Met Ala Gly Met Asp Met Thr Arg His Gly Gly
    450                 455                 460
Phe Ala Tyr Met Tyr Phe Asp Asp Asp Glu Ser His Lys Ala Ile Gln
465                 470                 475                 480
Leu Arg Arg Val Glu Pro Arg Ser Pro Ser Pro Ser Gly Ala Asn Thr
                485                 490                 495
Thr Pro Thr Pro Val
            500

<210> SEQ ID NO 3
<211> LENGTH: 1860
<212> TYPE: DNA
<213> ORGANISM: Arabidopsis thaliana

<400> SEQUENCE: 3
acttaagcaa acacgttcca caatcaagta ccctctctct atctctccct ccctccctct     60
ccaccatgga caccgcaacc accacatgct ctgccgtaga tctatctgcc ctcctatcct    120
cttcttctaa ctcaacatct tccctcgccg cggcaacctt tttatgttcc caaatttcaa    180
acatctccaa caaactctcc gacacaactt atgccgtcga caacacgtat ctcctcttct    240
ccgcctacct tgtctttgcc atgcagctcg gtttcgctat gctttgtgct ggatcagtcc    300
gagccaagaa cactatgaac atcatgctta ccaatgtcct tgatgctgcc gctggagcca    360
tctcttacta cctcttcgga ttcgcattcg cctttggtac accttccaac ggattcatcg    420

-continued

```
gtcgccacca tagcttcttc gctttaagct cttaccctga acgccccggc tccgacttca    480 gcttttttcct ctaccaatgg gcttttgcca tagccgcggc cggaatcact agcggttcca    540
tcgccgagcg aacgcaattc gttgcttacc ttatctactc tactttcttg accggttttg    600
tttacccgac agtctcgcac tggttctggt caagtgatgg atgggctagc gcgtcccggt    660
ctgacaacaa tctcttgttt ggctcaggtg ctattgattt cgcaggttca ggagttgttc    720
acatggtagg tggaattgcc ggtttatgtg gagcgttagt tgaaggacca agaataggta    780
gatttgaccg tcaggccgg tccgtggctt tacgtggtca cagtgcatcc cttgtcgtgc    840
ttggtacctt cttgttgtgg tttggatggt atgggtttaa ccctggttcc ttttaacca    900 ttcttaaagg ctacgacaag tctcggccat attatggtca atggagcgct gtaggtcgca    960
ccgcggtcac cacaacgctt tctggctgca ccgctgcgtt gactactcta ttcagtaaac    1020
ggcttttagc aggtcattgg aacgttattg acgtatgcaa cggacttcta ggcggctttg    1080
cagctataac ctccggatgt gccgtggtgg agccgtgggc tgctatagta tgtggctttg    1140
tggcatcatg ggttttaatc ggatttaact tgcttgccaa gaaacttaaa tatgatgacc    1200
cactcgaggc tgctcagctc cacggtggat gtggagcatg gggattaatc tttaccgggc    1260
tgttcgcaag gaaagaatac gttaacgaga tttactccgg tgataggcct acggactgt     1320 tcatgggcgg gggaggaaaa ctgctcgccg cgcagatcgt tcagattatt gtgatcgttg    1380
ggtgggtgac ggtaactatg ggaccgttgt tttatgggtt acataagatg aatcttttga    1440
ggatatcagc agaagatgag atggcaggaa tggacatgac acgtcatgga ggatttgctt    1500
acgcatacaa tgacgaagac gacgtgtcga ctaaaccatg gggtcatttc gctggaagag    1560
tggagcctac aagccggagc tcgactccta caccgacctt gactgtttga tactttgatt    1620
ggagaattga gtggtcccaa acgagtcagt tttaatgtgg tgaagacaag agttcgggca    1680
ccaaacatgt tggacgcatc tttgtgtatt attggtcttc ttcttcttct ttttttttct    1740
cttggttatc gctctgttgt ggacagatag tgtggaactg ttaacaataa catgatcagt    1800
atgtcttttt aattaaagtg aacgtttggt atcaaaatta acattggaa tttgagcggt     1860
```

<210> SEQ ID NO 4
<211> LENGTH: 514
<212> TYPE: PRT
<213> ORGANISM: Arabidopsis thaliana

<400> SEQUENCE: 4

```
Met Asp Thr Ala Thr Thr Thr Cys Ser Ala Val Asp Leu Ser Ala Leu
 1               5                  10                  15

Leu Ser Ser Ser Ser Asn Ser Thr Ser Ser Leu Ala Ala Ala Thr Phe
            20                  25                  30

Leu Cys Ser Gln Ile Ser Asn Ile Ser Asn Lys Leu Ser Asp Thr Thr
        35                  40                  45

Tyr Ala Val Asp Asn Thr Tyr Leu Leu Phe Ser Ala Tyr Leu Val Phe
    50                  55                  60

Ala Met Gln Leu Gly Phe Ala Met Leu Cys Ala Gly Ser Val Arg Ala
65                  70                  75                  80

Lys Asn Thr Met Asn Ile Met Leu Thr Asn Val Leu Asp Ala Ala Ala
                85                  90                  95

Gly Ala Ile Ser Tyr Tyr Leu Phe Gly Phe Ala Phe Ala Phe Gly Thr
            100                 105                 110

Pro Ser Asn Gly Phe Ile Gly Arg His His Ser Phe Phe Ala Leu Ser
        115                 120                 125
```

Ser Tyr Pro Glu Arg Pro Gly Ser Asp Phe Ser Phe Leu Tyr Gln
    130                 135                 140

Trp Ala Phe Ala Ile Ala Ala Gly Ile Thr Ser Gly Ser Ile Ala
145                 150                 155                 160

Glu Arg Thr Gln Phe Val Ala Tyr Leu Ile Tyr Ser Thr Phe Leu Thr
                165                 170                 175

Gly Phe Val Tyr Pro Thr Val Ser His Trp Phe Trp Ser Ser Asp Gly
                180                 185                 190

Trp Ala Ser Ala Ser Arg Ser Asp Asn Asn Leu Leu Phe Gly Ser Gly
                195                 200                 205

Ala Ile Asp Phe Ala Gly Ser Gly Val Val His Met Val Gly Gly Ile
    210                 215                 220

Ala Gly Leu Cys Gly Ala Leu Val Glu Gly Pro Arg Ile Gly Arg Phe
225                 230                 235                 240

Asp Arg Ser Gly Arg Ser Val Ala Leu Arg Gly His Ser Ala Ser Leu
                245                 250                 255

Val Val Leu Gly Thr Phe Leu Leu Trp Phe Gly Trp Tyr Gly Phe Asn
                260                 265                 270

Pro Gly Ser Phe Leu Thr Ile Leu Lys Gly Tyr Asp Lys Ser Arg Pro
                275                 280                 285

Tyr Tyr Gly Gln Trp Ser Ala Val Gly Arg Thr Ala Val Thr Thr Thr
    290                 295                 300

Leu Ser Gly Cys Thr Ala Ala Leu Thr Thr Leu Phe Ser Lys Arg Leu
305                 310                 315                 320

Leu Ala Gly His Trp Asn Val Ile Asp Val Cys Asn Gly Leu Leu Gly
                325                 330                 335

Gly Phe Ala Ala Ile Thr Ser Gly Cys Ala Val Val Glu Pro Trp Ala
                340                 345                 350

Ala Ile Val Cys Gly Phe Val Ala Ser Trp Val Leu Ile Gly Phe Asn
                355                 360                 365

Leu Leu Ala Lys Lys Leu Lys Tyr Asp Asp Pro Leu Glu Ala Ala Gln
    370                 375                 380

Leu His Gly Gly Cys Gly Ala Trp Gly Leu Ile Phe Thr Gly Leu Phe
385                 390                 395                 400

Ala Arg Lys Glu Tyr Val Asn Glu Ile Tyr Ser Gly Asp Arg Pro Tyr
                405                 410                 415

Gly Leu Phe Met Gly Gly Gly Lys Leu Leu Ala Ala Gln Ile Val
                420                 425                 430

Gln Ile Ile Val Ile Val Gly Trp Val Thr Val Thr Met Gly Pro Leu
    435                 440                 445

Phe Tyr Gly Leu His Lys Met Asn Leu Leu Arg Ile Ser Ala Glu Asp
    450                 455                 460

Glu Met Ala Gly Met Asp Met Thr Arg His Gly Gly Phe Ala Tyr Ala
465                 470                 475                 480

Tyr Asn Asp Glu Asp Asp Val Ser Thr Lys Pro Trp Gly His Phe Ala
                485                 490                 495

Gly Arg Val Glu Pro Thr Ser Arg Ser Ser Thr Pro Thr Pro Thr Leu
                500                 505                 510

Thr Val

<210> SEQ ID NO 5
<211> LENGTH: 1758
<212> TYPE: DNA
<213> ORGANISM: Arabidopsis thaliana

<400> SEQUENCE: 5

```
gtatctctct ttctctctct cagctctctc aaacatgtca ggagcaataa catgctctgc    60
ggccgatctc gccaccctac ttggcccaa cgccacggcg gcggccgact acatttgcgg    120
ccaattaggc accgttaaca acaagttcac cgatgcagcc ttcgccatag acaacaccta    180
cctcctcttc tctgcctacc ttgtcttcgc catgcagctc ggcttcgcta tgctttgtgc    240
tggttctgtt agagccaaga atacgatgaa catcatgctt accaatgtcc ttgacgctgc    300
agccggagga ctcttctact atctctttgg ttacgccttt gccttggag atcctccga     360
agggttcatt ggaagacaca actttgctct tagagacttt ccgactccca cagctgatta   420
ctctttcttc ctctaccaat gggcgttcgc aatcgcggcc gctggaatca caagtggttc   480
gatcgcagag aggactcagt tcgtggctta cttgatatac tcttctttct taaccggatt   540
tgtttacccg gttgtctctc actggttttg gtccccggat ggatgggcca gtcccttttcg  600
ttcagcggat gatcgtttgt ttagcaccgg agccattgac tttgctggct ccggtgttgt   660
tcacatggtt ggtggcatag caggtttatg gggtgctctt attgaaggtc ctcgtcgtgg   720
tcggttcgag aaaggtggtc gcgctattgc tctgcgcggc cactctgcct cgctagtagt   780
cttaggaacc ttcctcctat ggtttggatg gtatggttc aaccccggtt ccttcactaa    840
gatactcgtt ccgtataatt ctggttccaa ctacggccaa tggagcggaa tcggccgtac   900
agcggttaac accacactct caggatgcac agcagctcta accacactct ttggtaaacg   960
tctcctatca ggccactgga acgtaacgga cgtttgcaac gggttactcg gtgggtttgc  1020
ggccataacc gcaggttgct ccgtcgtaga gccatgggca gcgattgtgt gcggcttcat  1080
ggcttctgtc gtccttatcg gatgcaacaa gctcgcggag cttgtacaat atgatgatcc  1140
actcgaggca gcccaactac atggagggtg tggcgcgtgg gggttgatat cgtaggatt   1200
gtttgccaaa gagaagtatc taaacgaggt ttatggcgcc accccgggaa ggccatatgg  1260
actatttatg ggcggaggag ggaagctgtt gggagcacaa ttggttcaaa tacttgtgat  1320
tgtaggatgg ttagtgcca caatgggaac actcttcttc atcctcaaaa ggctcaatct   1380
gcttaggatc tcggagcagc atgaaatgca agggatggat atgacacgtc acggtggctt  1440
tgcttatatc taccatgata atgatgatga gtctcataga gtggatcctg gatctccttt  1500
cccctcgatca gctactcctc ctcgcgttta attttcaact ttttggtaat ttattaccgt  1560
ttaagtattg tttgggtttt ggttttgaaa tataaatatt tggatgtttt ggtttgtttt  1620
aagtgaccta tcgtctttt gtgttataa gtgtttagt ttatgttttt ttttttttc      1680
ttgaattta attttacatg cctcggctaa tgtttatgct atttcttaga aatttatata    1740
tacaactttt ggtgatcc                                                 1758
```

<210> SEQ ID NO 6
<211> LENGTH: 498
<212> TYPE: PRT
<213> ORGANISM: Arabidopsis thaliana

<400> SEQUENCE: 6

```
Met Ser Gly Ala Ile Thr Cys Ser Ala Ala Asp Leu Ala Thr Leu Leu
 1               5                  10                  15

Gly Pro Asn Ala Thr Ala Ala Asp Tyr Ile Cys Gly Gln Leu Gly
            20                  25                  30

Thr Val Asn Asn Lys Phe Thr Asp Ala Ala Phe Ala Ile Asp Asn Thr
        35                  40                  45
```

```
Tyr Leu Leu Phe Ser Ala Tyr Leu Val Phe Ala Met Gln Leu Gly Phe
 50                  55                  60

Ala Met Leu Cys Ala Gly Ser Val Arg Ala Lys Asn Thr Met Asn Ile
 65                  70                  75                  80

Met Leu Thr Asn Val Leu Asp Ala Ala Gly Gly Leu Phe Tyr Tyr
                 85                  90                  95

Leu Phe Gly Tyr Ala Phe Ala Phe Gly Gly Ser Ser Glu Gly Phe Ile
                100                 105                 110

Gly Arg His Asn Phe Ala Leu Arg Asp Phe Pro Thr Pro Thr Ala Asp
            115                 120                 125

Tyr Ser Phe Phe Leu Tyr Gln Trp Ala Phe Ala Ile Ala Ala Ala Gly
            130                 135                 140

Ile Thr Ser Gly Ser Ile Ala Glu Arg Thr Gln Phe Val Ala Tyr Leu
145                 150                 155                 160

Ile Tyr Ser Ser Phe Leu Thr Gly Phe Val Tyr Pro Val Val Ser His
                165                 170                 175

Trp Phe Trp Ser Pro Asp Gly Trp Ala Ser Pro Phe Arg Ser Ala Asp
                180                 185                 190

Asp Arg Leu Phe Ser Thr Gly Ala Ile Asp Phe Ala Gly Ser Gly Val
            195                 200                 205

Val His Met Val Gly Gly Ile Ala Gly Leu Trp Gly Ala Leu Ile Glu
            210                 215                 220

Gly Pro Arg Arg Gly Arg Phe Glu Lys Gly Gly Arg Ala Ile Ala Leu
225                 230                 235                 240

Arg Gly His Ser Ala Ser Leu Val Val Leu Gly Thr Phe Leu Leu Trp
                245                 250                 255

Phe Gly Trp Tyr Gly Phe Asn Pro Gly Ser Phe Thr Lys Ile Leu Val
                260                 265                 270

Pro Tyr Asn Ser Gly Ser Asn Tyr Gly Gln Trp Ser Gly Ile Gly Arg
            275                 280                 285

Thr Ala Val Asn Thr Thr Leu Ser Gly Cys Thr Ala Ala Leu Thr Thr
            290                 295                 300

Leu Phe Gly Lys Arg Leu Leu Ser Gly His Trp Asn Val Thr Asp Val
305                 310                 315                 320

Cys Asn Gly Leu Leu Gly Gly Phe Ala Ala Ile Thr Ala Gly Cys Ser
                325                 330                 335

Val Val Glu Pro Trp Ala Ala Ile Val Cys Gly Phe Met Ala Ser Val
            340                 345                 350

Val Leu Ile Gly Cys Asn Lys Leu Ala Glu Leu Val Gln Tyr Asp Asp
            355                 360                 365

Pro Leu Glu Ala Ala Gln Leu His Gly Gly Cys Gly Ala Trp Gly Leu
370                 375                 380

Ile Phe Val Gly Leu Phe Ala Lys Glu Lys Tyr Leu Asn Glu Val Tyr
385                 390                 395                 400

Gly Ala Thr Pro Gly Arg Pro Tyr Gly Leu Phe Met Gly Gly Gly Gly
                405                 410                 415

Lys Leu Leu Gly Ala Gln Leu Val Gln Ile Leu Val Ile Val Gly Trp
            420                 425                 430

Val Ser Ala Thr Met Gly Thr Leu Phe Phe Ile Leu Lys Arg Leu Asn
            435                 440                 445

Leu Leu Arg Ile Ser Glu Gln His Glu Met Gln Gly Met Asp Met Thr
450                 455                 460

Arg His Gly Gly Phe Ala Tyr Ile Tyr His Asp Asn Asp Asp Glu Ser
465                 470                 475                 480
```

His Arg Val Asp Pro Gly Ser Pro Phe Pro Arg Ser Ala Thr Pro Pro
            485                 490                 495

Arg Val

<210> SEQ ID NO 7
<211> LENGTH: 1428
<212> TYPE: DNA
<213> ORGANISM: Arabidopsis thaliana

<400> SEQUENCE: 7

| | | | | | |
|---|---|---|---|---|---|
| atggccggag | cttacgatcc | aagcttgccg | gaggttcctg | aatggctcaa | caaaggagac | 60 |
| aacgcgtggc | agctcacggc | agcgactctg | gttggtctac | agagtatgcc | aggtcttgtt | 120 |
| atcctctatg | cctccatcgt | caagaagaaa | tgggctgtga | attcagcttt | tatggctctt | 180 |
| tacgctttcg | ccgccgttct | tctctgttgg | gttctcctct | gttacaaaat | ggcttttgga | 240 |
| gaagagcttt | tgccgttttg | gggcaaaggt | ggtccagctt | tcgaccaagg | ataccttaag | 300 |
| ggacaagcaa | agatcccaaa | tagtaatgtg | gcggcgccgt | attttccgat | ggcgacgttg | 360 |
| gtgtattttc | agttcacatt | cgcggcgata | cgacgatac | ttgtggcggg | atctgtgttg | 420 |
| gggaggatga | atattaaagc | atggatggct | tttgtgccat | tgtggttgat | ctttagctac | 480 |
| acagttggag | cttatagtat | atggggaggt | gggtttctgt | atcagtgggg | agttattgat | 540 |
| tattccggcg | gttatgttat | tcatctctcc | tccggtgttg | ccggtttcgt | cgctgcttac | 600 |
| tgggtaggac | caaggcctaa | ggctgacaga | gagagattcc | caccgaacaa | tgttcttcta | 660 |
| atgcttgctg | gagctggact | tttatggatg | ggatggtccg | gttttaacgg | tggtgctcct | 720 |
| tacgcggcca | acttaacctc | ctctatcgcc | gtgttaaaca | ccaacctctc | ggccgccaca | 780 |
| agcctccttg | tatggactac | acttgatgtc | atcttctttg | gcaaaccttc | tgtcatcgga | 840 |
| gcaattcaag | gcatggttac | tggcttagcc | ggcgtcactc | ccggagcagg | tttgatccaa | 900 |
| acatgggcag | ctataataat | tggagtagtc | tcaggaacag | ctccatgggc | tctctatgatg | 960 |
| atcattcaca | gaaatccgc | tctccttcaa | aaggtggatg | atacattagc | ggtgttttac | 1020 |
| acacacgccg | tggctggttt | acttggtgga | ataatgacag | ggttgtttgc | acaccctgat | 1080 |
| ctctgcgttt | tggtacttcc | tctcccagcg | accagaggag | cttttctacgg | tggcaatggc | 1140 |
| ggcaaacagc | ttttgaaaca | gttggctgga | gctgccttca | ttgccgtctg | gaatgtggtg | 1200 |
| tcgactacta | tcattctact | cgctattagg | gtgttcatac | cattgagaat | ggctgaggaa | 1260 |
| gagctcggga | ttgagacga | cgcagcacat | ggggaagaag | cttatgctct | ttggggagat | 1320 |
| ggagagaagt | ttgatgctac | aaggcatgtg | caacagtttg | agagagatca | agaagctgct | 1380 |
| catccttctt | atgttcatgg | tgctagaggt | gtcaccattg | ttctatga | | 1428 |

<210> SEQ ID NO 8
<211> LENGTH: 475
<212> TYPE: PRT
<213> ORGANISM: Arabidopsis thaliana

<400> SEQUENCE: 8

Met Ala Gly Ala Tyr Asp Pro Ser Leu Pro Glu Val Pro Glu Trp Leu
1               5                   10                  15

Asn Lys Gly Asp Asn Ala Trp Gln Leu Thr Ala Ala Thr Leu Val Gly
            20                  25                  30

Leu Gln Ser Met Pro Gly Leu Val Ile Leu Tyr Ala Ser Ile Val Lys
        35                  40                  45

Lys Lys Trp Ala Val Asn Ser Ala Phe Met Ala Leu Tyr Ala Phe Ala

```
            50                  55                  60
Ala Val Leu Leu Cys Trp Val Leu Leu Cys Tyr Lys Met Ala Phe Gly
65                  70                  75                  80

Glu Glu Leu Leu Pro Phe Trp Gly Lys Gly Pro Ala Phe Asp Gln
                85                  90                  95

Gly Tyr Leu Lys Gly Gln Ala Lys Ile Pro Asn Ser Asn Val Ala Ala
                    100                 105                 110

Pro Tyr Phe Pro Met Ala Thr Leu Val Tyr Gln Phe Thr Phe Ala
                115                 120                 125

Ala Ile Thr Thr Ile Leu Val Ala Gly Ser Val Leu Gly Arg Met Asn
130                 135                 140

Ile Lys Ala Trp Met Ala Phe Val Pro Leu Trp Leu Ile Phe Ser Tyr
145                 150                 155                 160

Thr Val Gly Ala Tyr Ser Ile Trp Gly Gly Phe Leu Tyr Gln Trp
                    165                 170                 175

Gly Val Ile Asp Tyr Ser Gly Gly Tyr Val Ile His Leu Ser Ser Gly
                180                 185                 190

Val Ala Gly Phe Val Ala Ala Tyr Trp Val Gly Pro Arg Pro Lys Ala
                195                 200                 205

Asp Arg Glu Arg Phe Pro Pro Asn Asn Val Leu Leu Met Leu Ala Gly
210                 215                 220

Ala Gly Leu Leu Trp Met Gly Trp Ser Gly Phe Asn Gly Gly Ala Pro
225                 230                 235                 240

Tyr Ala Ala Asn Leu Thr Ser Ser Ile Ala Val Leu Asn Thr Asn Leu
                    245                 250                 255

Ser Ala Ala Thr Ser Leu Leu Val Trp Thr Thr Leu Asp Val Ile Phe
                260                 265                 270

Phe Gly Lys Pro Ser Val Ile Gly Ala Ile Gln Gly Met Val Thr Gly
                275                 280                 285

Leu Ala Gly Val Thr Pro Gly Ala Gly Leu Ile Gln Thr Trp Ala Ala
                290                 295                 300

Ile Ile Ile Gly Val Val Ser Gly Thr Ala Pro Trp Ala Ser Met Met
305                 310                 315                 320

Ile Ile His Lys Lys Ser Ala Leu Leu Gln Lys Val Asp Asp Thr Leu
                    325                 330                 335

Ala Val Phe Tyr Thr His Ala Val Ala Gly Leu Leu Gly Gly Ile Met
                340                 345                 350

Thr Gly Leu Phe Ala His Pro Asp Leu Cys Val Leu Val Leu Pro Leu
                355                 360                 365

Pro Ala Thr Arg Gly Ala Phe Tyr Gly Gly Asn Gly Gly Lys Gln Leu
370                 375                 380

Leu Lys Gln Leu Ala Gly Ala Ala Phe Ile Ala Val Trp Asn Val Val
385                 390                 395                 400

Ser Thr Thr Ile Ile Leu Leu Ala Ile Arg Val Phe Ile Pro Leu Arg
                    405                 410                 415

Met Ala Glu Glu Glu Leu Gly Ile Gly Asp Asp Ala Ala His Gly Glu
                420                 425                 430

Glu Ala Tyr Ala Leu Trp Gly Asp Gly Glu Lys Phe Asp Ala Thr Arg
                435                 440                 445

His Val Gln Gln Phe Glu Arg Asp Gln Glu Ala Ala His Pro Ser Tyr
                450                 455                 460

Val His Gly Ala Arg Gly Val Thr Ile Val Leu
465                 470                 475
```

<210> SEQ ID NO 9
<211> LENGTH: 1491
<212> TYPE: DNA
<213> ORGANISM: Arabidopsis thaliana

<400> SEQUENCE: 9

```
atgtcaggag ctattacttg ctctgcggct gatctctcag ccctactcgg cccaaatgcc      60
acggcagcgg ctgactacat ttgcggccag ttgggttccg ttaacaacaa gtttaccgat     120
gcagcctacg ctatagacaa cacgtacctc ctcttctctg cctatcttgt ctttgcgatg     180
cagctcggct tcgctatgct ttgtgctggc tccgttagag ctaagaacac gatgaacatc     240
atgctcacta atgtccttga tgctgcagcc ggaggactct tctactacct ctttggttat     300
gcatttgcct ttggtgaatc ctccgatgga ttcattggaa gacacaactt tggtcttcaa     360
aactttccga ctctcaccct ggattactcc ttcttcctct accaatgggc gtttgcaatc     420
gcagccgctg gaatcaccag cggctccatt gccgagagga ctaagttcgt ggcgtatttg     480
atatactctt ctttttttgac cgggtttgtt tacccagttg tctctcactg gttctggtct     540
ccggatggat gggctagtcc cttccgttca gaagaccgtt tgtttggcac tggagccatc     600
gactttgctg gtcaggtgt tgttcacatg gttggtggta tcgcaggatt atggggtgcc     660
cttattgaag gccctcggat tggtcggttt cctgatgggg gtcatgctat tgctctgcga     720
ggccactctg cctcactcgt cgtcttaggg accttccttc tctggtttgg ttggtacggg     780
ttcaaccctg gttccttcac caagatactc attccctaca attctggttc aactatggc     840
caatggagtg gaataggccg caccgcggtt acaactacac tctcgggatg cacagcggct     900
ctaaccacac tcttcggaaa acgtctccta tcaggccact ggaacgtaac tgacgtttgc     960
aacgggttac tcggagggtt tgcggccata acggcaggtt gctctgtggt tgatccatgg    1020
gcagcgatcg tatgtggctt cgtggcttcc ctcgtcctta tcggatgcaa caagctcgca    1080
gagctcttaa aatatgacga tccacttgag gccgcacaac tacacggagg tgtggtgct    1140
tggggtttga tatttgtagg actgtttgca aaagagaagt atataaatga ggttacggc    1200
gcgagcccag gaaggcacta cgggctatct atgggcggag agggaagct attgggagca    1260
caactggttc aaataattgt gattgttgga tgggttagtg ccacaatggg aacactcttc    1320
ttcatcctca aaaagctcaa tttgcttagg atctcggagc agcatgaaat gcgaggaatg    1380
gatttagcag gtcatggtgg ttttgcttat atctaccatg ataatgatga tgattccatt    1440
ggagtgcctg gatctccagt acctcgtgcg cctaaccctc cagccgtttg a             1491
```

<210> SEQ ID NO 10
<211> LENGTH: 496
<212> TYPE: PRT
<213> ORGANISM: Arabidopsis thaliana

<400> SEQUENCE: 10

```
Met Ser Gly Ala Ile Thr Cys Ser Ala Ala Asp Leu Ser Ala Leu Leu
  1               5                  10                  15

Gly Pro Asn Ala Thr Ala Ala Asp Tyr Ile Cys Gly Gln Leu Gly
             20                  25                  30

Ser Val Asn Asn Lys Phe Thr Asp Ala Ala Tyr Ala Ile Asp Asn Thr
         35                  40                  45

Tyr Leu Leu Phe Ser Ala Tyr Leu Val Phe Ala Met Gln Leu Gly Phe
     50                  55                  60

Ala Met Leu Cys Ala Gly Ser Val Arg Ala Lys Asn Thr Met Asn Ile
 65                  70                  75                  80
```

-continued

Met Leu Thr Asn Val Leu Asp Ala Ala Gly Gly Leu Phe Tyr Tyr
                85                  90                  95

Leu Phe Gly Tyr Ala Phe Ala Phe Gly Glu Ser Ser Asp Gly Phe Ile
            100                 105                 110

Gly Arg His Asn Phe Gly Leu Gln Asn Phe Pro Thr Leu Thr Ser Asp
        115                 120                 125

Tyr Ser Phe Phe Leu Tyr Gln Trp Ala Phe Ala Ile Ala Ala Ala Gly
    130                 135                 140

Ile Thr Ser Gly Ser Ile Ala Glu Arg Thr Lys Phe Val Ala Tyr Leu
145                 150                 155                 160

Ile Tyr Ser Ser Phe Leu Thr Gly Phe Val Tyr Pro Val Val Ser His
                165                 170                 175

Trp Phe Trp Ser Pro Asp Gly Trp Ala Ser Pro Phe Arg Ser Glu Asp
            180                 185                 190

Arg Leu Phe Gly Thr Gly Ala Ile Asp Phe Ala Gly Ser Gly Val Val
        195                 200                 205

His Met Val Gly Gly Ile Ala Gly Leu Trp Gly Ala Leu Ile Glu Gly
    210                 215                 220

Pro Arg Ile Gly Arg Phe Pro Asp Gly His Ala Ile Ala Leu Arg
225                 230                 235                 240

Gly His Ser Ala Ser Leu Val Val Leu Gly Thr Phe Leu Leu Trp Phe
                245                 250                 255

Gly Trp Tyr Gly Phe Asn Pro Gly Ser Phe Thr Lys Ile Leu Ile Pro
            260                 265                 270

Tyr Asn Ser Gly Ser Asn Tyr Gly Gln Trp Ser Gly Ile Gly Arg Thr
        275                 280                 285

Ala Val Thr Thr Thr Leu Ser Gly Cys Thr Ala Ala Leu Thr Thr Leu
    290                 295                 300

Phe Gly Lys Arg Leu Leu Ser Gly His Trp Asn Val Thr Asp Val Cys
305                 310                 315                 320

Asn Gly Leu Leu Gly Gly Phe Ala Ala Ile Thr Ala Gly Cys Ser Val
                325                 330                 335

Val Asp Pro Trp Ala Ala Ile Val Cys Gly Phe Val Ala Ser Leu Val
            340                 345                 350

Leu Ile Gly Cys Asn Lys Leu Ala Glu Leu Leu Lys Tyr Asp Asp Pro
        355                 360                 365

Leu Glu Ala Ala Gln Leu His Gly Gly Cys Gly Ala Trp Gly Leu Ile
    370                 375                 380

Phe Val Gly Leu Phe Ala Lys Glu Lys Tyr Ile Asn Glu Val Tyr Gly
385                 390                 395                 400

Ala Ser Pro Gly Arg His Tyr Gly Leu Phe Met Gly Gly Gly Lys
                405                 410                 415

Leu Leu Gly Ala Gln Leu Val Gln Ile Ile Val Ile Gly Trp Val
            420                 425                 430

Ser Ala Thr Met Gly Thr Leu Phe Phe Ile Leu Lys Lys Leu Asn Leu
        435                 440                 445

Leu Arg Ile Ser Glu Gln His Glu Met Arg Gly Met Asp Leu Ala Gly
    450                 455                 460

His Gly Gly Phe Ala Tyr Ile Tyr His Asp Asn Asp Asp Ser Ile
465                 470                 475                 480

Gly Val Pro Gly Ser Pro Val Pro Arg Ala Pro Asn Pro Pro Ala Val
                485                 490                 495

<210> SEQ ID NO 11
<211> LENGTH: 1515
<212> TYPE: DNA
<213> ORGANISM: Arabidopsis thaliana

<400> SEQUENCE: 11

```
atggcgtcgg ctctctcttg ctctgcctct gatctgattc cattactatc aggtggagcc      60
aacgccaccg cagcagcagc cgccgctgaa tacatctgcg ggagattcga cacagtcgcc     120
gggaaattca ctgatgcggc ttacgcaatc gacaacactt accttctctt ctctgcttac     180
ctcgttttcg cgatgcagct cggtttcgcc atgctctgtg ccggatccgt acgtgcaaaa     240
aacacgatga acattatgct cacgaacgtc atcgacgctg cagccggagg tctcttctat     300
tatctcttcg gtttcgcttt tgcttttgga tctccttcta atggattcat cggaaaacat     360
ttctttggaa tgtatgattt tcctcaacct acgtttgatt atccttattt tctatatcaa     420
tggactttcg ctatcgccgc cgctggaatc acgagtggtt cgatagcgga gaggactcag     480
ttcgttgcgt atttgatcta ttcttctttc ttgacgggtc ttgtttaccc gattgtgtcg     540
cattggtttt ggtcttctga tggttgggcg tctccggcta gatctgagaa ccttctgttt     600
caatcaggtg tgattgattt cgctggctct ggtgttgttc atatggttgg tggtattgct     660
ggtttatggg gagctttaat tgaaggacct aggattggtc ggtttggagt tggggtaaa      720
ccggttacgt gcgtggtca tagtgctacg ttggttgttc ttggaacgtt tttgttatgg     780
ttcggatggt acgggtttaa cccgggctcg tttgcaacta ttttaaggc gtatggggag     840
actccaggga gctcgtttta cggacaatgg agcgcagttg ggagaaccgc ggtaacaact     900
acgttagctg gttgcacggc ggcgttaacg actctgtttg ggaaaagact tattgatggg     960
tattggaatg taactgatgt ttgcaatggt ttgttaggcg ggtttgcggc tataactagc    1020
ggatgttcgg ttgtggaacc gtgggctgcg cttgtatgtg ggtttgtagc cgcatgggtg    1080
ctgatgggat gcaatagact agcggaaaag ctccaatttg atgatccgtt ggaagcggct    1140
cagcttcacg gtggttgtgg tgcgtggggg attatttca ccgggttgtt cgcggagaaa    1200
agatacattg ccgagatctt tggaggcgac ccgaataggc ctttcggatt gctaatggga    1260
ggaggaggta ggttgcttgc ggcgcacgtc gttcagattt tggtgattac gggttgggtt    1320
agtgtgacaa tggggactct gttttttatt ttgcataagc tgaaactgtt gaggataccg    1380
gcggaggatg agatagctgg ggtggatccg acgagtcacg gagggttggc ttatatgtac    1440
acagaagatg agattaggaa tgggatcatg gttaggagag tgggtggtga taatgatccc    1500
aatgtaggtg tttga                                                    1515
```

<210> SEQ ID NO 12
<211> LENGTH: 504
<212> TYPE: PRT
<213> ORGANISM: Arabidopsis thaliana

<400> SEQUENCE: 12

```
Met Ala Ser Ala Leu Ser Cys Ser Ala Ser Asp Leu Ile Pro Leu Leu
 1               5                  10                  15

Ser Gly Gly Ala Asn Ala Thr Ala Ala Ala Ala Ala Glu Tyr Ile
            20                  25                  30

Cys Gly Arg Phe Asp Thr Val Ala Gly Lys Phe Thr Asp Ala Ala Tyr
        35                  40                  45

Ala Ile Asp Asn Thr Tyr Leu Leu Phe Ser Ala Tyr Leu Val Phe Ala
    50                  55                  60

Met Gln Leu Gly Phe Ala Met Leu Cys Ala Gly Ser Val Arg Ala Lys
```

```
              65                  70                  75                  80
Asn Thr Met Asn Ile Met Leu Thr Asn Val Ile Asp Ala Ala Ala Gly
                        85                  90                  95
Gly Leu Phe Tyr Tyr Leu Phe Gly Phe Ala Phe Ala Phe Gly Ser Pro
                    100                 105                 110
Ser Asn Gly Phe Ile Gly Lys His Phe Phe Gly Met Tyr Asp Phe Pro
                    115                 120                 125
Gln Pro Thr Phe Asp Tyr Pro Tyr Phe Leu Tyr Gln Trp Thr Phe Ala
                    130                 135                 140
Ile Ala Ala Ala Gly Ile Thr Ser Gly Ser Ile Ala Glu Arg Thr Gln
145                 150                 155                 160
Phe Val Ala Tyr Leu Ile Tyr Ser Ser Phe Leu Thr Gly Leu Val Tyr
                    165                 170                 175
Pro Ile Val Ser His Trp Phe Trp Ser Asp Gly Trp Ala Ser Pro
                    180                 185                 190
Ala Arg Ser Glu Asn Leu Leu Phe Gln Ser Gly Val Ile Asp Phe Ala
                    195                 200                 205
Gly Ser Gly Val Val His Met Val Gly Gly Ile Ala Gly Leu Trp Gly
                    210                 215                 220
Ala Leu Ile Glu Gly Pro Arg Ile Gly Arg Phe Gly Val Gly Gly Lys
225                 230                 235                 240
Pro Val Thr Leu Arg Gly His Ser Ala Thr Leu Val Val Leu Gly Thr
                    245                 250                 255
Phe Leu Leu Trp Phe Gly Trp Tyr Gly Phe Asn Pro Gly Ser Phe Ala
                    260                 265                 270
Thr Ile Phe Lys Ala Tyr Gly Glu Thr Pro Gly Ser Ser Phe Tyr Gly
                    275                 280                 285
Gln Trp Ser Ala Val Gly Arg Thr Ala Val Thr Thr Thr Leu Ala Gly
                    290                 295                 300
Cys Thr Ala Ala Leu Thr Thr Leu Phe Gly Lys Arg Leu Ile Asp Gly
305                 310                 315                 320
Tyr Trp Asn Val Thr Asp Val Cys Asn Gly Leu Leu Gly Gly Phe Ala
                    325                 330                 335
Ala Ile Thr Ser Gly Cys Ser Val Val Glu Pro Trp Ala Ala Leu Val
                    340                 345                 350
Cys Gly Phe Val Ala Ala Trp Val Leu Met Gly Cys Asn Arg Leu Ala
                    355                 360                 365
Glu Lys Leu Gln Phe Asp Asp Pro Leu Glu Ala Ala Gln Leu His Gly
                    370                 375                 380
Gly Cys Gly Ala Trp Gly Ile Ile Phe Thr Gly Leu Phe Ala Glu Lys
385                 390                 395                 400
Arg Tyr Ile Ala Glu Ile Phe Gly Gly Asp Pro Asn Arg Pro Phe Gly
                    405                 410                 415
Leu Leu Met Gly Gly Gly Arg Leu Leu Ala Ala His Val Val Gln
                    420                 425                 430
Ile Leu Val Ile Thr Gly Trp Val Ser Val Thr Met Gly Thr Leu Phe
                    435                 440                 445
Phe Ile Leu His Lys Leu Lys Leu Leu Arg Ile Pro Ala Glu Asp Glu
                    450                 455                 460
Ile Ala Gly Val Asp Pro Thr Ser His Gly Gly Leu Ala Tyr Met Tyr
465                 470                 475                 480
Thr Glu Asp Glu Ile Arg Asn Gly Ile Met Val Arg Val Gly Gly
                    485                 490                 495
```

Asp Asn Asp Pro Asn Val Gly Val
            500

<210> SEQ ID NO 13
<211> LENGTH: 2073
<212> TYPE: DNA
<213> ORGANISM: Zea mays

<400> SEQUENCE: 13

| | | | | | |
|---|---|---|---|---|---|
| atccgcgcca | caccctccca | atcccctccc | cctcgcgtat | ccacactttt | cacacgcgac | 60 |
| gccggagaga | cagagcgcgc | gcgcgcccga | aagatgtcga | cgtgcgcggc | ggacctggcg | 120 |
| ccgctgctcg | gcccggcggc | ggcgaacgcc | acggactacc | tgtgcgggca | gttcgcggac | 180 |
| acggcctccg | cggtggacgc | cacgtacctg | ctcttctcgg | cctacctcgt | gttcgccatg | 240 |
| cagctcggct | tcgccatgct | gtgcgccggc | tccgtccgcg | ccaagaacac | catgaacatc | 300 |
| atgctcacca | acgtgctcga | cgccgccgcg | ggggcgctct | tctactacct | cttcggcttc | 360 |
| gccttcgcct | tcggcacgcc | ctccaacggc | ttcatcggca | agcagttctt | cgggctcaag | 420 |
| cacctgccca | ggaccggctt | cgactacgac | ttcttcctct | accagtgggc | cttcgccatc | 480 |
| gccgccgcgg | gcatcacgtc | gggctccatc | gccgagcgga | cccagttcgt | cgcctacctc | 540 |
| atctactccg | cgttcctgac | ggggttcgtc | taccccgtgg | tgtcgcactg | gttctggtcc | 600 |
| gccgacggct | gggccggcgc | cagccgcacg | tccggcccgc | tgctcttcgg | gtccggcgtc | 660 |
| atcgacttcg | ccggctccgg | cgtcgtccac | atggtcggcg | gcatcgcggg | gctgtggggc | 720 |
| gcgctcatcg | agggcccccg | catcgggcgc | ttcgaccacg | ccggccgctc | cgtggcgctc | 780 |
| aagggccaca | gcgcgtcgct | cgtggtgctc | ggcaccttcc | tgctgtggtt | cggctggtac | 840 |
| gggttcaacc | ccgggtcctt | caccaccatc | ctcaagtcgt | acggcccgc | cgggaccgtc | 900 |
| cacgggcagt | ggtcggccgt | gggccgcacc | gccgtcacca | ccaccctcgc | cggcagcgtc | 960 |
| gccgcgctca | ccacgctgtt | cgggaagcgg | ctccagacgg | gccactggaa | cgtggtggac | 1020 |
| gtctgcaacg | gcctcctcgg | cgggttcgcg | gccatcacgg | ccgggtgcag | cgtggtggag | 1080 |
| ccgtgggcgg | ccgtcatctg | cgggttcgtg | tccgcgtggg | tgctcatcgg | cgccaacgcc | 1140 |
| ctcgcggcgc | gcttcaggtt | cgacgacccg | ctggaggcgg | cgcagctgca | cggcgggtgt | 1200 |
| ggcgcctggg | gcgtcctctt | cacggggctc | ttcgcgaggc | gaaagtacgt | ggaggagatc | 1260 |
| tacggcgccg | ggaggcccta | cgggctgttc | atgggcggcg | gcgggaagct | cctcgccgcg | 1320 |
| cagatcatcc | agatcctggt | gatcgccggg | tgggtgagct | gcaccatggg | cccgctcttc | 1380 |
| tacgcgctca | agaagctggg | cctgctgcgc | atctcggccg | acgacgagat | gtccggcatg | 1440 |
| gacctgaccc | ggcacggcgg | cttcgcctac | gtctaccacg | acgaggaccc | tggcgacaag | 1500 |
| gccggggttg | gtgggttcat | gctcaagtcc | gcgcagaacc | gtgtcgagcc | ggcggcggcg | 1560 |
| gtggcggcgg | cgaccagcag | ccaggtgtaa | aaaaaaatc | aggagcaaat | tgaaaccgag | 1620 |
| ctgaagttac | gtgcttgcct | ttttcagtat | gttgtcgcgt | atcacgtttg | aggtggatcg | 1680 |
| tatctgccgg | tcagtacgca | gtgtttgggc | aaatacttgg | ctacttggga | gtcgcaagaa | 1740 |
| attgtgtaaa | ttatatagag | gaggatggcg | acgaagcacg | catgtgttac | gtagttgggg | 1800 |
| tttgtgtgca | catggtggtg | ggcaggggct | aggagagggt | ttatctttag | gttattttcg | 1860 |
| tagtggaatg | aatcttatga | tcggatatcc | atcgtcggaa | ggtgtggcgg | gctgctggtc | 1920 |
| aagataggtg | gcttctatga | ctatgagggt | tgaaacaaca | agtggacgat | tctgtcctgt | 1980 |
| ggtcactgct | catcatccaa | tctagcggct | ttgacggtcg | tgccttttta | gtatcaataa | 2040 |
| tattattcca | agtttaaaaa | aaaaaaaaaa | aaa | | | 2073 |

<210> SEQ ID NO 14
<211> LENGTH: 498
<212> TYPE: PRT
<213> ORGANISM: Zea mays

<400> SEQUENCE: 14

```
Met Ser Thr Cys Ala Ala Asp Leu Ala Pro Leu Leu Gly Pro Ala Ala
 1               5                  10                  15

Ala Asn Ala Thr Asp Tyr Leu Cys Gly Gln Phe Ala Asp Thr Ala Ser
             20                  25                  30

Ala Val Asp Ala Thr Tyr Leu Leu Phe Ser Ala Tyr Leu Val Phe Ala
         35                  40                  45

Met Gln Leu Gly Phe Ala Met Leu Cys Ala Gly Ser Val Arg Ala Lys
     50                  55                  60

Asn Thr Met Asn Ile Met Leu Thr Asn Val Leu Asp Ala Ala Ala Gly
 65                  70                  75                  80

Ala Leu Phe Tyr Tyr Leu Phe Gly Phe Ala Phe Ala Phe Gly Thr Pro
                 85                  90                  95

Ser Asn Gly Phe Ile Gly Lys Gln Phe Phe Gly Leu Lys His Leu Pro
            100                 105                 110

Arg Thr Gly Phe Asp Tyr Asp Phe Phe Leu Tyr Gln Trp Ala Phe Ala
        115                 120                 125

Ile Ala Ala Ala Gly Ile Thr Ser Gly Ser Ile Ala Glu Arg Thr Gln
    130                 135                 140

Phe Val Ala Tyr Leu Ile Tyr Ser Ala Phe Leu Thr Gly Phe Val Tyr
145                 150                 155                 160

Pro Val Val Ser His Trp Phe Trp Ser Ala Asp Gly Trp Ala Gly Ala
                165                 170                 175

Ser Arg Thr Ser Gly Pro Leu Leu Phe Gly Ser Gly Val Ile Asp Phe
            180                 185                 190

Ala Gly Ser Gly Val Val His Met Val Gly Gly Ile Ala Gly Leu Trp
        195                 200                 205

Gly Ala Leu Ile Glu Gly Pro Arg Ile Gly Arg Phe Asp His Ala Gly
    210                 215                 220

Arg Ser Val Ala Leu Lys Gly His Ser Ala Ser Leu Val Val Leu Gly
225                 230                 235                 240

Thr Phe Leu Leu Trp Phe Gly Trp Tyr Gly Phe Asn Pro Gly Ser Phe
                245                 250                 255

Thr Thr Ile Leu Lys Ser Tyr Gly Pro Ala Gly Thr Val His Gly Gln
            260                 265                 270

Trp Ser Ala Val Gly Arg Thr Ala Val Thr Thr Thr Leu Ala Gly Ser
        275                 280                 285

Val Ala Ala Leu Thr Thr Leu Phe Gly Lys Arg Leu Gln Thr Gly His
    290                 295                 300

Trp Asn Val Val Asp Val Cys Asn Gly Leu Leu Gly Gly Phe Ala Ala
305                 310                 315                 320

Ile Thr Ala Gly Cys Ser Val Val Glu Pro Trp Ala Ala Val Ile Cys
                325                 330                 335

Gly Phe Val Ser Ala Trp Val Leu Ile Gly Ala Asn Ala Leu Ala Ala
            340                 345                 350

Arg Phe Arg Phe Asp Asp Pro Leu Glu Ala Gln Leu His Gly Gly
        355                 360                 365

Cys Gly Ala Trp Gly Val Leu Phe Thr Gly Leu Phe Ala Arg Arg Lys
    370                 375                 380
```

| | | | | | | | | | | |
|---|---|---|---|---|---|---|---|---|---|---|
|Tyr|Val|Glu|Glu|Ile|Tyr|Gly|Ala|Gly|Arg|Pro|Tyr|Gly|Leu|Phe|Met|
|385| | | |390| | | |395| | | | |400| | |

Gly Gly Gly Gly Lys Leu Leu Ala Ala Gln Ile Ile Gln Ile Leu Val
            405                 410                 415

Ile Ala Gly Trp Val Ser Cys Thr Met Gly Pro Leu Phe Tyr Ala Leu
        420                 425                 430

Lys Lys Leu Gly Leu Leu Arg Ile Ser Ala Asp Asp Glu Met Ser Gly
        435                 440                 445

Met Asp Leu Thr Arg His Gly Gly Phe Ala Tyr Val Tyr His Asp Glu
        450                 455                 460

Asp Pro Gly Asp Lys Ala Gly Val Gly Gly Phe Met Leu Lys Ser Ala
465                 470                 475                 480

Gln Asn Arg Val Glu Pro Ala Ala Ala Val Ala Ala Thr Ser Ser
            485                 490                 495

Gln Val

```
<210> SEQ ID NO 15
<211> LENGTH: 1597
<212> TYPE: DNA
<213> ORGANISM: Zea mays

<400> SEQUENCE: 15
```

| | |
|---|---|
|tttgctagcg aagtccagta gtgcaactca cccttcctg gtcctgctgc tccgccctct|60|
|ccacctagct accactccct tagagcgcca ctgccaagcc atggcgggag aggggcggc|120|
|ctaccagagc tcgtcggcgt cgccggactg gctgaacaag ggcgacaatg cgtggcagat|180|
|gacgtccgcg acgctggtgg gcctgcagag catgcccggg ctggtgatcc tgtacggcag|240|
|catcgtgaag aagaagtggg ccatcaactc ggcgttcatg gcgctgtacg ccttcgccgc|300|
|cgtctggctc tgctgggtgg tgtgggccta caacatgtcg ttcggcgacc ggctgctgcc|360|
|cttctggggc aaggcgaggc cggcgctcgg gcagcgcttc ctggtggcgc agtcccagct|420|
|cacggccacc gccgtgcggt accgcgacgg gtcgctcgag gcggagatgc tccacccctt|480|
|ctacccggcc gccaccatgg tgtacttcca gtgcgtgttc gccagcatca ccgtcatcat|540|
|cctcgccggc tcgctgctgg gccgcatgga catcaaggcc tggatggcct tcgtcccgct|600|
|ctggatcacc ttctcctaca ccgtctccgc cttctcgctc tggggcggcg gcttcctctt|660|
|ccagtggggc gtcatcgact actccggcgg ctacgtcatc cacctctcct cgggaatcgc|720|
|cggcctcacc gccgcttact gggtagggcc aaggtcggcg tcggacaggg agcggttccc|780|
|tcccaacaac atactgctgg tgctggcggg ggcaggcctg ctgtggctcg gatggactgg|840|
|cttcaacggg ggcgacccgt actcggccaa catcgactcg tccatggcgg tgctcaacac|900|
|gcacatctgc gcctccacca gcctcctcat gtggaccctc cttgacgtct tcttcttcgg|960|
|gaagccgtcg gtgatcggtg ctgtgcaggg catgatcacc ggccttgtgt gcatcacgcc|1020|
|tggcgcaggc ctggtgcaag ggtgggcagc cattgtcatg ggaattctct caggtagcat|1080|
|ccctggtac actatgatgg tactgcacaa gaaatggtcc ttcatgcaga ggatcgacga|1140|
|caccctcggc gtattccaca cccatgcggt cgctgggctc ctcggcggcg ccactactgg|1200|
|actctttgct gagcctgtcc tctgcaacct cttcctcgcc atcccggact ccagaggtgc|1260|
|atttatggt ggtggtggat cacagtttgg gaagcagatc gctggcgcac tcttcgtcat|1320|
|tggctggaac attgttatca cttccataat ctgtgttctt attggcctag tcctgccct|1380|
|ccgaattcct gatgcacagc tgcttatcgg ggatgatgct gtacatggtg aggaggcgta|1440|

```
tgctatatgg gcagaaggcg agctcaacga tgtaacccgc caagatgaaa gcaggcatgg   1500
cagcgtcgct gtaggagtca cacaatgttt gagcatagtt cttgtaaggt tgaaagaaag   1560
aaaaatacaa gtgcatttgt ttgctaattg ctattaa                            1597
```

<210> SEQ ID NO 16
<211> LENGTH: 498
<212> TYPE: PRT
<213> ORGANISM: Zea mays

<400> SEQUENCE: 16

```
Met Ala Gly Gly Ala Ala Tyr Gln Ser Ser Ala Ser Pro Asp
 1               5                  10                  15

Trp Leu Asn Lys Gly Asp Asn Ala Trp Gln Met Thr Ser Ala Thr Leu
                20                  25                  30

Val Gly Leu Gln Ser Met Pro Gly Leu Val Ile Leu Tyr Gly Ser Ile
             35                  40                  45

Val Lys Lys Lys Trp Ala Ile Asn Ser Ala Phe Met Ala Leu Tyr Ala
 50                  55                  60

Phe Ala Ala Val Trp Leu Cys Trp Val Val Trp Ala Tyr Asn Met Ser
 65                  70                  75                  80

Phe Gly Asp Arg Leu Leu Pro Phe Trp Gly Lys Ala Arg Pro Ala Leu
                 85                  90                  95

Gly Gln Arg Phe Leu Val Ala Gln Ser Gln Leu Thr Ala Thr Ala Val
            100                 105                 110

Arg Tyr Arg Asp Gly Ser Leu Glu Ala Glu Met Leu His Pro Phe Tyr
        115                 120                 125

Pro Ala Ala Thr Met Val Tyr Phe Gln Cys Val Phe Ala Ser Ile Thr
    130                 135                 140

Val Ile Ile Leu Ala Gly Ser Leu Leu Gly Arg Met Asp Ile Lys Ala
145                 150                 155                 160

Trp Met Ala Phe Val Pro Leu Trp Ile Thr Phe Ser Tyr Thr Val Ser
                165                 170                 175

Ala Phe Ser Leu Trp Gly Gly Gly Phe Leu Phe Gln Trp Gly Val Ile
            180                 185                 190

Asp Tyr Ser Gly Gly Tyr Val Ile His Leu Ser Ser Gly Ile Ala Gly
        195                 200                 205

Leu Thr Ala Ala Tyr Trp Val Gly Pro Arg Ser Ala Ser Asp Arg Glu
    210                 215                 220

Arg Phe Pro Pro Asn Asn Ile Leu Leu Val Leu Ala Gly Ala Gly Leu
225                 230                 235                 240

Leu Trp Leu Gly Trp Thr Gly Phe Asn Gly Gly Asp Pro Tyr Ser Ala
                245                 250                 255

Asn Ile Asp Ser Ser Met Ala Val Leu Asn Thr His Ile Cys Ala Ser
            260                 265                 270

Thr Ser Leu Leu Met Trp Thr Leu Leu Asp Val Phe Phe Phe Gly Lys
        275                 280                 285

Pro Ser Val Ile Gly Ala Val Gln Gly Met Ile Thr Gly Leu Val Cys
    290                 295                 300

Ile Thr Pro Gly Ala Gly Leu Val Gln Gly Trp Ala Ala Ile Val Met
305                 310                 315                 320

Gly Ile Leu Ser Gly Ser Ile Pro Trp Tyr Thr Met Met Val Leu His
                325                 330                 335

Lys Lys Trp Ser Phe Met Gln Arg Ile Asp Asp Thr Leu Gly Val Phe
            340                 345                 350
```

His Thr His Ala Val Ala Gly Leu Leu Gly Gly Ala Thr Thr Gly Leu
        355                 360                 365
Phe Ala Glu Pro Val Leu Cys Asn Leu Phe Leu Ala Ile Pro Asp Ser
370                 375                 380
Arg Gly Ala Phe Tyr Gly Gly Gly Ser Gln Phe Gly Lys Gln Ile
385                 390                 395                 400
Ala Gly Ala Leu Phe Val Ile Gly Trp Asn Ile Val Ile Thr Ser Ile
                405                 410                 415
Ile Cys Val Leu Ile Gly Leu Val Leu Pro Leu Arg Ile Pro Asp Ala
                420                 425                 430
Gln Leu Leu Ile Gly Asp Asp Ala Val His Gly Glu Glu Ala Tyr Ala
            435                 440                 445
Ile Trp Ala Glu Gly Glu Leu Asn Asp Val Thr Arg Gln Asp Glu Ser
450                 455                 460
Arg His Gly Ser Val Ala Val Gly Val Thr Gln Cys Leu Ser Ile Val
465                 470                 475                 480
Leu Val Arg Leu Lys Glu Arg Lys Ile Gln Val His Leu Phe Ala Asn
                485                 490                 495
Cys Tyr

<210> SEQ ID NO 17
<211> LENGTH: 964
<212> TYPE: DNA
<213> ORGANISM: Zea mays

<400> SEQUENCE: 17
cgttgtccac atggtgggcg gaatcgccgg cctctggggc gccctcatcg agggcccccg    60
cattggccgg ttcgaccacg ccggccgctc ggtggcgctg cgcggccaca gcgcgtcgct   120
cgtcgtgctc ggcactttcc tgctgtggtt cggctggttc gggttcaacc ccgggtcgtt   180
cctcaccatc ctcaagagct acggcccggc cggcagcatc cacgggcagt ggtcggccgt   240
gggccgcacg gccgtgacca ccaccctcgc cggcagcacg gcggcgctca cgacgctctt   300
cgggaagagg ctccagacgg ggcactggaa cgtggtcgac gtctgcaacg gcctcctcgg   360
cggcttcgcg gcgatcaccg cgggctgctc cgtggtcgac ccctgggcgg ccatcatatg   420
cgggttcgtg tcggcgtggg tgctcatcgg gctcaacgcg ctggccgcga ggctccggtt   480
cgacgacccg ctggaggccg cgcagttgca cggtgggtgc ggcgcgtggg gggtcctctt   540
cacgggcctg ttcgcgcgca gggagtacgt ggagcagatc tacggcacgc cggggcggcc   600
gtacggcctg ttcatgggcg gcggcgggag gctgctggcc gcgaacgtgg tgatgatcct   660
ggtgatcgcc gcgtgggtta gcgtcaccat ggctccgctg ttcctggcgc tcaacaagat   720
ggggctgctc cgagtctcgg ccgaggacga gatggccggc atggaccaga gcggcacgg   780
cgggttcgcg tacgcgtacc acgacgacga cttgagcttg agcagcaggc caagggggat   840
gcagagcacg cagatcgcgg acgcggccag cggcgagttc tagtgtgttg gatcacaaat   900
ctcagtatgc tagtcctaca tcatgattgt caatagggcc atttaaaac cccttctttt   960
gggt                                                                964

<210> SEQ ID NO 18
<211> LENGTH: 293
<212> TYPE: PRT
<213> ORGANISM: Zea mays

<400> SEQUENCE: 18

Val Val His Met Val Gly Gly Ile Ala Gly Leu Trp Gly Ala Leu Ile

```
                1               5              10              15
            Glu Gly Pro Arg Ile Gly Arg Phe Asp His Ala Gly Arg Ser Val Ala
                           20                  25                  30

Leu Arg Gly His Ser Ala Ser Leu Val Val Leu Gly Thr Phe Leu Leu
                       35                  40                  45

Trp Phe Gly Trp Phe Gly Phe Asn Pro Gly Ser Phe Leu Thr Ile Leu
             50                  55                  60

Lys Ser Tyr Gly Pro Ala Gly Ser Ile His Gly Gln Trp Ser Ala Val
             65                  70                  75                  80

Gly Arg Thr Ala Val Thr Thr Thr Leu Ala Gly Ser Thr Ala Ala Leu
                           85                  90                  95

Thr Thr Leu Phe Gly Lys Arg Leu Gln Thr Gly His Trp Asn Val Val
                       100                 105                 110

Asp Val Cys Asn Gly Leu Leu Gly Gly Phe Ala Ala Ile Thr Ala Gly
                       115                 120                 125

Cys Ser Val Val Asp Pro Trp Ala Ala Ile Ile Cys Gly Phe Val Ser
                   130                 135                 140

Ala Trp Val Leu Ile Gly Leu Asn Ala Leu Ala Ala Arg Leu Arg Phe
            145                 150                 155                 160

Asp Asp Pro Leu Glu Ala Ala Gln Leu His Gly Gly Cys Gly Ala Trp
                           165                 170                 175

Gly Val Leu Phe Thr Gly Leu Phe Ala Arg Arg Glu Tyr Val Glu Gln
                       180                 185                 190

Ile Tyr Gly Thr Pro Gly Arg Pro Tyr Gly Leu Phe Met Gly Gly Gly
                   195                 200                 205

Gly Arg Leu Leu Ala Ala Asn Val Val Met Ile Leu Val Ile Ala Ala
                   210                 215                 220

Trp Val Ser Val Thr Met Ala Pro Leu Phe Leu Ala Leu Asn Lys Met
            225                 230                 235                 240

Gly Leu Leu Arg Val Ser Ala Glu Asp Glu Met Ala Gly Met Asp Gln
                           245                 250                 255

Thr Arg His Gly Gly Phe Ala Tyr Ala Tyr His Asp Asp Leu Ser
                       260                 265                 270

Leu Ser Ser Arg Pro Lys Gly Met Gln Ser Thr Gln Ile Ala Asp Ala
                       275                 280                 285

Ala Ser Gly Glu Phe
                       290

<210> SEQ ID NO 19
<211> LENGTH: 1587
<212> TYPE: DNA
<213> ORGANISM: Zea mays

<400> SEQUENCE: 19
atggcgacgt gcgctacgac cctcgcacct cttctgggcc cggcggcaaa cgcgacggag      60
tacctttgca accaattcgc ggacaccacg tcggcggtgg actcgacgta cctgctcttc     120
tcggcctacc tcgtcttcgc catgcagctc gggttcgcca tgctctgcgc gggctccgtc     180
cgcgccaaga acaccatgaa catcatgctc accaacgtgc tcgacgccgc cgccggcgcg     240
ctcttctact acctattcgg cttcgccttc gcgtacggga ccccgtccaa cggcttcatc     300
ggcaagcact tcttcggcct caagcggctt ccccaggtcg ggttcgacta cgacttcttc     360
ctcttccagt gggctttcgc catcgccgcc gccgggatca cgtccggctc catcgccgag     420
cgcacgcagt tcgtggcgta cctcatctac tccgccttcc tcaccggctt cgtgtacccg     480
```

-continued

```
gtggtgtccc actgggtctg gtccgccgac ggctgggcct cgccgtcacg gacgtcgggg    540
aagctcctct tcggctccgg catcatcgac ttcgccgggt ccagcgttgt ccacatggtg    600
ggcggaatcg ccggcctctg gggcgccctc atcgagggcc cccgcattgg ccggttcgac    660
cacgccggcc gctcggtggc gctgcgcggc cacagcgcgt cgctcgtcgt gctcggcact    720
ttcctgctgt ggttcggctg gttcgggttc aaccccgggt cgttcctcac catcctcaag    780
agctacggcc cggccggcag catccacggg cagtggtcgg ccgtgggccg cacggccgtg    840
accaccaccc tcgccggcag cacggcggcg ctcacgacgc tcttcgggaa gaggctccag    900
acggggcact ggaacgtggt cgacgtctgc aacggcctcc tcggcggctt cgcggcgatc    960
accgcgggct gctccgtggt cgaccccctgg gcggccatca tatgcgggtt cgtgtcggcg   1020
tgggtgctca tcgggctcaa cctggccgcg aggctccggt tcgacgaccc ccggggaggcc   1080 gcgcagttgc acggtgggtg cggcgcgtgg ggggtcctct tcacgggcct gttcgcgcgc   1140
agggagtacg tggagcagag cacgccgggg cggccgtacg gcctgttcat gggcggcggc   1200
aggctgctgg ccgcgaacgt ggtgatgatc ctggtgatcg ccgcgtgggt tagcgtcacc   1260
atggctccgc tgttcctggc gctcaacaag atggggctgc tccgagtctc ggccgaggac   1320
gagatggccg gcatggacca gacgcggcac ggcgggttcg cgtacgcgta ccacgacgac   1380
gacttgagct tgagcagcag gcccaagggg atgcgagcac gcagatcgcg gacgcggcca   1440
gcggcgagtt ctagtgtgtt ggatcacaaa tctcagtatg ctagtcctac atcatgattg   1500
tacaataaca accatgagta tactcccttc gttctaagga ttactttgac gaagtatcta   1560
gttaatttaa agataaagaa aatttaa                                       1587
```

<210> SEQ ID NO 20
<211> LENGTH: 498
<212> TYPE: PRT
<213> ORGANISM: Zea mays

<400> SEQUENCE: 20

```
Met Ala Thr Cys Ala Thr Thr Leu Ala Pro Leu Leu Gly Pro Ala Ala
 1               5                  10                  15

Asn Ala Thr Glu Tyr Leu Cys Asn Gln Phe Ala Asp Thr Thr Ser Ala
            20                  25                  30

Val Asp Ser Thr Tyr Leu Leu Phe Ser Ala Tyr Leu Val Phe Ala Met
        35                  40                  45

Gln Leu Gly Phe Ala Met Leu Cys Ala Gly Ser Val Arg Ala Lys Asn
    50                  55                  60

Thr Met Asn Ile Met Leu Thr Asn Val Leu Asp Ala Ala Gly Ala
65                  70                  75                  80

Leu Phe Tyr Tyr Leu Phe Gly Phe Ala Phe Ala Tyr Gly Thr Pro Ser
                85                  90                  95

Asn Gly Phe Ile Gly Lys His Phe Phe Gly Leu Lys Arg Leu Pro Gln
            100                 105                 110

Val Gly Phe Asp Tyr Asp Phe Phe Leu Phe Gln Trp Ala Phe Ala Ile
        115                 120                 125

Ala Ala Ala Gly Ile Thr Ser Gly Ser Ile Ala Glu Arg Thr Gln Phe
    130                 135                 140

Val Ala Tyr Leu Ile Tyr Ser Ala Phe Leu Thr Gly Phe Val Tyr Pro
145                 150                 155                 160

Val Val Ser His Trp Val Trp Ser Ala Asp Gly Trp Ala Ser Pro Ser
                165                 170                 175

Arg Thr Ser Gly Lys Leu Leu Phe Gly Ser Gly Ile Ile Asp Phe Ala
```

-continued

```
                180             185             190
Gly Ser Ser Val Val His Met Val Gly Gly Ile Ala Gly Leu Trp Gly
                    195                 200                 205
Ala Leu Ile Glu Gly Pro Arg Ile Gly Arg Phe Asp His Ala Gly Arg
                210                 215                 220
Ser Val Ala Leu Arg Gly His Ser Ala Ser Leu Val Val Leu Gly Thr
225                 230                 235                 240
Phe Leu Leu Trp Phe Gly Trp Phe Gly Phe Asn Pro Gly Ser Phe Leu
                    245                 250                 255
Thr Ile Leu Lys Ser Tyr Gly Pro Ala Gly Ser Ile His Gly Gln Trp
                260                 265                 270
Ser Ala Val Gly Arg Thr Ala Val Thr Thr Leu Ala Gly Ser Thr
                    275                 280                 285
Ala Ala Leu Thr Thr Leu Phe Gly Lys Arg Leu Gln Thr Gly His Trp
                290                 295                 300
Asn Val Val Asp Val Cys Asn Gly Leu Leu Gly Gly Phe Ala Ala Ile
305                 310                 315                 320
Thr Ala Gly Cys Ser Val Val Asp Pro Trp Ala Ala Ile Ile Cys Gly
                    325                 330                 335
Phe Val Ser Ala Trp Val Leu Ile Gly Leu Asn Leu Ala Ala Arg Leu
                340                 345                 350
Arg Phe Asp Asp Pro Arg Glu Ala Ala Gln Leu His Gly Gly Cys Gly
                    355                 360                 365
Ala Trp Gly Val Leu Phe Thr Gly Leu Phe Ala Arg Arg Glu Tyr Val
                370                 375                 380
Glu Gln Ser Thr Pro Gly Arg Pro Tyr Gly Leu Phe Met Gly Gly
385                 390                 395                 400
Arg Leu Leu Ala Ala Asn Val Val Met Ile Leu Val Ile Ala Ala Trp
                    405                 410                 415
Val Ser Val Thr Met Ala Pro Leu Phe Leu Ala Leu Asn Lys Met Gly
                420                 425                 430
Leu Leu Arg Val Ser Ala Glu Asp Glu Met Ala Gly Met Asp Gln Thr
                435                 440                 445
Arg His Gly Gly Phe Ala Tyr Ala Tyr His Asp Asp Asp Leu Ser Leu
                450                 455                 460
Ser Ser Arg Pro Lys Gly Met Arg Ala Arg Arg Ser Arg Thr Arg Pro
465                 470                 475                 480
Ala Ala Ser Ser Ser Val Leu Asp His Lys Ser Gln Tyr Ala Ser Pro
                    485                 490                 495
Thr Ser

<210> SEQ ID NO 21
<211> LENGTH: 744
<212> TYPE: DNA
<213> ORGANISM: Zea mays
<220> FEATURE:
<221> NAME/KEY: misc_feature
<222> LOCATION: 715
<223> OTHER INFORMATION: n = A,T,C or G

<400> SEQUENCE: 21
tcccaatccc ctcccccctcg cgtatccaca cttttcacac gcgacgccgg agagacagag      60
cgcgcgcgcg cccgaaagat ggcgacgtgc gcgacggacc tggcgccgct gctcggcccg     120
gcggcggcaa acgccacgga ctacctctgc aaccaattcg cggacaccac ctccgcggtg     180
gacgccacgt acctgctctt ctcggcctac ctcgtcttcg ccatgcagct cggcttcgcc     240
```

-continued

```
atgctctgcg ccggctccgt ccgcgccaag aacaccatga acatcatgct caccaacgtg    300
ctcgacgccg ccgccggcgc gctcttctac tacctattcg gcttcgcctt cgcctacggc    360
accccgtcca acggcttcat cggcaagcac ttcttcggcc tcaagcgcct gcccaagacc    420
ggcttcgact acgacttctt cctataccag tgggccttcg ccatcgccgc cgccggcatc    480
acgtccggct ccatcgccga gagcacccag ttcgtcgcct acctcatcta ctccgccttc    540
ctcaccggct tcgtgtaccc cgtggcgtcc cactgggtct ggtccgccga cggctgggcc    600
gccgccggcc gcacgtccgg cccgctgctc ttcgggtccg gcgccatcga cttcgccggc    660
tccggcgtgg tccacatggt cggcggcatc gcggggttct ggggcgcgct cgtcnagggc    720
ccccgtatcg ggcgcttcga ccac                                            744
```

```
<210> SEQ ID NO 22
<211> LENGTH: 222
<212> TYPE: PRT
<213> ORGANISM: Zea mays
<220> FEATURE:
<221> NAME/KEY: VARIANT
<222> LOCATION: 213
<223> OTHER INFORMATION: Xaa = Any Amino Acid

<400> SEQUENCE: 22
```

```
Met Ala Thr Cys Ala Thr Asp Leu Ala Pro Leu Leu Gly Pro Ala Ala
 1               5                  10                  15

Ala Asn Ala Thr Asp Tyr Leu Cys Asn Gln Phe Ala Asp Thr Thr Ser
            20                  25                  30

Ala Val Asp Ala Thr Tyr Leu Leu Phe Ser Ala Tyr Leu Val Phe Ala
        35                  40                  45

Met Gln Leu Gly Phe Ala Met Leu Cys Ala Gly Ser Val Arg Ala Lys
    50                  55                  60

Asn Thr Met Asn Ile Met Leu Thr Asn Val Leu Asp Ala Ala Ala Gly
65                  70                  75                  80

Ala Leu Phe Tyr Tyr Leu Phe Gly Phe Ala Phe Ala Tyr Gly Thr Pro
                85                  90                  95

Ser Asn Gly Phe Ile Gly Lys His Phe Phe Gly Leu Lys Arg Leu Pro
            100                 105                 110

Lys Thr Gly Phe Asp Tyr Asp Phe Phe Leu Tyr Gln Trp Ala Phe Ala
        115                 120                 125

Ile Ala Ala Gly Ile Thr Ser Gly Ser Ile Ala Glu Ser Thr Gln
    130                 135                 140

Phe Val Ala Tyr Leu Ile Tyr Ser Ala Phe Leu Thr Gly Phe Val Tyr
145                 150                 155                 160

Pro Val Ala Ser His Trp Val Trp Ser Ala Asp Gly Trp Ala Ala Ala
                165                 170                 175

Gly Arg Thr Ser Gly Pro Leu Leu Phe Gly Ser Gly Ala Ile Asp Phe
            180                 185                 190

Ala Gly Ser Gly Val Val His Met Val Gly Gly Ile Ala Gly Phe Trp
        195                 200                 205

Gly Ala Leu Val Xaa Gly Pro Arg Ile Gly Arg Phe Asp His
    210                 215                 220
```

```
<210> SEQ ID NO 23
<211> LENGTH: 1024
<212> TYPE: DNA
<213> ORGANISM: Zea mays

<400> SEQUENCE: 23
```

```
gaggtcgtcg tctctagcta gctgctaaga gagagagaga gagagaggta tacgtaggac    60
cgccggcaac tagctaacta acatgtcgtc gtcgtccggg acgacgatgc cgctggcgta   120
ccagacgtcg gcgtcgtctc ccgagtggct gaacaagggc gacaacgcgt ggcagctgac   180
ggcggcgacg ctggtggggc tgcagagctt cccgggtctg gtggtcctgt acggcggcgt   240
ggtgaagaag aagtgggccg tgaactcggc cttcatggcg ctgtacgcgt tcgcggcggt   300
gtggatctgc tgggtgacct gggcctacaa catgtccttc ggcgacaggc tgctgccgct   360
gtggggcaag gcgcggccgg cgctgagcca gggcggctg gtggggcagg ccggcctccc   420
cgccacggcg caccacttcg ccagcggcgc cctggagacc ccggccgcgg agccgctgta   480
cccgatggcc acggtggtgt acttccagtg cgtgttcgcg ccatcaccc tggtgctggt   540 cgccgggtcg ctgctggggcc ggatgagctt cgccgcgtgg atgctgttcg tgccgctctg   600
gctcaccttc tcctacaccg tcggcgcctt ctccgtatgg ggcggcgggt tcctcttcca   660
gtggggcgtc atcgactact gcggcggcta cgtcatccac ctctccgctg gcttcgccgg   720
gttcacggca gcctactggg tggggccccg ggcgcagaag gacagggaga ggttcccgcc   780
gaacaacatc ctgttcacgc tcaccggcgc gggcctgctg tggatggggt gggccggctt   840
caacggcggc gggccgtacg ccgccaacgt ggtggcgtcc atgtcggtgc tcaacaccaa   900
catctgcacc gccatgagcc tcctcgtctg gacctgcctc gacgtcgtct tcttcaagaa   960
gccctccgtc gtgggcgccg tccagggcat gatcaccgga ctcgtctgca tcacgcccgc  1020
cgca                                                                1024
```

<210> SEQ ID NO 24
<211> LENGTH: 314
<212> TYPE: PRT
<213> ORGANISM: Zea mays

<400> SEQUENCE: 24

```
Met Ser Ser Ser Ser Gly Thr Thr Met Pro Leu Ala Tyr Gln Thr Ser
 1               5                  10                  15

Ala Ser Ser Pro Glu Trp Leu Asn Lys Gly Asp Asn Ala Trp Gln Leu
            20                  25                  30

Thr Ala Ala Thr Leu Val Gly Leu Gln Ser Phe Pro Gly Leu Val Val
        35                  40                  45

Leu Tyr Gly Gly Val Val Lys Lys Lys Trp Ala Val Asn Ser Ala Phe
    50                  55                  60

Met Ala Leu Tyr Ala Phe Ala Ala Val Trp Ile Cys Trp Val Thr Trp
65                  70                  75                  80

Ala Tyr Asn Met Ser Phe Gly Asp Arg Leu Leu Pro Leu Trp Gly Lys
                85                  90                  95

Ala Arg Pro Ala Leu Ser Gln Gly Gly Leu Val Gly Gln Ala Gly Leu
            100                 105                 110

Pro Ala Thr Ala His His Phe Ala Ser Gly Ala Leu Glu Thr Pro Ala
        115                 120                 125

Ala Glu Pro Leu Tyr Pro Met Ala Thr Val Val Tyr Phe Gln Cys Val
    130                 135                 140

Phe Ala Ala Ile Thr Leu Val Leu Val Ala Gly Ser Leu Leu Gly Arg
145                 150                 155                 160

Met Ser Phe Ala Ala Trp Met Leu Phe Val Pro Leu Trp Leu Thr Phe
                165                 170                 175

Ser Tyr Thr Val Gly Ala Phe Ser Val Trp Gly Gly Gly Phe Leu Phe
            180                 185                 190
```

```
Gln Trp Gly Val Ile Asp Tyr Cys Gly Gly Tyr Val Ile His Leu Ser
            195                 200                 205
Ala Gly Phe Ala Gly Phe Thr Ala Ala Tyr Trp Val Gly Pro Arg Ala
            210                 215                 220
Gln Lys Asp Arg Glu Arg Phe Pro Pro Asn Asn Ile Leu Phe Thr Leu
225                 230                 235                 240
Thr Gly Ala Gly Leu Leu Trp Met Gly Trp Ala Gly Phe Asn Gly Gly
                245                 250                 255
Gly Pro Tyr Ala Ala Asn Val Val Ala Ser Met Ser Val Leu Asn Thr
            260                 265                 270
Asn Ile Cys Thr Ala Met Ser Leu Leu Val Trp Thr Cys Leu Asp Val
            275                 280                 285
Val Phe Phe Lys Lys Pro Ser Val Val Gly Ala Val Gln Gly Met Ile
            290                 295                 300
Thr Gly Leu Val Cys Ile Thr Pro Ala Ala
305                 310
```

<210> SEQ ID NO 25
<211> LENGTH: 1798
<212> TYPE: DNA
<213> ORGANISM: Zea mays

<400> SEQUENCE: 25

```
ttatgatcca cttggttaac tagcataatt aatcgcagat gaagcagcag ttcatgaagg      60
caggaagcag ctaaatcacc catataaatg gtcgcgcgcg ctagcatagc atagtagcga     120
tagccaccac cgatcgaagc atgatggcgg cgtcgggcgc gtacgcggcg caactcccgg     180
cggtgccgga gtggctgaac aagggcgaca acgcgtggca gctgacggcg cgacgctgg      240
tgggcatcca gtcgatgccg gggctggtgg tgctgtacgg cagcatcgtg aagaagaagt     300
gggcggtgaa ctcggcgttc atggcgctgt acgcctacgc gtcgtcgctg ctggtgtggg     360
tgctggcggg gttccgcatg gcgttcgggg agcggctgct cccgttctgg ggcaaggccg     420
gggtggcgct ctcccagggc tacctggtcc ggcgcgcctc gctctcggcg accgcgcacg     480
gggccacgcc ccgcaccgag cccctgtacc cggaggcgac gctggtgctg ttccagttcg     540
agttcgccgc catcacgctg gtgctcctgg ccggctccgt gcttggccgc atgaacatca     600
aggcctggat ggccttcacc ccgctctggc tcctcttctc ctacaccgtc ggcgccttca     660
gcatctgggg cggcggcttc ctctaccact gggggcgtcat cgactactcc ggcggatacg     720
tcatccacct ctcctccggc atcgccggct tcaccgccgc atactgggtg gcccgaggc      780
tgaagagcga ccgggagcgc ttctcccccga caacatcct gctgatgatc gcgggcggcg     840
ggctgctgtg gatgggctgg gccgggttca acggcggcgc gccctacgcc gccaacatcg     900
cggcgtccgt ggccgtgctc aacaccaacg tctccgccgc caccagcctc ctcacctgga     960
cctgcctcga cgtcatcttc ttcggcaagc cgtccgtgat cggcgccgtg cagggcatga    1020
tgacggggct cgtctgcatc accccggag cagggctggt gcagacctgg gcggcggtga    1080
tcatgggcgt gttcgcgggc agcgtgccgt ggttcaccat gatgatcctg cacaagaagg    1140
tggcgctgct gacgagggtg gacgacacgc tgggcgtctt ccacacgcac gccgtcgcgg    1200
gcctgctggg cggcgtcctc acgggcgctg gcggcacgcc ggagctgctg agatcgagt     1260
cccccgtgcc gggcctccgc ggcgcgttct acggcggagg gatccgccag gtcggcaagc    1320
agctggcggg ggccgccttc gtggtggcgt ggaacgtcgt ggtcacgtcg ctcatcctgc    1380
tggccatcgg cctgctggtg ccctgcgga tgcccgagga ccagctcatg atcggcgacg    1440
```

```
acgccgcgca cggggaggag gcctacgcgc tctggggcga cggggagaag ttcgatgcca    1500
ccaggcacga cgcggtcagg gtcgccggcg tcatggatag agaagggtcc gcggagcagc    1560
ggctatcagg gggcgtcacc attcagctgt aggcgcacgc ccgacggtcc ataagacacg    1620 acttttagc ggacattttt ttttcatggg agaagagcag tgttttaggc ttttattat    1680 tagcatgaaa ggttgtccat gtatcatatt tgcccagag cacgtagtct ctgctagttt    1740
ataaagaaat taggtcatgt attttcctc ttaatctagt ctacccgcaa catgtact    1798
```

<210> SEQ ID NO 26
<211> LENGTH: 483
<212> TYPE: PRT
<213> ORGANISM: Zea mays

<400> SEQUENCE: 26

```
Met Met Ala Ala Ser Gly Ala Tyr Ala Ala Gln Leu Pro Ala Val Pro
1               5                   10                  15

Glu Trp Leu Asn Lys Gly Asp Asn Ala Trp Gln Leu Thr Ala Ala Thr
            20                  25                  30

Leu Val Gly Ile Gln Ser Met Pro Gly Leu Val Val Leu Tyr Gly Ser
        35                  40                  45

Ile Val Lys Lys Lys Trp Ala Val Asn Ser Ala Phe Met Ala Leu Tyr
    50                  55                  60

Ala Tyr Ala Ser Ser Leu Leu Val Trp Val Leu Ala Gly Phe Arg Met
65                  70                  75                  80

Ala Phe Gly Glu Arg Leu Leu Pro Phe Trp Gly Lys Ala Gly Val Ala
                85                  90                  95

Leu Ser Gln Gly Tyr Leu Val Arg Arg Ala Ser Leu Ser Ala Thr Ala
            100                 105                 110

His Gly Ala Thr Pro Arg Thr Glu Pro Leu Tyr Pro Glu Ala Thr Leu
        115                 120                 125

Val Leu Phe Gln Phe Glu Phe Ala Ala Ile Thr Leu Val Leu Leu Ala
    130                 135                 140

Gly Ser Val Leu Gly Arg Met Asn Ile Lys Ala Trp Met Ala Phe Thr
145                 150                 155                 160

Pro Leu Trp Leu Leu Phe Ser Tyr Thr Val Gly Ala Phe Ser Ile Trp
                165                 170                 175

Gly Gly Gly Phe Leu Tyr His Trp Gly Val Ile Asp Tyr Ser Gly Gly
            180                 185                 190

Tyr Val Ile His Leu Ser Ser Gly Ile Ala Gly Phe Thr Ala Ala Tyr
        195                 200                 205

Trp Val Gly Pro Arg Leu Lys Ser Asp Arg Glu Arg Phe Ser Pro Asn
    210                 215                 220

Asn Ile Leu Leu Met Ile Ala Gly Gly Leu Leu Trp Met Gly Trp
225                 230                 235                 240

Ala Gly Phe Asn Gly Gly Ala Pro Tyr Ala Ala Asn Ile Ala Ala Ser
                245                 250                 255

Val Ala Val Leu Asn Thr Asn Val Ser Ala Ala Thr Ser Leu Leu Thr
            260                 265                 270

Trp Thr Cys Leu Asp Val Ile Phe Phe Gly Lys Pro Ser Val Ile Gly
        275                 280                 285

Ala Val Gln Gly Met Met Thr Gly Leu Val Cys Ile Thr Pro Gly Ala
    290                 295                 300

Gly Leu Val Gln Thr Trp Ala Ala Val Ile Met Gly Val Phe Ala Gly
305                 310                 315                 320
```

Ser Val Pro Trp Phe Thr Met Met Ile Leu His Lys Lys Val Ala Leu
                325                 330                 335

Leu Thr Arg Val Asp Asp Thr Leu Gly Val Phe His Thr His Ala Val
                340                 345                 350

Ala Gly Leu Leu Gly Gly Val Leu Thr Gly Leu Leu Ala Thr Pro Glu
                355                 360                 365

Leu Leu Glu Ile Glu Ser Pro Val Pro Gly Leu Arg Gly Ala Phe Tyr
                370                 375                 380

Gly Gly Gly Ile Arg Gln Val Gly Lys Gln Leu Ala Gly Ala Ala Phe
385                 390                 395                 400

Val Val Ala Trp Asn Val Val Thr Ser Leu Ile Leu Leu Ala Ile
                405                 410                 415

Gly Leu Leu Val Pro Leu Arg Met Pro Glu Asp Gln Leu Met Ile Gly
                420                 425                 430

Asp Asp Ala Ala His Gly Glu Glu Ala Tyr Ala Leu Trp Gly Asp Gly
                435                 440                 445

Glu Lys Phe Asp Ala Thr Arg His Asp Ala Val Arg Val Ala Gly Val
                450                 455                 460

Met Asp Arg Glu Gly Ser Ala Glu Gln Arg Leu Ser Gly Gly Val Thr
465                 470                 475                 480

Ile Gln Leu

<210> SEQ ID NO 27
<211> LENGTH: 330
<212> TYPE: DNA
<213> ORGANISM: Oryza sativa

<400> SEQUENCE: 27
atggtgccgg gactccgcgg cgcgttctac ggcggcggca tcaagcagat cagcaagcag    60
ctcggcggcg ctgcgtttgt gatcgcgtgg aacctcgtgg tcaccacggc catcctcctt    120
ggcatcggcc tgttcatccc gctgcggatg cccgacgagc agctcatgat cggcgacgac    180
gcggcgcacg gcgaggaggc ctacgcgttg tggggcgacg gcgagaagtt caacgcgaca    240
cagcacgacc tatcgagggg tggcggcggc ggcgacaggg acggccccga gcggctctcc    300
atcctaggcg ccagggggcgt caccatctag                                    330

<210> SEQ ID NO 28
<211> LENGTH: 186
<212> TYPE: PRT
<213> ORGANISM: Oryza sativa

<400> SEQUENCE: 28

Met Thr Pro Pro Arg Gly Pro Ser Pro Ser Thr Asn Ala Ala Arg Arg
1               5                   10                  15

Cys Arg Leu Thr Lys His Arg His Gly Arg Ala Thr Pro Ser Pro Pro
                20                  25                  30

Ile Thr Cys Ala Ser Ser Arg Arg Pro Pro Arg Glu Thr Thr Leu Pro
                35                  40                  45

His Pro Arg Cys Gly Gly Ala Pro Arg Arg His Pro His Gly Pro Pro
                50                  55                  60

Gly His Pro Gly Ala Leu Leu Pro Arg Gly Leu Glu Ser Met Val Pro
65                  70                  75                  80

Gly Leu Arg Gly Ala Phe Tyr Gly Gly Gly Ile Lys Gln Ile Ser Lys
                85                  90                  95

Gln Leu Gly Gly Ala Ala Phe Val Ile Ala Trp Asn Leu Val Val Thr

```
            100                 105                 110
Thr Ala Ile Leu Leu Gly Ile Gly Leu Phe Ile Pro Leu Arg Met Pro
        115                 120                 125

Asp Glu Gln Leu Met Ile Gly Asp Asp Ala Ala His Gly Glu Glu Ala
        130                 135                 140

Tyr Ala Leu Trp Gly Asp Gly Glu Lys Phe Asn Ala Thr Gln His Asp
145                 150                 155                 160

Leu Ser Arg Gly Gly Gly Gly Asp Arg Asp Gly Pro Glu Arg Leu
                165                 170                 175

Ser Ile Leu Gly Ala Arg Gly Val Thr Ile
            180                 185

<210> SEQ ID NO 29
<211> LENGTH: 4123
<212> TYPE: DNA
<213> ORGANISM: Oryza sativa

<400> SEQUENCE: 29
```

| | | | | | |
|---|---|---|---|---|---|
| gataaccaaa | tcggacgctg | accttgctgg | gcgaactggg | tgatcatcga | tggcgatgcg | 60 |
| agacatcacc | caactgcgtc | gggtctccac | aggagggagt | tgcttgtgct | tggtccgttt | 120 |
| ggggatcgtt | aacttaaaca | cttttacggc | gacctcgaca | cagctaaacc | ctaaactaat | 180 |
| tgcgagttag | aggcttatct | cgatctcttc | tatgcagatg | tttgacaact | tgggagtagt | 240 |
| ttactgctgg | tttggagtat | cttctcaact | tgcaatttga | ttatgtttaa | acggggagtg | 300 |
| catgattggt | gttcgcatgg | ttttaaatca | gattttataa | actgatgctc | gtcaagagac | 360 |
| gacaaggggc | cagattaggg | cagcagagta | cgtgcttgct | tgaattctga | agcatgtacg | 420 |
| aaataaatac | gatagaaatt | tcttaagaaa | ttaggtattt | ttctgacccct | ccaataagat | 480 |
| cgcgtggttg | ccagtattgc | acgtcgacta | ctacatatct | gaattcagaa | caatccaaaa | 540 |
| gagaagttac | tgttgatatt | tctacgtata | aaaaaaacat | caaatgcttt | tgtatattac | 600 |
| gaaaacagag | cgagttccct | tattgaccag | agcaaaaagg | ttgagcctga | ttaaacaaag | 660 |
| tctatgagct | tgcaggatgc | gtctcttccc | aaatttattc | acaccaaagt | cctcttcgat | 720 |
| gacatcgccc | tatttgaatc | ttatcgttga | cattgctcat | tttgctcttt | agttaatctg | 780 |
| ggcaaatgat | tggcggtggt | acttcgtgat | gtggaacagt | gaaactgttt | gtcaatctgt | 840 |
| gcgctcgagg | tacaaccagg | tcggttcctt | tgctgtttta | ttaataaaag | gagcataaat | 900 |
| tagcgccaaa | actcaagttt | taccacaaaa | aaacagtcag | ttttaataaa | gattaagcaa | 960 |
| acccttgaat | tgcactctgt | aaaatgtttg | tttcccctca | aaagctgata | aggacggacg | 1020 |
| ccgatgtgaa | acgaaacctg | ctatttcaac | catgtacata | tataatcaag | aatttcctac | 1080 |
| acgacttcca | ttttttgtgt | gttgactagt | ttctctcctt | cctggaggtg | ttaaaagagt | 1140 |
| tccgattctg | tcaaaacttc | catacagata | aatccaacct | gtcaaactac | cagctgttta | 1200 |
| attattcctt | ttcccatttt | gttatggtac | acaaaggcac | ataaccattt | acacggagca | 1260 |
| gaacagaata | ggatatgtat | taaaaaaaca | gaatggaaga | aaaatcctga | gtcacaagca | 1320 |
| cgaaaaatga | aggcgagatt | aattcgaaac | catacacatc | atcatccaca | tctcgtcgtt | 1380 |
| tgtctcacag | gacatgacac | agggagcgaa | aaccacatca | ttaatcgcgg | cctacagcta | 1440 |
| cacatccaga | ttctcccggg | atcccgaaaa | cggctcccac | cccgcaaccg | ccgcaagccg | 1500 |
| acccagccaa | aggagatccc | cctccaccac | ggaagattca | ctgcgcggtg | gccccgccg | 1560 |
| ccaaaaacca | aaacgacgaa | accattccgc | gtcatctctc | ccgcacggcg | agcgagcgag | 1620 |
| cgagcgacct | gacctcctcc | tcctataaat | ccggcgccag | cgtatctccc | caacctccca | 1680 |

```
cgcccaatcc tgccgccgtt tcagcagctc tagtttgaac gagggatcgt agagaggagg    1740
gtttggtgag ggagggagga agatggcgac gtgcgcggcg gacctggcgc cgctgctggg    1800
gccggtggcg gcgaacgcga cggactacct gtgcaaccgg ttcgccgaca cgacgtcggc    1860
ggtggacgcg acgtacctgc tcttctcggc gtacctcgtg ttcgccatgc agctcgggtt    1920
cgcgatgctc tgcgccgggt cggtgcgggc caagaacacg atgaacatca tgctcaccaa    1980
cgtgctcgac gccgcggccg gggcgctctt ctactacctc ttcggcttcg ccttcgcctt    2040
cggcacgccg tccaacggct tcatcgggaa gcagttcttc ggcctcaagc acatgccgca    2100
gaccgggttc gactacgact tcttcctctt ccagtgggcc ttcgccatcg ccgccgccgg    2160
gatcacgtcg ggctccatcg ccgagaggac gcagttcgtc gcctacctca tctactccgc    2220
cttcctcacc gggttcgtct acccggtggt gtcccactgg atctggtccg ccgatgggtg    2280
ggcctctgcc tcccgcacgt ccggacctct gctgttcggc tccggtgtca tcgacttcgc    2340
cggctccggc gtcgtccaca tggtcggcgg tgtcgccggg ctctggggcg cgctcatcga    2400
gggcccccgc atcgggaggt tcgaccacgc cggccgatcg gtggcgctca agggccacag    2460
cgcgtcgctc gtcgtgcttg gcaccttcct gctgtggttc ggctggtacg gattcaaccc    2520
cgggtcgttc accaccatcc tcaagacgta cggcccggcc ggcggcatca acgggcagtg    2580
gtccggagtc ggccgcaccg ccgtgacgac gaccctggcc ggcagcgtgg cggcgctcac    2640
cacgctgttc gggaagcggc tccagacggg gcactggaac gtggtcgacg tctgcaacgg    2700
cctcctcggc gggttcgccg ccatcaccgc cgggtgcagc gtcgtcgacc cgtgggccgc    2760
gatcatctgc gggttcgtct cggcgtgggt gctcatcggc ctcaacgcgc tcgccgcgcg    2820
cctcaagttc gacgacccgc tcgaggccgc ccagctccac ggcgggtgcg gcgcgtgggg    2880
gatcctcttc accgcgctct tcgcgaggca gaagtacgtc gaggagatct acggcgccgg    2940
ccggccgtac ggcctgttca tgggcggcgg cggcaagctg ctcgccgcgc acgtcatcca    3000
gatcctggtc atcttcgggt gggtcagctg caccatggga cctctcttct acgggctcaa    3060
gaagctcggc ctgctccgca tctccgccga ggacagacg tccggcatgg acctgacacg    3120
gcacggcggg ttcgcgtacg tctaccacga cgaggacgag cacgacaagt ctggggttgg    3180
tgggttcatg ctccggtccg cgcagacccg cgtcgagccg gcggcggccg gctgcctcca    3240
acagcaacaa ccaagtgtaa ccaatccaga acgaacgacg tcacagcgaa ggaagaaatc    3300
acgggtttct ctccctctcc gatctcgatc gtcacgtcat aaatttgatc cccatatttg    3360
attgccagtt tctgtttggg ccaaatgctt ttgccgctct ctctggtgtt gcaagactgt    3420
aaaaacactg taggatggac gagtgtcttt cacttttgct gggcttctct tgtgtacagg    3480
catgcgtacg tgtcttagaa tgtgtggtgt gaaggtggga agaatcagag gttagggttt    3540
aattttcttt tgcacaatgg ttactgctat tattgtttta ttttgtggtc gaattttatc    3600
gtcataaggg tgtggtggaa tggtggtcaa gataggtggc tgtgcagggc tcaaagactt    3660
tgcgtgggtc cttttgtcct gcagtgctct acctctctat caaaactttg gcttatttcc    3720
tggaatctag tggtttgaga gtgtttgttt tatactcagt tctgcattat gtttacgata    3780 tattttttt tttaccaaaa gcatttcatt taaactctac cgagagtact tgtttatgct    3840
gaatcagtac atctacactg agtgatattt agagccttat actaattgaa gattaaatag    3900
tcaaagtcca tgtgcacatt tctactcgcc agttagtctg aaagaaaaga ttcctgtgtg    3960
caattgtgca tatcagcata tgccacctgg cgataaagta aacatactat agttgtgaac    4020
tgtgcgatga caacgaccaa attaagcagc ctgatctttta caacgaccgc tgtatagaga    4080
```
acagactata tcaaggtttt gggtccgtgg tcttctttt ggg                4123

<210> SEQ ID NO 30
<211> LENGTH: 532
<212> TYPE: PRT
<213> ORGANISM: Oryza sativa

<400> SEQUENCE: 30

```
Met Ala Thr Cys Ala Ala Asp Leu Ala Pro Leu Leu Gly Pro Val Ala
  1               5                  10                  15

Ala Asn Ala Thr Asp Tyr Leu Cys Asn Arg Phe Ala Asp Thr Thr Ser
                 20                  25                  30

Ala Val Asp Ala Thr Tyr Leu Leu Phe Ser Ala Tyr Leu Val Phe Ala
             35                  40                  45

Met Gln Leu Gly Phe Ala Met Leu Cys Ala Gly Ser Val Arg Ala Lys
 50                  55                  60

Asn Thr Met Asn Ile Met Leu Thr Asn Val Leu Asp Ala Ala Ala Gly
 65                  70                  75                  80

Ala Leu Phe Tyr Tyr Leu Phe Gly Phe Ala Phe Ala Phe Gly Thr Pro
                 85                  90                  95

Ser Asn Gly Phe Ile Gly Lys Gln Phe Phe Gly Leu Lys His Met Pro
                100                 105                 110

Gln Thr Gly Phe Asp Tyr Asp Phe Phe Leu Phe Gln Trp Ala Phe Ala
            115                 120                 125

Ile Ala Ala Ala Gly Ile Thr Ser Gly Ser Ile Ala Glu Arg Thr Gln
130                 135                 140

Phe Val Ala Tyr Leu Ile Tyr Ser Ala Phe Leu Thr Gly Phe Val Tyr
145                 150                 155                 160

Pro Val Val Ser His Trp Ile Trp Ser Ala Asp Gly Trp Ala Ser Ala
                165                 170                 175

Ser Arg Thr Ser Gly Pro Leu Leu Phe Gly Ser Gly Val Ile Asp Phe
                180                 185                 190

Ala Gly Ser Gly Val Val His Met Val Gly Gly Val Ala Gly Leu Trp
            195                 200                 205

Gly Ala Leu Ile Glu Gly Pro Arg Ile Gly Arg Phe Asp His Ala Gly
210                 215                 220

Arg Ser Val Ala Leu Lys Gly His Ser Ala Ser Leu Val Val Leu Gly
225                 230                 235                 240

Thr Phe Leu Leu Trp Phe Gly Trp Tyr Gly Phe Asn Pro Gly Ser Phe
                245                 250                 255

Thr Thr Ile Leu Lys Thr Tyr Gly Pro Ala Gly Gly Ile Asn Gly Gln
                260                 265                 270

Trp Ser Gly Val Gly Arg Thr Ala Val Thr Thr Leu Ala Gly Ser
            275                 280                 285

Val Ala Ala Leu Thr Thr Leu Phe Gly Lys Arg Leu Gln Thr Gly His
290                 295                 300

Trp Asn Val Val Asp Val Cys Asn Gly Leu Leu Gly Gly Phe Ala Ala
305                 310                 315                 320

Ile Thr Ala Gly Cys Ser Val Val Asp Pro Trp Ala Ala Ile Ile Cys
                325                 330                 335

Gly Phe Val Ser Ala Trp Val Leu Ile Gly Leu Asn Ala Leu Ala Ala
                340                 345                 350

Arg Leu Lys Phe Asp Asp Pro Leu Glu Ala Ala Gln Leu His Gly Gly
            355                 360                 365
```

```
Cys Gly Ala Trp Gly Ile Leu Phe Thr Ala Leu Phe Ala Arg Gln Lys
        370                 375                 380

Tyr Val Glu Glu Ile Tyr Gly Ala Gly Arg Pro Tyr Gly Leu Phe Met
385                 390                 395                 400

Gly Gly Gly Gly Lys Leu Leu Ala Ala His Val Ile Gln Ile Leu Val
                405                 410                 415

Ile Phe Gly Trp Val Ser Cys Thr Met Gly Pro Leu Phe Tyr Gly Leu
            420                 425                 430

Lys Lys Leu Gly Leu Leu Arg Ile Ser Ala Glu Asp Glu Thr Ser Gly
        435                 440                 445

Met Asp Leu Thr Arg His Gly Gly Phe Ala Tyr Val Tyr His Asp Glu
    450                 455                 460

Asp Glu His Asp Lys Ser Gly Val Gly Gly Phe Met Leu Arg Ser Ala
465                 470                 475                 480

Gln Thr Arg Val Glu Pro Ala Ala Ala Gly Cys Leu Gln Gln Gln Gln
                485                 490                 495

Pro Ser Val Thr Asn Pro Glu Arg Thr Thr Ser Gln Arg Arg Lys Lys
            500                 505                 510

Ser Arg Val Ser Leu Pro Leu Arg Ser Arg Ser Arg His Lys Phe
        515                 520                 525

Asp Pro His Ile
    530

<210> SEQ ID NO 31
<211> LENGTH: 4654
<212> TYPE: DNA
<213> ORGANISM: Oryza sativa

<400> SEQUENCE: 31
gagctccact cagctaccgg atcttgaccg ggaacctgtt tgtctacgta ctccaacgcc      60
ttgaatgatg ccgccgtgca gccaatttta accagctgct gcgcaaccgg ccaaccgccc     120
agccgtgcag ctgtggtgga gtgaccacgg ccacgactcc gtgcgcgcgg gtggacgtaa     180
gcgttgggcc ctcggctcgc gcgcgcggcc gcatccggcg atgcatcggt cgcgttcgcg     240
gtttgtggct tcgcgtcatc gccgatgcga acagaggctg ctttgcgttg tcgtcatcgg     300
cttgttgacg tccacgagtt ggcgagttgc tctgttcctc tctcgcgcgc gccgcagata     360
tccgaggtgg aaaaaatata ctacatatga acagatgtgg cccagctgtg agcaagacgc     420
caagaccaaa gataagtgca gttcaaatgg gcctgaaatt ggccttcatc aattacaaag     480
cccgtgaaaa gtttcagaaa agcattacaa agcttcagat aagttcaggg gtgactgaaa     540
tacacataca acaagtaacg tagagagatc cccaaatcag ctgcggcaga aggcagaaac     600
cgtgactagt acatctcata aacttaacga gcagtacaat ttctgtacat tggtttatca     660
ataagtcaag agtagcattt gggtaagaag agaaaaaaaa tcttttacgg tggcgtttat     720
tgacatttga tccctggagc cgagaagact agtttatctc atccgtgaaa actatttgtc     780
actagacatc aacgtctcgc tgaggacacc cggtttgcaa tttgctaata agaaacactc     840
gtttccgtcc aatggcgatt cgtttactag agatccgtcc attctctgaa cttctgaagg     900
tcaaccttct gatatgcata caggtgtggt agcaggcacg acaaaagtat aaaacaatag     960
gtatttaatc gcatcagcgt gatctatctc cagagtgtaa aaattagata cgcagcatct    1020
gcaagtcata cttgcaagga agaagcaatt gcgtccctat ccaccacatc ttatccagtc    1080
ttgtcagagt tttgacctaa ggaattgctt catcatctga attattcta ctggaagaaa     1140 ttacctactg ctatgccaag aagtaagaat acatggttaa tctatgttga caccctcatt    1200
```

```
tctgaagaca aacaacataa atttgcagtg agttaaaaca tatagtttca gtgaaaatat   1260
cgtacaggtt aatgtagcca gaccaacaca gagatctgat tgacaattac agagtactca   1320
gtagtcagca agcaggttta gcatggacta cctgttgatt acatggtttc agtcagacac   1380
gagttcttca gggaggcaaa ttaatcacaa ggttcttcca agacagaagc cgccggtaag   1440
gtatggaagc aaatgggttt atctccgttt gtgccaataa ccttatcgaa tatctaattg   1500
ttcgctaagt acgcattgca cacatcatat accatctcga ttgatgagtt ttgtcgccat   1560
gttctgctag gtacgaccta tccgctgctg ggtttacatg catgcctgaa gaacttaaac   1620
agttaatcaa caaagtcaat ggatattacg catacaagta tatggttgta tatatgcaac   1680
ttcatgacac aacagtatgc gtatagtcgg acgtgacgac aagcaactac ctcgtgcaag   1740
gatgcgagga gataccagat taaaacctgt aatacttgaa gttgacaaaa tgcgattctt   1800
cagacgatat aataacaaga acatttctga atcttccttt aaaaaatgtt gaatgcataa   1860
aagaatctta gctgtgatgg caacaacacg actttctgat agtgacattg gatcttagtt   1920
gaatctggca tcttgcgtat gcgaccttgc ttggatctgt cggatactcc caacccagca   1980
taaattactg atgtctgaaa ctttctgagc aaagcgggaa ctcaggctag ttgagtcgct   2040
catcatcaaa agtcaagaca atacttaagt aaaaacaaaa caaatatcac tgtcgcaaaa   2100
ccagtgtaaa cctattggga taattttaac agtcttacaa caccagcgcc gagacgtcta   2160
ggtaacaaat taaatcatca ctgacaatat ttgaagataa gtgaatcaca tgtctttctc   2220
aatgaactta aatttatgaa tgaaccaacc tatacatgca actaaatatg atatcaagat   2280
cagttaaaaa tcttgttttg tgaaatttca aaacaaaaaa ataaaattgc agcgtacctt   2340
tatttcaaga gaaatttaat tcactaaaaa aaagtaattg tatgtgccaa attttacatt   2400
aaaaaatggt atctgcaatg tattcttaag gatgataaaa ttatctcagt aatattcaat   2460
cattcattaa tagaggtgaa ctgctcgttc ttttactcat cacacctgtt ggatgaaaag   2520
attggttgct gccactaaaa aaattaatca actcattgca gttggcaaaa aagaaaaaaa   2580
aaggttttca ggcactagta tatgtgatgt tagaaggaat ccaaaacagt atacatgcat   2640
ccacgcgcac ctcggttttg catttcccgc tgtctgtgat catgaatcat ccaattaaaa   2700
acaaccatca accatggatt ccaatgtgtt ctgcccctat aaatagtcca gcatctcatt   2760
ctctcgtcta cttcaaagaa tcacacacca aaacctccat tagttcctaa accctagcaa   2820
gaagcagcac aaaaccttgc cacacttggc tagtgacact gagacacacc atggcgacgt   2880
gcttggacag cctcgggccg cttctcggcg gcgcggcgaa ctccaccgac gcggccaact   2940
acatctgcaa caggttcacg gacacctcct ccgcggtgga cgcgacgtac ctgctcttct   3000
cggcctacct cgtgttcgcc atgcagctcg ggttcgccat gctctgcgcg ggctccgtcc   3060
gcgccaagaa ctcaatgaac atcatgctca ccaacgtgtt cgacgccgcc gccggcgcgc   3120
tcttctacta cctcttcggc ttcgcttcgc gtcggacgcc gtccaagggc ttcatcggga   3180
agcagttctt cgggctgaag cacatgccgc agacagggta cgactacgac ttcttcctct   3240
tccagtgggc cttcgccatc gccgccgccg gcatcacgtc cggttccatc gccgaacgga   3300
cgcgcttcag cgcgtatctc atctactccg ccttcctcac cgggttcgtg tacccggtgg   3360
tgtcgcactg gttctggtcc accgacgggt gggcttcggc cggccggctg acgggtccgt   3420
tgctgttcaa gtcgggcgtc atcgacttcg ccggctccgg cgtcgtccat ctggtcggtg   3480
gcattgctgg cctgtggggt gccttcatcg agggcccccg catcgggcgc ttcgacgccg   3540
ccggccgcac ggtggcgatg aaagggcaca gcgcctcact ggtcgtgctc ggcaccttcc   3600
```

```
tgctgtggtt cgggtggttc ggcttcaacc cggggtcctt caccaccatc tccaagatct    3660
acggcgagtc gggcacgatc gacgggcagt ggtcggcggt gggccgcacc gccgtgacga    3720
cgtcgctggc gggcagcgtc gccgcgctta accacgctgt acggcaagag atggctgacg    3780
gggcactgga acgtgaccga cgtctgcaac ggtctcctcg gcgggttcgc gcgatcaccg    3840
cgggctgctc cgtggtcgac ccgtgggcgt cggtgatctg cggggtcgtg tcggcgtggg    3900
tcctcatcgg ctgcaacaag ctggcgctga tgctcaagtt cgatgacccg ctggaggcga    3960
cgcagctgca cggcgggtgc ggcgcgtggg ggatcatctt caccgcgctg ttcgcgcgca    4020
aggagtacgt cgagctgatc tacggggtgc cggggaggcc gtacgggctg ttcatgggcg    4080
gcggcgggag gcttctcgcg gcgcacatcg tgcagatcct ggtgatcgtc gggtgggtca    4140
gcgccaccat ggggacgctc ttctacgtgc tgcacaggtt cgggctgctc cgcgtctcga    4200
cctcgacaga gatggaaggc atggacccgt cgtgccacgg cgggttcggg tacgtggacg    4260
aggacgaagg ccagcgccgc gtcagggcca agtcggcggc ggagacggct cgcgtggagc    4320
ccagaaagtc gccggagcaa ccgcggcgcg gccagttggt gtagtaggat catatcgatc    4380
gtgtccgttc ggggaaagtg tttgtgaag tgtgcatata aagctgagg cagtcagtcg     4440 tgtgggcgtg gtggcacttc agcccatggt ggttgtggct ttcttttgat atttgcttcc    4500
tttcttctct gcatttgcat ctgtatggat ttttgtggct ttcaatcttt tatgcttttc    4560
tttaggtatt cagtcttta tgctttcttg tacatgttta gacgtgtcca gtttgtatca     4620
gtatttaggt cattatgatg ttaacgtgga gctc                                4654
```

<210> SEQ ID NO 32
<211> LENGTH: 497
<212> TYPE: PRT
<213> ORGANISM: Oryza sativa

<400> SEQUENCE: 32

```
Met Ala Thr Cys Leu Asp Ser Leu Gly Pro Leu Gly Gly Ala Ala
 1               5                  10                  15

Asn Ser Thr Asp Ala Ala Asn Tyr Ile Cys Asn Arg Phe Thr Asp Thr
            20                  25                  30

Ser Ser Ala Val Asp Ala Thr Tyr Leu Leu Phe Ser Ala Tyr Leu Val
        35                  40                  45

Phe Ala Met Gln Leu Gly Phe Ala Met Leu Cys Ala Gly Ser Val Arg
    50                  55                  60

Ala Lys Asn Ser Met Asn Ile Met Leu Thr Asn Val Phe Asp Ala Ala
65                  70                  75                  80

Ala Gly Ala Leu Phe Tyr Tyr Leu Phe Gly Phe Ala Ser Arg Arg Thr
                85                  90                  95

Pro Ser Lys Gly Phe Ile Gly Lys Gln Phe Gly Leu Lys His Met
            100                 105                 110

Pro Gln Thr Gly Tyr Asp Tyr Asp Phe Phe Leu Phe Gln Trp Ala Phe
        115                 120                 125

Ala Ile Ala Ala Ala Gly Ile Thr Ser Gly Ser Ile Ala Glu Arg Thr
    130                 135                 140

Arg Phe Ser Ala Tyr Leu Ile Tyr Ser Ala Phe Leu Thr Gly Phe Val
145                 150                 155                 160

Tyr Pro Val Val Ser His Trp Phe Trp Ser Thr Asp Gly Trp Ala Ser
                165                 170                 175

Ala Gly Arg Leu Thr Gly Pro Leu Leu Phe Lys Ser Gly Val Ile Asp
            180                 185                 190
```

Phe Ala Gly Ser Gly Val Val His Leu Val Gly Gly Ile Ala Gly Leu
            195                 200                 205

Trp Gly Ala Phe Ile Glu Gly Pro Arg Ile Gly Arg Phe Asp Ala Ala
            210                 215                 220

Gly Arg Thr Val Ala Met Lys Gly His Ser Ala Ser Leu Val Val Leu
225                 230                 235                 240

Gly Thr Phe Leu Leu Trp Phe Gly Trp Phe Gly Phe Asn Pro Gly Ser
            245                 250                 255

Phe Thr Thr Ile Ser Lys Ile Tyr Gly Glu Ser Gly Thr Ile Asp Gly
            260                 265                 270

Gln Trp Ser Ala Val Gly Arg Thr Ala Val Thr Thr Ser Leu Ala Gly
            275                 280                 285

Ser Val Ala Ala Leu Asn His Ala Val Arg Gln Glu Met Ala Asp Gly
            290                 295                 300

Ala Leu Glu Arg Asp Arg Arg Leu Gln Arg Ser Pro Arg Arg Val Arg
305                 310                 315                 320

Ala Ile Thr Ala Gly Cys Ser Val Val Asp Pro Trp Ala Ser Val Ile
            325                 330                 335

Cys Gly Phe Val Ser Ala Trp Val Leu Ile Gly Cys Asn Lys Leu Ala
            340                 345                 350

Leu Met Leu Lys Phe Asp Asp Pro Leu Glu Ala Thr Gln Leu His Gly
            355                 360                 365

Gly Cys Gly Ala Trp Gly Ile Ile Phe Thr Ala Leu Phe Ala Arg Lys
            370                 375                 380

Glu Tyr Val Glu Leu Ile Tyr Gly Val Pro Gly Arg Pro Tyr Gly Leu
385                 390                 395                 400

Phe Met Gly Gly Gly Arg Leu Leu Ala Ala His Ile Val Gln Ile
            405                 410                 415

Leu Val Ile Val Gly Trp Val Ser Ala Thr Met Gly Thr Leu Phe Tyr
            420                 425                 430

Val Leu His Arg Phe Gly Leu Leu Arg Val Ser Thr Ser Thr Glu Met
            435                 440                 445

Glu Gly Met Asp Pro Ser Cys His Gly Gly Phe Gly Tyr Val Asp Glu
            450                 455                 460

Asp Glu Gly Gln Arg Arg Val Arg Ala Lys Ser Ala Ala Glu Thr Ala
465                 470                 475                 480

Arg Val Glu Pro Arg Lys Ser Pro Glu Gln Ala Ala Gly Gln Leu
            485                 490                 495
Val

<210> SEQ ID NO 33
<211> LENGTH: 2987
<212> TYPE: DNA
<213> ORGANISM: Oryza sativa
<220> FEATURE:
<221> NAME/KEY: misc_feature
<222> LOCATION: 212
<223> OTHER INFORMATION: n = A,T,C or G

<400> SEQUENCE: 33
attatctcca atgatttcat agctaatcca tatgctggaa gggttaggaa ttcaagccat     60
ttcaaattcc aaaaaattac ctatactaaa gtaaaaaaaa acctatgacc taccctcaat    120
gtttgttaac caatttaggc cttgtttgat tccacttaga attattataa tcctgattat    180
tattaggagt aagctgaaac aaacagataa cntattatga tagattatta taatctataa    240

```
gccagattac tataatctgg taatccactc taaaggtgct ttttttaatt attggatagc    300
taataactag caaacagcta ataatccaga taaacaaaca gctaacaact tattctatat    360
cggcttatta taatcttatt ataatccaat ttatagtaat ctagctcaat aatatatatt    420
ataataatct taaactgaaa caaacagggc tttagaaatt catatgtttt gaaatggaga    480
tagtaccact cagaaagctt gaaggatttc atgtgttttg gttaacatat tcatgtgtgt    540
cttttcgtgc aaccaaaatt ttcttagaa acatggtgaa ccaattagat ttagaaatta     600
taaaatattt ccaagtgtta caagtggaaa tataataaaa ataatattgt taaaaaagta    660
aagaaagttt aagtacaaac tgaggaggaa atataacaag tgcttcacta tagacaaata    720
tagaggtgga cgaaatgtac aaacagtcgt ttttaaaaat acaaaccacc gtattgcgac    780
tcaggccttg tttagatccc aaaaaatttt agccaaaaat atcacatcaa atgtttggac    840
acatgcatag gatattaaat atggggaaaa aaaatcaatt acacagtttg caggtaaatt    900
gcgagacaaa tcttttttagt ctaattacgt catgatttga ccatgtgatg ctatagtaaa   960
catttactaa tgacagattg attaggctta ataaattcat ctcgcaattt acaaacagaa   1020
tctataattt atttttattat tagtctatat ttaatatttt aaatatatat ccgtgtagtt   1080
caaaactttt atatcaaaag aactaaacac agcctccagg ccgcagccta cagtaggcct   1140
atagagagat tccacgggat tcgatgaact acgaccacga acaggagggg gacaaatcaa   1200
caagcaaatc atagggtcg cacatttcag aggtagccaa agattcactg gcaggtgggc    1260
ccttcacact ttgaaggaat caacaacgac accccccaag tcatggattc cttctcgctc   1320
cctctccacg tcgcctataa atccgacgcg ggccgctccc cactccaccc acagcccaca   1380
cttccattgc cctccccctc tcctctacag tctgtgttga gcgcgcgtcg agcggcgagg   1440
atggcaacgt gcgcggatac cctcggcccg ctgctgggca cggcggcggc gaacgcgacg   1500
gactacctgt gcaaccagtt cgcggacacc acgtcggccg tggactcgac gtacctgctc   1560
ttctcggcgt acctcgtgtt cgccatgcag ctcggcttcg ccatgctctg cgccgggtcc   1620
gtccgcgcca agaacaccat gaacatcatg cttaccaacg tgctcgacgc cgccgccggc   1680
gcgctcttct actacctctt cggcttcgcc ttcgccttcg gggcgccgtc caacggcttc   1740
atcgggaagc acttcttcgg cctcaagcag gtcccacagg tcggcttcga ctacagcttc   1800
ttcctcttcc agtgggcctt cgccatcgcc gccgcgggca tcacgtccgg ctccatcgcc   1860
gagcggaccc agttcgtggc gtacctcatc tactccgcct tcctcaccgg cttcgtctac   1920
ccggtggtgt cccactggat ctggtccgcc gacgggtggg cctcggcttc ccgaacgtcg   1980
gggtcgctgc tcttcgggtc cggcgtcatc gacttcgccg ggtcaggggt tgtccacatg   2040
gtggcggcgt gccggactct ggggcgccct catcgagggc cccgcattg gcggttcgac    2100 cacgccggcc gctcggtggc gctgcgcggc cacagcgcgt cgctcgtcgt gctcggcagc   2160
ttcctgctgt ggtcgggtg tacgggtttt aaccccggct cgttcctcac catcctcaaa    2220
tcctacggcc cgcccggtag catccacggg cagtggtcgg cggtgggacg caccgccgtg   2280
accaccaccc tcgccggcag cacgcgcgcg ctcacgacgc tcttcgggaa gaggctccag   2340
acggggcact ggaacgtgat cgacgtctgc aacggcctcc tcggcggctt cgcggcgatc   2400
accgccggtt gctccgtcgt cgacccgtgg gccgcgatca tctgcgggtt cgtctcggcg   2460
tgggtgctca tcggcctcaa cgcgctggcg gcgaggctca agttcgacga cccgctcgag   2520
gcggcgcagc tgcacggcgg gtgcggcgcg tgggggtca tcttcacggc gctgttcgcg    2580
cgcaaggagt acgtggacca gatcttcggc cagcccgggc gcccgtatgg gctgttcatg   2640
```

```
ggcggcggcg gccggctgct cggggcgcac atagtggtaa tcctggtcat cgcggcgtgg    2700
gtgagcttca ccatggcgcc gctgttcctg gtgctcaaca agctgggatt gctgcgcatc    2760
tcggccgagg acgagatggc cggcatggac cagacgcgcc acggcgggtt cgcgtacgcg    2820
taccacgacg acgacgcgag cggcaagccg gaccgcagct tcggcgggtt catgctcaag    2880
tcggcgcacg gcacgcaggt cgccgccgag atgggaggcc atgtctagtg gaaccggagg    2940
agctgagcta gtagtacata catgcagcat catcgatcct cgagctc                  2987
```

<210> SEQ ID NO 34
<211> LENGTH: 495
<212> TYPE: PRT
<213> ORGANISM: Oryza sativa

<400> SEQUENCE: 34

```
Met Ala Thr Cys Ala Asp Thr Leu Gly Pro Leu Leu Gly Thr Ala Ala
 1               5                  10                  15

Ala Asn Ala Thr Asp Tyr Leu Cys Asn Gln Phe Ala Asp Thr Thr Ser
            20                  25                  30

Ala Val Asp Ser Thr Tyr Leu Leu Phe Ser Ala Tyr Leu Val Phe Ala
        35                  40                  45

Met Gln Leu Gly Phe Ala Met Leu Cys Ala Gly Ser Val Arg Ala Lys
    50                  55                  60

Asn Thr Met Asn Ile Met Leu Thr Asn Val Leu Asp Ala Ala Ala Gly
65                  70                  75                  80

Ala Leu Phe Tyr Tyr Leu Phe Gly Phe Ala Phe Ala Phe Gly Ala Pro
                85                  90                  95

Ser Asn Gly Phe Ile Gly Lys His Phe Phe Gly Leu Lys Gln Val Pro
            100                 105                 110

Gln Val Gly Phe Asp Tyr Ser Phe Phe Leu Phe Gln Trp Ala Phe Ala
        115                 120                 125

Ile Ala Ala Ala Gly Ile Thr Ser Gly Ser Ile Ala Glu Arg Thr Gln
    130                 135                 140

Phe Val Ala Tyr Leu Ile Tyr Ser Ala Phe Leu Thr Gly Phe Val Tyr
145                 150                 155                 160

Pro Val Val Ser His Trp Ile Trp Ser Ala Asp Gly Trp Ala Ser Ala
                165                 170                 175

Ser Arg Thr Ser Gly Ser Leu Leu Phe Gly Ser Gly Val Ile Asp Phe
            180                 185                 190

Ala Gly Ser Gly Val Val His Met Val Ala Ala Cys Arg Thr Leu Gly
        195                 200                 205

Arg Pro His Arg Gly Pro Pro His Trp Arg Phe Asp His Ala Gly Arg
    210                 215                 220

Ser Val Ala Leu Arg Gly His Ser Ala Ser Leu Val Val Leu Gly Ser
225                 230                 235                 240

Phe Leu Leu Trp Phe Gly Trp Tyr Gly Phe Asn Pro Gly Ser Phe Leu
                245                 250                 255

Thr Ile Leu Lys Ser Tyr Gly Pro Pro Gly Ser Ile His Gly Gln Trp
            260                 265                 270

Ser Ala Val Gly Arg Thr Ala Val Thr Thr Thr Leu Ala Gly Ser Thr
        275                 280                 285

Ala Ala Leu Thr Thr Leu Phe Gly Lys Arg Leu Gln Thr Gly His Trp
    290                 295                 300

Asn Val Ile Asp Val Cys Asn Gly Leu Leu Gly Gly Phe Ala Ala Ile
305                 310                 315                 320
```

```
Thr Ala Gly Cys Ser Val Val Asp Pro Trp Ala Ile Ile Cys Gly
            325                 330                 335

Phe Val Ser Ala Trp Val Leu Ile Gly Leu Asn Ala Leu Ala Ala Arg
        340                 345                 350

Leu Lys Phe Asp Asp Pro Leu Glu Ala Ala Gln Leu His Gly Gly Cys
        355                 360                 365

Gly Ala Trp Gly Val Ile Phe Thr Ala Leu Phe Ala Arg Lys Glu Tyr
        370                 375                 380

Val Asp Gln Ile Phe Gly Gln Pro Gly Arg Pro Tyr Gly Leu Phe Met
385                 390                 395                 400

Gly Gly Gly Gly Arg Leu Leu Gly Ala His Ile Val Val Ile Leu Val
                405                 410                 415

Ile Ala Ala Trp Val Ser Phe Thr Met Ala Pro Leu Phe Leu Val Leu
                420                 425                 430

Asn Lys Leu Gly Leu Leu Arg Ile Ser Ala Glu Asp Glu Met Ala Gly
                435                 440                 445

Met Asp Gln Thr Arg His Gly Gly Phe Ala Tyr Ala Tyr His Asp Asp
        450                 455                 460

Asp Ala Ser Gly Lys Pro Asp Arg Ser Phe Gly Phe Met Leu Lys
465                 470                 475                 480

Ser Ala His Gly Thr Gln Val Ala Ala Glu Met Gly Gly His Val
                485                 490                 495

<210> SEQ ID NO 35
<211> LENGTH: 900
<212> TYPE: DNA
<213> ORGANISM: Oryza sativa

<400> SEQUENCE: 35
atggcggcgg aggcggcgcc ggagtggggtg gagaaggggg acaacgcgtg gccgctagcg      60
gcggcgacgc tggtggggct gcagagcgtg ccgaggctgg tgatcctgta cggcgactgc     120
ggcgcggtcg gtccgaggac ggagaaggac agggaggcgt tcccgccgaa caacgtcctg     180
ctcacgctcg ccggagcggg gctgctgctg tggatgggt ggacgggtt caacggcggc     240 gcgccgtacg ccgccaacgt cgacgcgtcg gtcaccgtcg tgaacacgca cctctgcacg     300
gcgacgagcc tcctggtgtg gctcctcctc gacagcttcg tcttcggccg cctctccgtc     360
atcagcgccg tgcagggcat gatcaccggc ctcgtctgcg tcaccccggc ggccaggctg     420
gtgctgcaca gcggagccg cctcctggcg cgcgtcgacg acacgctcgc cgtgctccac     480
acccacggcg tcgccggcag cctcagcggc gtcctgacgg gctcctgct cctcgccgag     540 ccgcgcttcg ccaggctctt cttcggcgac acccgcgct acgtcggcct cgcgtacgct     600
gtcagggacg gccgcgccgg ctcggggctc cggcaggtcg gcgtgcagct ggccgggatc     660
gcgttcgtgg tggcgctcaa cgtcgccgtg acgagcgccg tgtgcctggc cgtcagggtg     720
gccgtgccgc agctcgccgg cggcggcgac gccatacacg gcgaggacgc gtacgcggtg     780
tggggcgacg gcgagacgta cgagcagtac tccgtgcacg gcggcggcag caaccacggc     840 ggcttccccca tgacgccaa tcccgtggcg tccaaagccg acgagatgat atggatataa     900

<210> SEQ ID NO 36
<211> LENGTH: 299
<212> TYPE: PRT
<213> ORGANISM: Oryza sativa

<400> SEQUENCE: 36

Met Ala Ala Glu Ala Ala Pro Glu Trp Val Glu Lys Gly Asp Asn Ala
```

```
                 1               5                  10                 15
Trp Pro Leu Ala Ala Ala Thr Leu Val Gly Leu Gln Ser Val Pro Arg
                    20                  25                  30

Leu Val Ile Leu Tyr Gly Asp Cys Gly Ala Val Gly Pro Arg Thr Glu
                35                  40                  45

Lys Asp Arg Glu Ala Phe Pro Pro Asn Asn Val Leu Leu Thr Leu Ala
 50                  55                  60

Gly Ala Gly Leu Leu Leu Trp Met Gly Trp Thr Gly Phe Asn Gly Gly
 65                  70                  75                  80

Ala Pro Tyr Ala Ala Asn Val Asp Ala Ser Val Thr Val Val Asn Thr
                    85                  90                  95

His Leu Cys Thr Ala Thr Ser Leu Leu Val Trp Leu Leu Leu Asp Ser
                100                 105                 110

Phe Val Phe Gly Arg Leu Ser Val Ile Ser Ala Val Gln Gly Met Ile
                115                 120                 125

Thr Gly Leu Val Cys Val Thr Pro Ala Ala Arg Leu Val Leu His Lys
                130                 135                 140

Arg Ser Arg Leu Leu Ala Arg Val Asp Asp Thr Leu Ala Val Leu His
145                 150                 155                 160

Thr His Gly Val Ala Gly Ser Leu Ser Gly Val Leu Thr Gly Leu Leu
                165                 170                 175

Leu Leu Ala Glu Pro Arg Phe Ala Arg Leu Phe Gly Asp Asp Pro
                180                 185                 190

Arg Tyr Val Gly Leu Ala Tyr Ala Val Arg Asp Gly Arg Ala Gly Ser
                195                 200                 205

Gly Leu Arg Gln Val Gly Val Gln Leu Ala Gly Ile Ala Phe Val Val
                210                 215                 220

Ala Leu Asn Val Ala Val Thr Ser Ala Val Cys Leu Ala Val Arg Val
225                 230                 235                 240

Ala Val Pro Gln Leu Ala Gly Gly Asp Ala Ile His Gly Glu Asp
                    245                 250                 255

Ala Tyr Ala Val Trp Gly Asp Gly Glu Thr Tyr Glu Gln Tyr Ser Val
                260                 265                 270

His Gly Gly Gly Ser Asn His Gly Gly Phe Pro Met Thr Ala Asn Pro
                275                 280                 285

Val Ala Ser Lys Ala Asp Glu Met Ile Trp Ile
                290                 295

<210> SEQ ID NO 37
<211> LENGTH: 2040
<212> TYPE: DNA
<213> ORGANISM: Oryza sativa

<400> SEQUENCE: 37
ggaggctttg ctaccctgc tcccctcgcc atttcattgg ccgtttcgtg gccatccatc      60
acgaactcga tcgattcccc tcttcgagcc cgtaccaatt attagctagt ttaactcgta     120
cgatgaatca cgccgaaaca caatataaat ggtggagtcg ctcgctgtc aaacgcgcgg     180 gagctcgcgc cacttgtaat ttttcgcgtc tcctctcgtc cggcacagca caggagcgcg     240
gacttgaaga cctcaagtag cgattcgtcc gtgcggcgcg gcgcaagaag ggaagggaag     300
gggactaggg gagggcgaga tggcggcggc ggggcgtac tcggcgagcc taccggcggt     360
gccggactgg ctgaacaagg gggacaacgc gtgcagctg acggcgtcga cgctggtggg     420
gatccagtcg atgcccgggc tggtggtgct gtacggcagc atcgtgaaga agaagtgggc     480
```

-continued

```
ggtgaactcg gcgttcatgg cgctctacgc ctacgcgtcg tcgctgctgg tgtgggtgct    540
ggtcggcttc cgcatggcgt tcggcgacca gctgctgccg ttctggggca aggccggcgt    600
ggcgctgacc cagagctacc tcgtcggccg cgccacgctg ccggccaccg cgcacggcgc    660
catcccgcgc accgagccct tctacccgga ggccacgctg gtgctcttcc agttcgagtt    720
cgccgccatc acgctcgtcc tcctcgccgg ctccgtcctc ggccgcatga acatcaaggc    780
ctggatggcc ttcaccccgc tctggctcct cctctcctac accgtcggcg ccttcagcct    840
ctggggcggc ggcttcctct accgctgggg cgtcatcgac tactccggcg gctacgtcat    900
ccacctctcc tccggcatcg ccggcttcac cgccgcctac tgggtggggc caaggctgaa    960
gagcgaccgt gagcggttct caccgaacaa catcctgctg atgatcgcgg gcggcgggct   1020
gctgtggatg ggtgggccg ggttcaacgg cggcgcgccg tacgccgcca acatcgcggc   1080
gtcggtcgcc gtgctcaaca ccaacgtctg cgccgccacc agcctcctca tgtggacctg   1140
cctcgacgtc atcttcttcc gcaagccgtc cgtcatcggc gccgtgcagg gcatgatgac   1200
cggcctcgtc tgcatcaccc ccggcgcagg gctggtgcag acctgggcgg ccgtggtaat   1260
gggcatcttc gccggcagcg tgccgtggtt caccatgatg atcctgcaca agaagtcagc   1320
gctgctgatg aaggtggacg acacgctcgc cgtgttccac acccacgccg tggcggggct   1380
cctcggcggc atcctcacgg gcctcctggc caccccggag ctcttctccc tcgagtccac   1440
ggtgccggga ctccgcggcg cgttctacgg cggcggtatc aagcagatcg gcaagcagct   1500
cggcggcgcc gcgttcgtga tcgcgtggaa cctcgtggtc accacggcca tcctcctcgg   1560
catcggcctg ttcatcccgc tgcggatgcc cgacgagcag ctcatgatcg gcgacgacgc   1620
ggcgcacggc gaggaggcct acgcgctgtg gggcgacggc gagaagttcg acgcgacgcg   1680
gcacgacctg tcgaggggcg gcggaggcgg cgacagggac ggccccgccg gcgagcgcct   1740
ctccgcccta ggcgccaggg gcgtcaccat ccagctctag gcgcgccacg ccacgccacg   1800
ccgcgccgcg ccgcggcctg gcctctaatt acacgcgcgt ttgtactgtt tttggacgtg   1860
ttattgttta ggagtagtga agtgaaccaa cgattgactg caaggtgaag ggtgagaacg   1920
cgagagacca gaccactata gtctatagta catatggatg ctgtaatgat gttgatccga   1980
gttcgttttt ccaacacgat aaaggccgac atgcctatta aatttaaaaa aaaaaaaaaa   2040
```

<210> SEQ ID NO 38
<211> LENGTH: 486
<212> TYPE: PRT
<213> ORGANISM: Oryza sativa

<400> SEQUENCE: 38

```
Met Ala Ala Ala Gly Ala Tyr Ser Ala Ser Leu Pro Ala Val Pro Asp
 1               5                  10                  15

Trp Leu Asn Lys Gly Asp Asn Ala Trp Gln Leu Thr Ala Ser Thr Leu
            20                  25                  30

Val Gly Ile Gln Ser Met Pro Gly Leu Val Val Leu Tyr Gly Ser Ile
        35                  40                  45

Val Lys Lys Lys Trp Ala Val Asn Ser Ala Phe Met Ala Leu Tyr Ala
    50                  55                  60

Tyr Ala Ser Ser Leu Leu Val Trp Val Leu Val Gly Phe Arg Met Ala
65                  70                  75                  80

Phe Gly Asp Gln Leu Leu Pro Phe Trp Gly Lys Ala Gly Val Ala Leu
                85                  90                  95

Thr Gln Ser Tyr Leu Val Gly Arg Ala Thr Leu Pro Ala Thr Ala His
            100                 105                 110
```

Gly Ala Ile Pro Arg Thr Glu Pro Phe Tyr Pro Glu Ala Thr Leu Val
            115                 120                 125

Leu Phe Gln Phe Glu Phe Ala Ala Ile Thr Leu Val Leu Leu Ala Gly
    130                 135                 140

Ser Val Leu Gly Arg Met Asn Ile Lys Ala Trp Met Ala Phe Thr Pro
145                 150                 155                 160

Leu Trp Leu Leu Leu Ser Tyr Thr Val Gly Ala Phe Ser Leu Trp Gly
                165                 170                 175

Gly Gly Phe Leu Tyr Arg Trp Gly Val Ile Asp Tyr Ser Gly Gly Tyr
            180                 185                 190

Val Ile His Leu Ser Ser Gly Ile Ala Gly Phe Thr Ala Ala Tyr Trp
        195                 200                 205

Val Gly Pro Arg Leu Lys Ser Asp Arg Glu Arg Phe Ser Pro Asn Asn
    210                 215                 220

Ile Leu Leu Met Ile Ala Gly Gly Leu Leu Trp Met Gly Trp Ala
225                 230                 235                 240

Gly Phe Asn Gly Gly Ala Pro Tyr Ala Ala Asn Ile Ala Ala Ser Val
                245                 250                 255

Ala Val Leu Asn Thr Asn Val Cys Ala Ala Thr Ser Leu Leu Met Trp
            260                 265                 270

Thr Cys Leu Asp Val Ile Phe Phe Arg Lys Pro Ser Val Ile Gly Ala
        275                 280                 285

Val Gln Gly Met Met Thr Gly Leu Val Cys Ile Thr Pro Gly Ala Gly
    290                 295                 300

Leu Val Gln Thr Trp Ala Ala Val Val Met Gly Ile Phe Ala Gly Ser
305                 310                 315                 320

Val Pro Trp Phe Thr Met Met Ile Leu His Lys Lys Ser Ala Leu Leu
                325                 330                 335

Met Lys Val Asp Asp Thr Leu Ala Val Phe His Thr His Ala Val Ala
            340                 345                 350

Gly Leu Leu Gly Gly Ile Leu Thr Gly Leu Leu Ala Thr Pro Glu Leu
        355                 360                 365

Phe Ser Leu Glu Ser Thr Val Pro Gly Leu Arg Gly Ala Phe Tyr Gly
    370                 375                 380

Gly Gly Ile Lys Gln Ile Gly Lys Gln Leu Gly Gly Ala Ala Phe Val
385                 390                 395                 400

Ile Ala Trp Asn Leu Val Val Thr Thr Ala Ile Leu Leu Gly Ile Gly
                405                 410                 415

Leu Phe Ile Pro Leu Arg Met Pro Asp Glu Gln Leu Met Ile Gly Asp
            420                 425                 430

Asp Ala Ala His Gly Glu Glu Ala Tyr Ala Leu Trp Gly Asp Gly Glu
        435                 440                 445

Lys Phe Asp Ala Thr Arg His Asp Leu Ser Arg Gly Gly Gly Gly
    450                 455                 460

Asp Arg Asp Gly Pro Ala Gly Glu Arg Leu Ser Ala Leu Gly Ala Arg
465                 470                 475                 480

Gly Val Thr Ile Gln Leu
            485

<210> SEQ ID NO 39
<211> LENGTH: 1494
<212> TYPE: DNA
<213> ORGANISM: Oryza sativa

<400> SEQUENCE: 39

-continued

```
atggcgtcgc cgacccggcc ggggccgtac atgccgcgcc caccggcggt gccggagtgg      60
ctgaacaccg gggacaacgg gtggcagctc gcggcggcga cgttcgtcgg gctccagtcg     120
atgcctgggc tggtggtgct gtacggcagc atcgtgaaga agaagtgggc cgtcaactcg     180
gccttcatgg cgctgtacgc gtacgcgtcc acgctcatcg tgtgggtgct ggtcggcttc     240
cgcatggcgt tcggcgaccg gctgctcccg ttctggggga aggccggcgc ggcgctgacg     300
gaggggttcc tcgtggcgcg cgcgtcggtc ccggccacgg cgcactacgg aaggacggc      360
gccctggagt cgccgcgcac cgagccgttc tacccggagg cgtccatggt gctgttccag     420
ttcgagctcg ccgccatcac gctggtgctg ctcgccgggt cgctcctcgg gaggatgaac     480
atcaaggcgt ggatggcgtt cactccgctc tggctcctct tctcctacac cgtctgcgcc     540
ttcagcctct ggggcggcgg cttcctctac cagtggggcg tcatcgacta ctccggcgga     600
tacgtcatcc acctctcctc cggcatcgcc ggcttcaccg ccgcctactg ggtggggccg     660
aggctgaaga gcgacaggga gcggttctcg ccgaacaaca tcctcctcat gatcgccggc     720
ggcgggctgc tgtggctggg ctgggccggg ttcaacggcg gcgcgccgta cgccccaaac     780
atcaccgcgt ccatcgccgt gctcaacacc aacgtcagcg ccgcggcgag cctcctcacc     840
tggacctgcc tcgacgtcat cttcttcggc aagccctccg tcatcggcgc cgtgcagggc     900
atgatgaccg gtctcgtctg catcacccc ggcgcaggtc tggtgcacac gtgggcggcc      960
atactgatgg gcatctgtgg cggcagcttg ccgtggttct ccatgatgat cctccacaag    1020
agatcggcgc tgctccagaa ggtggacgac accctcgccg tcttccacac ccacgccgtc    1080
gcgggcctcc tcggcggctt cctcacgggc ctgttcgcct gccggacct caccgccgtc     1140
cacacccaca tccctggcgc gcgcggcgcg ttctacggcg gcggcatcgc ccaggtgggg    1200
aagcagatcg ccggcgcgct cttcgtcgtc gtgtggaacg tcgtggccac caccgtcatc    1260
ctgctcggcg tcggcctcgt cgtcccgctc cgcatgcccg acgagcagct caagatcggc    1320
gacgacgcgg cgcacgggga ggaggcctac cgcgctatggg gagacggcga gaggttcgac   1380
gtgacgcgcc atgagggggc gaggggcggc cgtgggggcg ccgcggtcgt ggacgaggcg    1440
atggatcacc ggctggccgg aatgggagcg agaggagtca cgattcagct gtag          1494
```

<210> SEQ ID NO 40
<211> LENGTH: 497
<212> TYPE: PRT
<213> ORGANISM: Oryza sativa

<400> SEQUENCE: 40

```
Met Ala Ser Pro Thr Arg Pro Gly Pro Tyr Met Pro Arg Pro Pro Ala
  1               5                  10                  15

Val Pro Glu Trp Leu Asn Thr Gly Asp Asn Gly Trp Gln Leu Ala Ala
             20                  25                  30

Ala Thr Phe Val Gly Leu Gln Ser Met Pro Gly Leu Val Val Leu Tyr
         35                  40                  45

Gly Ser Ile Val Lys Lys Lys Trp Ala Val Asn Ser Ala Phe Met Ala
 50                  55                  60

Leu Tyr Ala Tyr Ala Ser Thr Leu Ile Val Trp Val Leu Val Gly Phe
 65                  70                  75                  80

Arg Met Ala Phe Gly Asp Arg Leu Leu Pro Phe Trp Gly Lys Ala Gly
             85                  90                  95

Ala Ala Leu Thr Glu Gly Phe Leu Val Ala Arg Ala Ser Val Pro Ala
        100                 105                 110
```

```
Thr Ala His Tyr Gly Lys Asp Gly Ala Leu Glu Ser Pro Arg Thr Glu
        115                 120                 125

Pro Phe Tyr Pro Glu Ala Ser Met Val Leu Phe Gln Phe Glu Leu Ala
130                 135                 140

Ala Ile Thr Leu Val Leu Leu Ala Gly Ser Leu Leu Gly Arg Met Asn
145                 150                 155                 160

Ile Lys Ala Trp Met Ala Phe Thr Pro Leu Trp Leu Leu Phe Ser Tyr
                165                 170                 175

Thr Val Cys Ala Phe Ser Leu Trp Gly Gly Phe Leu Tyr Gln Trp
                180                 185                 190

Gly Val Ile Asp Tyr Ser Gly Gly Tyr Val Ile His Leu Ser Ser Gly
                195                 200                 205

Ile Ala Gly Phe Thr Ala Ala Tyr Trp Val Gly Pro Arg Leu Lys Ser
        210                 215                 220

Asp Arg Glu Arg Phe Ser Pro Asn Asn Ile Leu Leu Met Ile Ala Gly
225                 230                 235                 240

Gly Gly Leu Leu Trp Leu Gly Trp Ala Gly Phe Asn Gly Gly Ala Pro
                245                 250                 255

Tyr Ala Pro Asn Ile Thr Ala Ser Ile Ala Val Leu Asn Thr Asn Val
                260                 265                 270

Ser Ala Ala Ala Ser Leu Leu Thr Trp Thr Cys Leu Asp Val Ile Phe
                275                 280                 285

Phe Gly Lys Pro Ser Val Ile Gly Ala Val Gln Gly Met Met Thr Gly
        290                 295                 300

Leu Val Cys Ile Thr Pro Gly Ala Gly Leu Val His Thr Trp Ala Ala
305                 310                 315                 320

Ile Leu Met Gly Ile Cys Gly Gly Ser Leu Pro Trp Phe Ser Met Met
                325                 330                 335

Ile Leu His Lys Arg Ser Ala Leu Leu Gln Lys Val Asp Asp Thr Leu
                340                 345                 350

Ala Val Phe His Thr His Ala Val Ala Gly Leu Leu Gly Gly Phe Leu
        355                 360                 365

Thr Gly Leu Phe Ala Leu Pro Asp Leu Thr Ala Val His Thr His Ile
        370                 375                 380

Pro Gly Ala Arg Gly Ala Phe Tyr Gly Gly Ile Ala Gln Val Gly
385                 390                 395                 400

Lys Gln Ile Ala Gly Ala Leu Phe Val Val Trp Asn Val Val Ala
                405                 410                 415

Thr Thr Val Ile Leu Leu Gly Val Leu Val Val Pro Leu Arg Met
                420                 425                 430

Pro Asp Glu Gln Leu Lys Ile Gly Asp Asp Ala Ala His Gly Glu Glu
                435                 440                 445

Ala Tyr Ala Leu Trp Gly Asp Gly Glu Arg Phe Asp Val Thr Arg His
        450                 455                 460

Glu Gly Ala Arg Gly Gly Ala Trp Gly Ala Ala Val Val Asp Glu Ala
465                 470                 475                 480

Met Asp His Arg Leu Ala Gly Met Gly Ala Arg Gly Val Thr Ile Gln
                485                 490                 495

Leu

<210> SEQ ID NO 41
<211> LENGTH: 1494
<212> TYPE: DNA
<213> ORGANISM: Oryza sativa
```

<400> SEQUENCE: 41

```
atggcgtcgc cgccgcagcc cgggccgtac atgccggacc tgccggcggt gccggcgtgg     60
ctgaacaagg gcgacaccgc cgtggcagctg gtggcggcga cgttcgtcgg catccagtcg    120
atgcctgggc tggtggtgat ctacggcagc atcgtgaaga agaagtgggc cgtcaactcc    180
gccttcatgg cgctgtacgc ctacgcgtcc acgcttatcg tgtgggtgct cgtcggcttc    240
cgcatggcgt tcggcgaccg gctgctcccg ttctgggcca aggccgggcc ggcgctgacg    300
caggacttcc tggtgcaacg cgcggtgttc ccggcgacgg cgcactacgg cagcgacggc    360
acgctcgaga cgccgcgcac cgagccgttc tacgcggagg cggcgctggt gctgttcgag    420
ttcgagttcg cggccatcac gctggtgctg ctcgccgggt cgctcctggg gcggatgaac    480
atcaaggcgt ggatggcgtt caccccgctc tggctcctct tctcctacac cgtcggcgcg    540
ttcagcctct ggggcggcgg cttcctctac cagtggggcg tcatcgacta ctccggcgga    600
tacgtcatcc acctctcctc cggcgtcgcc ggcttcaccg ccgcctactg ggtgggcccg    660
aggctgaaga gcgacaggga gcggttctcg ccgaacaaca tcctgctcat gatcgccggc    720
ggcgggctgc tgtggttggg ctgggccggg ttcaacggcg gcgcgccgta cgcccccaac    780
gtcaccgcca cggtcgccgt gctcaacacc aacgtcagcg ccgcgacgag cctcctcacc    840
tggacctgcc tcgacgtcat cttcttcggc aagccctccg tcatcggcgc cgtgcagggt    900
atgatgacgg ggctcgtctg catcacgccc ggcgccgggc tggtgcacac gtggtcagcg    960
atgctgatgg gcatgttcgc cggcagcgtc ccgtggttca cgatgatgat cctgcacaag   1020
aaatccacct tcctcatgaa ggtcgacgac accctcgccg tcttccacac ccacgccgtc   1080
gccggcatcc tgggcggcgt cctcacgggc ctcctcgcca cgccggagct ctgcgctctc   1140
gattgcccga tcccgaacat gcgcggcgtc ttctacggca cggcatcgg ccagctcggg   1200
aagcagctcg gcggcgcgct gttcgtcacc gtctggaacc tcatcgtcac cagcgccatt   1260
ctcctctgca tcggcctctt catcccgctc cgcatgtccg acgaccagct catgatcggc   1320
gacgacgcgg cgcacgggga ggaggcctac gctctgtggg gggacggtga aagttcgac    1380
gtgacgcggc cggagacgac gaggacggga ggtgcaggcg cgcgggcag ggaggacacc    1440
atggagcaga ggctgaccaa catgggagcc agggtgtca ccattcagtt gtag           1494
```

<210> SEQ ID NO 42
<211> LENGTH: 497
<212> TYPE: PRT
<213> ORGANISM: Oryza sativa

<400> SEQUENCE: 42

```
Met Ala Ser Pro Pro Gln Pro Gly Pro Tyr Met Pro Asp Leu Pro Ala
  1               5                  10                  15

Val Pro Ala Trp Leu Asn Lys Gly Asp Thr Ala Trp Gln Leu Val Ala
             20                  25                  30

Ala Thr Phe Val Gly Ile Gln Ser Met Pro Gly Leu Val Val Ile Tyr
         35                  40                  45

Gly Ser Ile Val Lys Lys Lys Trp Ala Val Asn Ser Ala Phe Met Ala
     50                  55                  60

Leu Tyr Ala Tyr Ala Ser Thr Leu Ile Val Trp Val Leu Val Gly Phe
 65                  70                  75                  80

Arg Met Ala Phe Gly Asp Arg Leu Leu Pro Phe Trp Ala Lys Ala Gly
                 85                  90                  95

Pro Ala Leu Thr Gln Asp Phe Leu Val Gln Arg Ala Val Phe Pro Ala
            100                 105                 110
```

```
Thr Ala His Tyr Gly Ser Asp Gly Thr Leu Glu Thr Pro Arg Thr Glu
        115                 120                 125
Pro Phe Tyr Ala Glu Ala Ala Leu Val Leu Phe Glu Phe Glu Phe Ala
    130                 135                 140
Ala Ile Thr Leu Val Leu Leu Ala Gly Ser Leu Leu Gly Arg Met Asn
145                 150                 155                 160
Ile Lys Ala Trp Met Ala Phe Thr Pro Leu Trp Leu Leu Phe Ser Tyr
                165                 170                 175
Thr Val Gly Ala Phe Ser Leu Trp Gly Gly Phe Leu Tyr Gln Trp
            180                 185                 190
Gly Val Ile Asp Tyr Ser Gly Gly Tyr Val Ile His Leu Ser Ser Gly
        195                 200                 205
Val Ala Gly Phe Thr Ala Ala Tyr Trp Val Gly Pro Arg Leu Lys Ser
    210                 215                 220
Asp Arg Glu Arg Phe Ser Pro Asn Asn Ile Leu Leu Met Ile Ala Gly
225                 230                 235                 240
Gly Gly Leu Leu Trp Leu Gly Trp Ala Gly Phe Asn Gly Gly Ala Pro
                245                 250                 255
Tyr Ala Pro Asn Val Thr Ala Thr Val Ala Val Leu Asn Thr Asn Val
            260                 265                 270
Ser Ala Ala Thr Ser Leu Leu Thr Trp Thr Cys Leu Asp Val Ile Phe
        275                 280                 285
Phe Gly Lys Pro Ser Val Ile Gly Ala Val Gln Gly Met Met Thr Gly
    290                 295                 300
Leu Val Cys Ile Thr Pro Gly Ala Gly Leu Val His Thr Trp Ser Ala
305                 310                 315                 320
Met Leu Met Gly Met Phe Ala Gly Ser Val Pro Trp Phe Thr Met Met
                325                 330                 335
Ile Leu His Lys Lys Ser Thr Phe Leu Met Lys Val Asp Asp Thr Leu
            340                 345                 350
Ala Val Phe His Thr His Ala Val Ala Gly Ile Leu Gly Gly Val Leu
        355                 360                 365
Thr Gly Leu Leu Ala Thr Pro Glu Leu Cys Ala Leu Asp Cys Pro Ile
    370                 375                 380
Pro Asn Met Arg Gly Val Phe Tyr Gly Ser Gly Ile Gly Gln Leu Gly
385                 390                 395                 400
Lys Gln Leu Gly Gly Ala Leu Phe Val Thr Val Trp Asn Leu Ile Val
                405                 410                 415
Thr Ser Ala Ile Leu Leu Cys Ile Gly Leu Phe Ile Pro Leu Arg Met
            420                 425                 430
Ser Asp Asp Gln Leu Met Ile Gly Asp Ala Ala His Gly Glu Glu
        435                 440                 445
Ala Tyr Ala Leu Trp Gly Asp Gly Glu Lys Phe Asp Val Thr Arg Pro
    450                 455                 460
Glu Thr Thr Arg Thr Gly Gly Ala Gly Ala Gly Arg Glu Asp Thr
465                 470                 475                 480
Met Glu Gln Arg Leu Thr Asn Met Gly Ala Arg Gly Val Thr Ile Gln
                485                 490                 495
Leu

<210> SEQ ID NO 43
<211> LENGTH: 1440
<212> TYPE: DNA
<213> ORGANISM: Oryza sativa
```

<400> SEQUENCE: 43

```
atgtcgtcgt cggcgacggt ggtgccgctg gcgtaccagg ggaacacgtc ggcgtcggtg      60
gcggactggc tgaacaaggg cgacaacgcg tggcagctgg tggcggcgac ggtggtgggg     120
ctgcagagcg tgccgggctt ggtggtgctg tacggcggcg tggtgaagaa gaagtgggcg     180
gtgaactcgg cgttcatggc gctctacgcc ttcgccgccg tgtggatctg ctgggtcacc     240
tgggcgtaca acatgtcgtt cggggagaag ctcctcccga tctgggggaa ggcgcggccg     300
gcgctggacc agggcctcct cgtcggccgc gccgcgctgc cggcgacggt ccactaccgc     360
gccgacggca gcgtggagac ggcggcgtg gagccgctgt acccgatggc gacggtggtg      420
tacttccagt gcgtgttcgc cgccatcacc ctcatcctcg tcgccggctc cctcctcggc     480
cgcatgagct tcctcgcctg gatgatcttc gtcccgctct ggctcacctt ctcctacacc     540
gtcggcgcct tctccctctg gggcggcggc ttcctcttcc actggggcgt catcgactac     600
tgcggcggct acgtcatcca cgtctccgcc ggcatcgccg gcttcaccgc cgcctactgg     660
gtggggccaa gggcacagaa ggacagggag aggttcccgc cgaacaacat actgttcacg     720
ctgacggggg cagggttact atggatgggg tgggcagggt tcaacggcgg tggtccgtac     780
gccgccaact ccgtcgcctc catggccgtc ctcaacacca acatctgcac cgccatgagc     840
ctcatcgtct ggacatgcct cgacgtcatc ttcttcaaga agccctccgt cgtcggcgcc     900
gtccagggca tgatcaccgg cctcgtctgc atcaccccg ctgcaggggt ggtgcagggg      960
tgggcggcgc tggtgatggg ggtgctcgcc ggcagcatcc cgtggtacac catgatgatc    1020
ctccacaagc gctccaagat cctgcagcgc gtcgacgaca ccctcggcgt cttccacacc    1080
cacggcgtcg ccggcctcct cggcggcctc ctcaccggcc tcttcgccga ccccaccctc    1140
tgcaacctct tcctccccgt cgccgactcc cggggcgcct tctacggcgg cgccggcggc    1200
gcccagttcg gcaagcagat cgccggtggc ctcttcgtcg tcgcctggaa cgtcgccgtc    1260
acctccctca tctgcctcgc catcaacctc ctcgtcccgc tccgcatgcc cgacgacaag    1320
ctcgaggtcg cgacgacgc cgtccacggc gaggaggcct acgcgctctg ggggcgacggc    1380
gagatgtacg acgtcaccaa gcacggctcc gacgccgccg ttgcgcccgt cgtcgtatga    1440
```

<210> SEQ ID NO 44
<211> LENGTH: 479
<212> TYPE: PRT
<213> ORGANISM: Oryza sativa

<400> SEQUENCE: 44

```
Met Ser Ser Ser Ala Thr Val Val Pro Leu Ala Tyr Gln Gly Asn Thr
  1               5                  10                  15

Ser Ala Ser Val Ala Asp Trp Leu Asn Lys Gly Asp Asn Ala Trp Gln
                 20                  25                  30

Leu Val Ala Ala Thr Val Val Gly Leu Gln Ser Val Pro Gly Leu Val
             35                  40                  45

Val Leu Tyr Gly Gly Val Val Lys Lys Lys Trp Ala Val Asn Ser Ala
         50                  55                  60

Phe Met Ala Leu Tyr Ala Phe Ala Ala Val Trp Ile Cys Trp Val Thr
 65                  70                  75                  80

Trp Ala Tyr Asn Met Ser Phe Gly Glu Lys Leu Leu Pro Ile Trp Gly
                 85                  90                  95

Lys Ala Arg Pro Ala Leu Asp Gln Gly Leu Leu Val Gly Arg Ala Ala
                100                 105                 110
```

```
Leu Pro Ala Thr Val His Tyr Arg Ala Asp Gly Ser Val Glu Thr Ala
        115                 120                 125
Ala Val Glu Pro Leu Tyr Pro Met Ala Thr Val Val Tyr Phe Gln Cys
    130                 135                 140
Val Phe Ala Ala Ile Thr Leu Ile Leu Val Ala Gly Ser Leu Leu Gly
145                 150                 155                 160
Arg Met Ser Phe Leu Ala Trp Met Ile Phe Val Pro Leu Trp Leu Thr
                165                 170                 175
Phe Ser Tyr Thr Val Gly Ala Phe Ser Leu Trp Gly Gly Phe Leu
            180                 185                 190
Phe His Trp Gly Val Ile Asp Tyr Cys Gly Gly Tyr Val Ile His Val
        195                 200                 205
Ser Ala Gly Ile Ala Gly Phe Thr Ala Ala Tyr Trp Val Gly Pro Arg
    210                 215                 220
Ala Gln Lys Asp Arg Glu Arg Phe Pro Pro Asn Asn Ile Leu Phe Thr
225                 230                 235                 240
Leu Thr Gly Ala Gly Leu Leu Trp Met Gly Trp Ala Gly Phe Asn Gly
                245                 250                 255
Gly Gly Pro Tyr Ala Ala Asn Ser Val Ala Ser Met Ala Val Leu Asn
            260                 265                 270
Thr Asn Ile Cys Thr Ala Met Ser Leu Ile Val Trp Thr Cys Leu Asp
        275                 280                 285
Val Ile Phe Phe Lys Lys Pro Ser Val Val Gly Ala Val Gln Gly Met
    290                 295                 300
Ile Thr Gly Leu Val Cys Ile Thr Pro Ala Ala Gly Val Val Gln Gly
305                 310                 315                 320
Trp Ala Ala Leu Val Met Gly Val Leu Ala Gly Ser Ile Pro Trp Tyr
                325                 330                 335
Thr Met Met Ile Leu His Lys Arg Ser Lys Ile Leu Gln Arg Val Asp
            340                 345                 350
Asp Thr Leu Gly Val Phe His Thr His Gly Val Ala Gly Leu Leu Gly
        355                 360                 365
Gly Leu Leu Thr Gly Leu Phe Ala Glu Pro Thr Leu Cys Asn Leu Phe
    370                 375                 380
Leu Pro Val Ala Asp Ser Arg Gly Ala Phe Tyr Gly Gly Ala Gly Gly
385                 390                 395                 400
Ala Gln Phe Gly Lys Gln Ile Ala Gly Gly Leu Phe Val Val Ala Trp
                405                 410                 415
Asn Val Ala Val Thr Ser Leu Ile Cys Leu Ala Ile Asn Leu Leu Val
            420                 425                 430
Pro Leu Arg Met Pro Asp Asp Lys Leu Glu Val Gly Asp Asp Ala Val
        435                 440                 445
His Gly Glu Glu Ala Tyr Ala Leu Trp Gly Asp Gly Glu Met Tyr Asp
    450                 455                 460
Val Thr Lys His Gly Ser Asp Ala Ala Val Ala Pro Val Val Val
465                 470                 475

<210> SEQ ID NO 45
<211> LENGTH: 1497
<212> TYPE: DNA
<213> ORGANISM: Oryza sativa

<400> SEQUENCE: 45
atgtcggggg acgcgttcaa catgtcggtg gcgtaccagc cgtcggggat ggcggtgccg    60
gagtggctga acaagggcga caacgcgtgg cagatgatct cggcgacgct ggtggggatg   120
```

```
cagagcgtgc cggggctggt gatcctgtac ggcagcatcg tgaagaagaa gtgggcggtg      180
aactcggcgt tcatggcgct ctacgccttc gccgccgtgt ggctgtgctg ggtcacctgg      240
ggctacaaca tgtcgttcgg ccacaagctc ctcccgttct ggggcaaggc gcggccggcg      300
ctgggccaga gcttcctcct cgcccaggcc gtgctcccgc agacgacgca gttctacaag      360
ggcggcggcg cgccgacgc cgtggtggag acgccatggg tgaacccgct ctacccgatg       420
gccaccatgg tgtacttcca gtgcgtgttc gccgccatca cgctcatcct cctcgccggc      480
tcgctgctgg ggcggatgaa catcaaggcg tggatgctgt cgtcccgct ctggctcacc       540 ttctcctaca ccgtcggcgc cttctcgctg tggggcggcg gcttcctctt ccactggggg      600
gtcatggact actccggcgg ctacgtcatc cacctctcgt cgggtgtcgc cggcttcacc      660
gcggcgtact gggtggggcc caggtcgacc aaggacaggg agaggttccc gccaaacaac      720
gtgctgctca tgctcaccgg cgccggcata ctgtggatgg ggtgggcggg gttcaacggc      780
ggcgacccgt actccgccaa catcgactcc tcgctcgccg tgctcaacac caacatctgc      840
gccgccacca gcctcctcgt ctggacttgc ctcgacgtca tcttcttcaa gaagccgtcc      900
gtcatcggcg ccgtccaggg catgatcacc ggcctcgtct gcatcactcc cggcgcaggc      960
ctggtgcagg gttgggcggc gatcgtgatg ggcatcctct ccggcagcat cccgtggttc     1020
acgatgatgg tggtgcacaa gcggtcgcgc tcctgcagc aggtggacga cacctgggc      1080 gtcttccaca cccacgccgt cgccggattc ctcggcggcg ccaccacggg cctcttcgcc     1140
gagcccgtcc tctgctcctt cttcctcccc gtcaccaact cccgcggcgc cttctacccc     1200
ggccgcggcg cggcctcca gttcgtccgc caggtggccg cgccctcttt catcatctgc     1260
tggaacgtgg tggtcaccag cctcgtctgc ctcgccgtcc cgccgtggt tcccctccgg     1320 atgcccgagg aggagctcgc catcggcgac gacgccgtgc acggggagga ggcgtacgcg     1380
ctgtggggcg acggcgagaa gtacgactcc accaagcacg gatggtactc cgacaacaac     1440
gacacgcacc acaacaacaa caaggccgcg cccagcggcg tcacgcagaa cgtctga       1497

<210> SEQ ID NO 46
<211> LENGTH: 498
<212> TYPE: PRT
<213> ORGANISM: Oryza sativa

<400> SEQUENCE: 46

Met Ser Gly Asp Ala Phe Asn Met Ser Val Ala Tyr Gln Pro Ser Gly
 1               5                  10                  15

Met Ala Val Pro Glu Trp Leu Asn Lys Gly Asp Asn Ala Trp Gln Met
            20                  25                  30

Ile Ser Ala Thr Leu Val Gly Met Gln Ser Val Pro Gly Leu Val Ile
        35                  40                  45

Leu Tyr Gly Ser Ile Val Lys Lys Lys Trp Ala Val Asn Ser Ala Phe
    50                  55                  60

Met Ala Leu Tyr Ala Phe Ala Ala Val Trp Leu Cys Trp Val Thr Trp
65                  70                  75                  80

Gly Tyr Asn Met Ser Phe Gly His Lys Leu Leu Pro Phe Trp Gly Lys
                85                  90                  95

Ala Arg Pro Ala Leu Gly Gln Ser Phe Leu Leu Ala Gln Ala Val Leu
            100                 105                 110

Pro Gln Thr Thr Gln Phe Tyr Lys Gly Gly Gly Gly Ala Asp Ala Val
        115                 120                 125

Val Glu Thr Pro Trp Val Asn Pro Leu Tyr Pro Met Ala Thr Met Val
```

```
                130                 135                 140
Tyr Phe Gln Cys Val Phe Ala Ala Ile Thr Leu Ile Leu Leu Ala Gly
145                 150                 155                 160

Ser Leu Leu Gly Arg Met Asn Ile Lys Ala Trp Met Leu Phe Val Pro
                165                 170                 175

Leu Trp Leu Thr Phe Ser Tyr Thr Val Gly Ala Phe Ser Leu Trp Gly
            180                 185                 190

Gly Gly Phe Leu Phe His Trp Gly Val Met Asp Tyr Ser Gly Gly Tyr
            195                 200                 205

Val Ile His Leu Ser Ser Gly Val Ala Gly Phe Thr Ala Ala Tyr Trp
210                 215                 220

Val Gly Pro Arg Ser Thr Lys Asp Arg Glu Arg Phe Pro Pro Asn Asn
225                 230                 235                 240

Val Leu Leu Met Leu Thr Gly Ala Gly Ile Leu Trp Met Gly Trp Ala
                245                 250                 255

Gly Phe Asn Gly Gly Asp Pro Tyr Ser Ala Asn Ile Asp Ser Ser Leu
            260                 265                 270

Ala Val Leu Asn Thr Asn Ile Cys Ala Ala Thr Ser Leu Leu Val Trp
            275                 280                 285

Thr Cys Leu Asp Val Ile Phe Phe Lys Lys Pro Ser Val Ile Gly Ala
290                 295                 300

Val Gln Gly Met Ile Thr Gly Leu Val Cys Ile Thr Pro Gly Ala Gly
305                 310                 315                 320

Leu Val Gln Gly Trp Ala Ala Ile Val Met Gly Ile Leu Ser Gly Ser
                325                 330                 335

Ile Pro Trp Phe Thr Met Met Val Val His Lys Arg Ser Arg Leu Leu
            340                 345                 350

Gln Gln Val Asp Asp Thr Leu Gly Val Phe His Thr His Ala Val Ala
            355                 360                 365

Gly Phe Leu Gly Gly Ala Thr Thr Gly Leu Phe Ala Glu Pro Val Leu
            370                 375                 380

Cys Ser Leu Phe Leu Pro Val Thr Asn Ser Arg Gly Ala Phe Tyr Pro
385                 390                 395                 400

Gly Arg Gly Gly Gly Leu Gln Phe Val Arg Gln Val Ala Gly Ala Leu
                405                 410                 415

Phe Ile Ile Cys Trp Asn Val Val Thr Ser Leu Val Cys Leu Ala
            420                 425                 430

Val Arg Ala Val Val Pro Leu Arg Met Pro Glu Glu Leu Ala Ile
                435                 440                 445

Gly Asp Asp Ala Val His Gly Glu Glu Ala Tyr Ala Leu Trp Gly Asp
450                 455                 460

Gly Glu Lys Tyr Asp Ser Thr Lys His Gly Trp Tyr Ser Asp Asn Asn
465                 470                 475                 480

Asp Thr His His Asn Asn Lys Ala Ala Pro Ser Gly Val Thr Gln
                485                 490                 495

Asn Val

<210> SEQ ID NO 47
<211> LENGTH: 1497
<212> TYPE: DNA
<213> ORGANISM: Oryza sativa

<400> SEQUENCE: 47
atggcgacgt gcgcggcgga cctggcgccg ctgctggggc cggtggcggc gaacgcgacg      60
```

-continued

```
gactacctgt gcaaccggtt cgccgacacg acgtcggcgg tggacgcgac gtacctgctc    120
ttctcggcgt acctcgtgtt cgccatgcag ctcgggttcg cgatgctctg cgccgggtcg    180
gtgcgggcca agaacacgat gaacatcatg ctcaccaacg tgctcgacgc cgcggccggg    240
gcgctcttct actacctctt cggcttcgcc ttcgccttcg gcacgccgtc caacggcttc    300
atcgggaagc agttcttcgg cctcaagcac atgccgcaga ccgggttcga ctacgacttc    360
ttcctcttcc agtgggcctt cgccatcgcc gccgccggga tcacgtcggg ctccatcgcc    420
gagaggacgc agttcgtcgc ctacctcatc tactccgcct tcctcaccgg gttcgtctac    480
ccggtggtgt cccactggat ctggtccgcc gatgggtggg cctctgcctc cgcacgtcc    540 ggacctctgc tgttcggctc cggtgtcatc gacttcgccg gctccggcgt cgtccacatg    600
gtcggcggtg tcgccgggct ctggggcgcg ctcatcgagg cccccgcat cgggaggttc    660 gaccacgccg gccgatcggt ggcgctcaag ggccacagcg cgtcgctcgt cgtgcttggc    720
accttcctgc tgtggttcgg ctggtacgga ttcaaccccg gtcgttcac caccatcctc    780 aagacgtacg gcccggccgg cggcatcaac gggcagtggt ccggagtcgg ccgcaccgcc    840
gtgacgacga ccctggccgg cagcgtggcg gcgctcacca cgctgttcgg gaagcggctc    900
cagacggggc actggaacgt ggtcgacgtc tgcaacggcc tcctcggcgg gttcgccgcc    960
atcaccgccg ggtgcagcgt cgtcgacccg tgggccgcga tcatctgcgg gttcgtctcg   1020
gcgtgggtgc tcatcggcct caacgcgctc gccgcgcgcc tcaagttcga cgacccgctc   1080
gaggccgccc agctccacgg cgggtgcggc gcgtggggga tcctcttcac cgcgctcttc   1140
gcgaggcaga agtacgtcga ggagatctac ggcgccggcc ggccgtacgg cctgttcatg   1200
ggcggcggcg gcaagctgct cgccgcgcac gtcatccaga tcctggtcat cttcgggtgg   1260
gtcagctgca ccatgggacc tctcttctac gggctcaaga agctcggcct gctccgcatc   1320
tccgccgagg acgagacgtc cggcatggac ctgacacggc acggcgggtt cgcgtacgtc   1380
taccacgacg aggacgagca cgacaagtct ggggttggtg ggttcatgct ccggtccgcg   1440
cagacccgcg tcgagccggc ggcggcggct gcctccaaca gcaacaacca agtgtaa     1497
```

<210> SEQ ID NO 48
<211> LENGTH: 498
<212> TYPE: PRT
<213> ORGANISM: Oryza sativa

<400> SEQUENCE: 48

```
Met Ala Thr Cys Ala Ala Asp Leu Ala Pro Leu Leu Gly Pro Val Ala
  1               5                  10                  15

Ala Asn Ala Thr Asp Tyr Leu Cys Asn Arg Phe Ala Asp Thr Thr Ser
             20                  25                  30

Ala Val Asp Ala Thr Tyr Leu Leu Phe Ser Ala Tyr Leu Val Phe Ala
         35                  40                  45

Met Gln Leu Gly Phe Ala Met Leu Cys Ala Gly Ser Val Arg Ala Lys
     50                  55                  60

Asn Thr Met Asn Ile Met Leu Thr Asn Val Leu Asp Ala Ala Ala Gly
 65                  70                  75                  80

Ala Leu Phe Tyr Tyr Leu Phe Gly Phe Ala Phe Ala Phe Gly Thr Pro
                 85                  90                  95

Ser Asn Gly Phe Ile Gly Lys Gln Phe Phe Gly Leu Lys His Met Pro
            100                 105                 110

Gln Thr Gly Phe Asp Tyr Asp Phe Phe Leu Phe Gln Trp Ala Phe Ala
        115                 120                 125
```

```
Ile Ala Ala Gly Ile Thr Ser Gly Ser Ile Ala Glu Arg Thr Gln
130                 135                 140

Phe Val Ala Tyr Leu Ile Tyr Ser Ala Phe Leu Thr Gly Phe Val Tyr
145                 150                 155                 160

Pro Val Val Ser His Trp Ile Trp Ser Ala Asp Gly Trp Ala Ser Ala
                165                 170                 175

Ser Arg Thr Ser Gly Pro Leu Leu Phe Gly Ser Gly Val Ile Asp Phe
            180                 185                 190

Ala Gly Ser Gly Val Val His Met Val Gly Gly Val Ala Gly Leu Trp
        195                 200                 205

Gly Ala Leu Ile Glu Gly Pro Arg Ile Gly Arg Phe Asp His Ala Gly
210                 215                 220

Arg Ser Val Ala Leu Lys Gly His Ser Ala Ser Leu Val Val Leu Gly
225                 230                 235                 240

Thr Phe Leu Leu Trp Phe Gly Trp Tyr Gly Phe Asn Pro Gly Ser Phe
                245                 250                 255

Thr Thr Ile Leu Lys Thr Tyr Gly Pro Ala Gly Gly Ile Asn Gly Gln
            260                 265                 270

Trp Ser Gly Val Gly Arg Thr Ala Val Thr Thr Thr Leu Ala Gly Ser
        275                 280                 285

Val Ala Ala Leu Thr Thr Leu Phe Gly Lys Arg Leu Gln Thr Gly His
290                 295                 300

Trp Asn Val Val Asp Val Cys Asn Gly Leu Leu Gly Gly Phe Ala Ala
305                 310                 315                 320

Ile Thr Ala Gly Cys Ser Val Val Asp Pro Trp Ala Ala Ile Ile Cys
                325                 330                 335

Gly Phe Val Ser Ala Trp Val Leu Ile Gly Leu Asn Ala Leu Ala Ala
            340                 345                 350

Arg Leu Lys Phe Asp Asp Pro Leu Glu Ala Ala Gln Leu His Gly Gly
        355                 360                 365

Cys Gly Ala Trp Gly Ile Leu Phe Thr Ala Leu Phe Ala Arg Gln Lys
370                 375                 380

Tyr Val Glu Glu Ile Tyr Gly Ala Gly Arg Pro Tyr Gly Leu Phe Met
385                 390                 395                 400

Gly Gly Gly Gly Lys Leu Leu Ala Ala His Val Ile Gln Ile Leu Val
                405                 410                 415

Ile Phe Gly Trp Val Ser Cys Thr Met Gly Pro Leu Phe Tyr Gly Leu
            420                 425                 430

Lys Lys Leu Gly Leu Leu Arg Ile Ser Ala Glu Asp Glu Thr Ser Gly
        435                 440                 445

Met Asp Leu Thr Arg His Gly Gly Phe Ala Tyr Val Tyr His Asp Glu
450                 455                 460

Asp Glu His Asp Lys Ser Gly Val Gly Gly Phe Met Leu Arg Ser Ala
465                 470                 475                 480

Gln Thr Arg Val Glu Pro Ala Ala Ala Ala Ser Asn Ser Asn Asn
                485                 490                 495

Gln Val

<210> SEQ ID NO 49
<211> LENGTH: 438
<212> TYPE: DNA
<213> ORGANISM: Oryza sativa

<400> SEQUENCE: 49
atggcgtggg tgagcttcac catggcgctg ctgttcctgg tgctcaacaa gctgggcttg    60
```

```
ctgcgcatct cggccgagga caagatggcc ggcatggacc agacgcgcca cggcgggtta    120
ccacgacgac gacgcgagcg gcaagccaga ccttggcatt ggcgggttca tgctcaagtc    180
ggtgcacggc acgcaggttc gtcggtgtcg acggaggcga cgactgcggg gatggtggcc    240
gcgagggccg tgcaggagtt gtggaacggt cggacaccag cagaagagga catacccca    300 ccggttctgc tcgccggaga gggaggggac aacgactgcg gtgtccatca ctggctgcgc    360
ttgccactac catcgctggt ctcgtggaag agaggagagg ggagaaagag gaagaagaag    420
gaaagaaggg caatttga                                                  438
```

```
<210> SEQ ID NO 50
<211> LENGTH: 145
<212> TYPE: PRT
<213> ORGANISM: Oryza sativa

<400> SEQUENCE: 50

Met Ala Trp Val Ser Phe Thr Met Ala Leu Leu Phe Leu Val Leu Asn
  1               5                  10                  15

Lys Leu Gly Leu Leu Arg Ile Ser Ala Glu Asp Lys Met Ala Gly Met
             20                  25                  30

Asp Gln Thr Arg His Gly Gly Leu Pro Arg Arg Arg Glu Arg Gln
         35                  40                  45

Ala Arg Pro Trp His Trp Arg Val His Ala Gln Val Gly Ala Arg His
     50                  55                  60

Ala Gly Ser Ser Val Ser Thr Glu Ala Thr Thr Ala Gly Met Val Ala
 65                  70                  75                  80

Ala Arg Ala Val Gln Glu Leu Trp Asn Gly Ser Asp Thr Glu Gln Lys
                 85                  90                  95

Arg Thr Tyr Pro Pro Val Leu Leu Ala Gly Glu Gly Asp Asn Asp
            100                 105                 110

Cys Gly Val His His Trp Leu Arg Leu Pro Leu Pro Ser Leu Val Ser
        115                 120                 125

Trp Lys Arg Gly Glu Gly Arg Lys Arg Lys Lys Glu Arg Arg Ala
    130                 135                 140

Ile
145
```

```
<210> SEQ ID NO 51
<211> LENGTH: 1497
<212> TYPE: DNA
<213> ORGANISM: Oryza sativa

<400> SEQUENCE: 51
atggcgacgt gcttggacag cctcgggccg ctgctcggcg gcgcggcgaa ctccaccgac     60
gcggccaact acatctgcaa caggttcacg gacacctcct ccgcggtgga cgcgacgtac    120
ctgctcttct cggcctacct cgtgttcgcc atgcagctcg ggttcgccat gctctgcgcg    180
ggctccgtcc gcgccaagaa ctccatgaac atcatgctca ccaacgtgct cgacgccgcc    240 gccgcgcgc tcttctacta cctcttcggc ttcgccttcg cgttcgggac gccgtccaag    300
ggcttcatcg gaagcagtt cttcgggctg aagcacatgc gcagacagg gtacgactac    360 gacttcttcc tcttccagtg ggccttcgcc atcgccgccg ccggcatcac gtccggttcc    420
atcgccgagc ggacgcgctt cagcgcgtat ctcatctact ccgccttcct caccgggttc    480
gtgtacccgg tggtgtcgca ctggttctgg tccaccgacg gtgggcttc ggccggccgg    540 ttgacgggtc cgttgctgtt caagtcgggc gtcatcgact cgccggctc cggcgtcgtc    600
```

```
catctggtcg gtggcattgc tggcctgtgg ggtgccttca tcgagggccc tcgcatcggg    660
cggttcgacg ccgccggccg cacggtggcg atgaaagggc acagcgcctc actggtcgtg    720
ctcggcacct tcctgctgtg gttcgggtgg ttcggcttca acccgggtc cttcaccacc     780 atctccaaga tctacggcga gtcgggcacg atcgacgggc agtggtcggc ggtgggccgc    840
accgccgtga cgacgtcgct ggcggggagc gtcgccgcgc tgacgacgct ctacggcaag    900
agatggctga cggggcactg gaacgtgacc gacgtctgca acggtctcct cggcggcttc    960
gccgcgatca ccgcgggctg ctccgtggtc gacccgtggg cgtcggtgat ctgcgggttc   1020
gtgtcggcgt gggtcctcat cggctgcaac aagctgtcgc tgattctcaa gttcgacgac   1080
ccgctggagg cgacgcagct gcacgccggg tgcggcgcgt gggggatcat cttcaccgcg   1140
ctgttcgcgc gcagggagta cgtcgagctg atctacgggg tgccggggag gccgtacggg   1200
ctgttcatgg gcggcggcgg gaggcttctc gcggcgcaca tcgtgcagat cctggtgatc   1260
gtcgggtggg tcagcgccac catggggacg ctcttctacg tgctgcacag gttcgggctg   1320
ctccgcgtct cgcccgcgac agagatggaa ggcatggacc cgacgtgcca cggcgggttc   1380
gggtacgtga acgaggacga aggcgagcgc cgcgtcaggg ccaagtcggc ggcggagacg   1440
gctcgcgtgg agcccagaaa gtcgccggag caagccgcgg cgggccagtt tgtgtag     1497

<210> SEQ ID NO 52
<211> LENGTH: 498
<212> TYPE: PRT
<213> ORGANISM: Oryza sativa

<400> SEQUENCE: 52

Met Ala Thr Cys Leu Asp Ser Leu Gly Pro Leu Leu Gly Gly Ala Ala
 1                5                  10                  15

Asn Ser Thr Asp Ala Ala Asn Tyr Ile Cys Asn Arg Phe Thr Asp Thr
             20                  25                  30

Ser Ser Ala Val Asp Ala Thr Tyr Leu Leu Phe Ser Ala Tyr Leu Val
         35                  40                  45

Phe Ala Met Gln Leu Gly Phe Ala Met Leu Cys Ala Gly Ser Val Arg
     50                  55                  60

Ala Lys Asn Ser Met Asn Ile Met Leu Thr Asn Val Leu Asp Ala Ala
 65                  70                  75                  80

Ala Gly Ala Leu Phe Tyr Tyr Leu Phe Gly Phe Ala Phe Ala Phe Gly
                 85                  90                  95

Thr Pro Ser Lys Gly Phe Ile Gly Lys Gln Phe Gly Leu Lys His
            100                 105                 110

Met Pro Gln Thr Gly Tyr Asp Tyr Asp Phe Phe Leu Phe Gln Trp Ala
        115                 120                 125

Phe Ala Ile Ala Ala Ala Gly Ile Thr Ser Gly Ser Ile Ala Glu Arg
    130                 135                 140

Thr Arg Phe Ser Ala Tyr Leu Ile Tyr Ser Ala Phe Leu Thr Gly Phe
145                 150                 155                 160

Val Tyr Pro Val Val Ser His Trp Phe Trp Ser Thr Asp Gly Trp Ala
                165                 170                 175

Ser Ala Gly Arg Leu Thr Gly Pro Leu Leu Phe Lys Ser Gly Val Ile
            180                 185                 190

Asp Phe Ala Gly Ser Gly Val Val His Leu Val Gly Gly Ile Ala Gly
        195                 200                 205

Leu Trp Gly Ala Phe Ile Glu Gly Pro Arg Ile Gly Arg Phe Asp Ala
    210                 215                 220
```

```
Ala Gly Arg Thr Val Ala Met Lys Gly His Ser Ala Ser Leu Val Val
225                 230                 235                 240

Leu Gly Thr Phe Leu Leu Trp Phe Gly Trp Phe Gly Phe Asn Pro Gly
            245                 250                 255

Ser Phe Thr Thr Ile Ser Lys Ile Tyr Gly Glu Ser Gly Thr Ile Asp
        260                 265                 270

Gly Gln Trp Ser Ala Val Gly Arg Thr Ala Val Thr Thr Ser Leu Ala
    275                 280                 285

Gly Ser Val Ala Ala Leu Thr Thr Leu Tyr Gly Lys Arg Trp Leu Thr
290                 295                 300

Gly His Trp Asn Val Thr Asp Val Cys Asn Gly Leu Leu Gly Gly Phe
305                 310                 315                 320

Ala Ala Ile Thr Ala Gly Cys Ser Val Val Asp Pro Trp Ala Ser Val
            325                 330                 335

Ile Cys Gly Phe Val Ser Ala Trp Val Leu Ile Gly Cys Asn Lys Leu
        340                 345                 350

Ser Leu Ile Leu Lys Phe Asp Asp Pro Leu Glu Ala Thr Gln Leu His
    355                 360                 365

Ala Gly Cys Gly Ala Trp Gly Ile Ile Phe Thr Ala Leu Phe Ala Arg
370                 375                 380

Arg Glu Tyr Val Glu Leu Ile Tyr Gly Val Pro Gly Arg Pro Tyr Gly
385                 390                 395                 400

Leu Phe Met Gly Gly Gly Gly Arg Leu Leu Ala Ala His Ile Val Gln
            405                 410                 415

Ile Leu Val Ile Val Gly Trp Val Ser Ala Thr Met Gly Thr Leu Phe
        420                 425                 430

Tyr Val Leu His Arg Phe Gly Leu Leu Arg Val Ser Pro Ala Thr Glu
    435                 440                 445

Met Glu Gly Met Asp Pro Thr Cys His Gly Gly Phe Gly Tyr Val Asp
450                 455                 460

Glu Asp Glu Gly Glu Arg Arg Val Arg Ala Lys Ser Ala Ala Glu Thr
465                 470                 475                 480

Ala Arg Val Glu Pro Arg Lys Ser Pro Glu Gln Ala Ala Ala Gly Gln
            485                 490                 495

Phe Val

<210> SEQ ID NO 53
<211> LENGTH: 1853
<212> TYPE: DNA
<213> ORGANISM: Oryza sativa

<400> SEQUENCE: 53
acagcccaca cttccattgc tcctcccctc tcctctacag tctgtgttga gcgcgcgtcg      60
aggcggcgag gatggcaacg tgcgcggata ccctcggccc gctgctgggc acggcggcgg     120
cgaacgcgac ggactacctg tgcaaccagt tcgcggacac gacgtcggcc gtggactcga     180
cgtacctgct cttctcggcg tacctcgtgt tcgccatgca gctcggcttc gccatgctct     240
gcgccgggtc cgtccgcgcc aagaacacca tgaacatcat gcttaccaac gtgctcgacg     300
ccgccgccgg cgcgctcttc tactacctct tcggcttcgc cttcgccttc ggggcgccgt     360
ccaacggctt catcgggaag cacttcttcg gcctcaagca ggtcccacag gtcggcttcg     420
actacagctt cttcctcttc cagtgggcct tcgccatcgc cgccgcgggc atcacgtccg     480
gctccatcgc cgagcggacc cagttcgtgg cgtacctcat ctactccgcc ttcctcaccg     540
```

```
gcttcgtcta cccggtggtg tcccactgga tctggtccgc cgacgggtgg gcctcggctt    600
cccggacgtc ggggtcgctg ctcttcgggt ccggcgtcat cgactcgcc  gggtcagggg    660
ttgtccacat ggtgggcggc gtggccggac tctgggcgc  cctcatcgag gccccccgca    720
ttgggcggtt cgaccacgcc ggccgctcgg tggcgctgcg cggccacagc gcgtcgctcg    780
tcgtgctcgg cagcttcctt ctgtggttcg ggtggtacgg gtttaacccc ggctcgttcc    840
tcaccatcct caaatcctac ggcccgcccg gtagcatcca cgggcagtgg tcggcggtgg    900
gacgcaccgc cgtgaccacc accctcgccg gcagcacggc ggcgctcacg acgctcttcg    960
ggaagaggct ccagacgggg cactggaacg tgatcgacgt ctgcaacggc ctcctcggcg   1020
gcttcgcggc gatcaccgcc ggttgctccg tcgtcgaccc gtgggccgcg atcatctgcg   1080
ggttcgtctc ggcgtgggtg ctcatcggcc tcaacgcgct ggcggcgagg ctcaagttcg   1140
acgacccgct cgaggcggcg cagctgcacg gcgggtgcgg cgcgtggggg gtcatcttca   1200
cggcgctgtt cgcgcgcaag gagtacgtgg accagatctt cggccagccc gggcgcccgt   1260
acgggctgtt catgggcggc ggcggccggc tgctcggggc gcacatagtg gtcatcctgg   1320
tcatcgcggc gtgggtgagc ttcaccatgg cgccgctgtt cctggtgctc aacaagctgg   1380
gcttgctgcg catctcggcc gaggacgaga tggccggcat ggaccagacg cgccacggcg   1440
ggttcgcgta cgcgtaccac gacgacgacg cgagcggcaa gccggaccgc agcgtcggcg   1500
ggttcatgct caagtcggcg cacggcacgc aggtcgccgc cgagatggga ggccatgtct   1560
agtggaaccg gaggagctga gctagtagta catacatgca gcatcatcga tcgaacgaaa   1620
tgcatataag cgttttttcaa ggttgatctg atgctgcagg tttcgtgatt gtataatagg   1680
aagaaaaaga tagtagtatt ttttatctga gatcatctgt ttggaacagg ggatttgact   1740
aagatttgat ataaatttac acaaaatctt agcaaaaatc cctttatctc aactctcaag   1800
tagagctttg ctttgtacaa caaagtatca tgtgtgatat aattgtcagg tgg          1853
```

<210> SEQ ID NO 54
<211> LENGTH: 496
<212> TYPE: PRT
<213> ORGANISM: Oryza sativa

<400> SEQUENCE: 54

Met Ala Thr Cys Ala Asp Thr Leu Gly Pro Leu Gly Thr Ala Ala
1               5                   10                  15

Ala Asn Ala Thr Asp Tyr Leu Cys Asn Gln Phe Ala Asp Thr Thr Ser
            20                  25                  30

Ala Val Asp Ser Thr Tyr Leu Leu Phe Ser Ala Tyr Leu Val Phe Ala
        35                  40                  45

Met Gln Leu Gly Phe Ala Met Leu Cys Ala Gly Ser Val Arg Ala Lys
    50                  55                  60

Asn Thr Met Asn Ile Met Leu Thr Asn Val Leu Asp Ala Ala Ala Gly
65                  70                  75                  80

Ala Leu Phe Tyr Tyr Leu Phe Gly Phe Ala Phe Ala Phe Gly Ala Pro
                85                  90                  95

Ser Asn Gly Phe Ile Gly Lys His Phe Phe Gly Leu Lys Gln Val Pro
            100                 105                 110

Gln Val Gly Phe Asp Tyr Ser Phe Phe Leu Phe Gln Trp Ala Phe Ala
        115                 120                 125

Ile Ala Ala Ala Gly Ile Thr Ser Gly Ser Ile Ala Glu Arg Thr Gln
    130                 135                 140

Phe Val Ala Tyr Leu Ile Tyr Ser Ala Phe Leu Thr Gly Phe Val Tyr

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Pro Val Val Ser His Trp Ile Trp Ser Ala Asp Gly Trp Ala Ser Ala
                165                 170                 175

Ser Arg Thr Ser Gly Ser Leu Leu Phe Gly Ser Gly Val Ile Asp Phe
            180                 185                 190

Ala Gly Ser Gly Val Val His Met Val Gly Val Ala Gly Leu Trp
        195                 200                 205

Gly Ala Leu Ile Glu Gly Pro Arg Ile Gly Arg Phe Asp His Ala Gly
    210                 215                 220

Arg Ser Val Ala Leu Arg Gly His Ser Ala Ser Leu Val Val Leu Gly
225                 230                 235                 240

Ser Phe Leu Leu Trp Phe Gly Trp Tyr Gly Phe Asn Pro Gly Ser Phe
                245                 250                 255

Leu Thr Ile Leu Lys Ser Tyr Gly Pro Pro Gly Ser Ile His Gly Gln
            260                 265                 270

Trp Ser Ala Val Gly Arg Thr Ala Val Thr Thr Thr Leu Ala Gly Ser
        275                 280                 285

Thr Ala Ala Leu Thr Thr Leu Phe Gly Lys Arg Leu Gln Thr Gly His
    290                 295                 300

Trp Asn Val Ile Asp Val Cys Asn Gly Leu Leu Gly Gly Phe Ala Ala
305                 310                 315                 320

Ile Thr Ala Gly Cys Ser Val Val Asp Pro Trp Ala Ala Ile Ile Cys
                325                 330                 335

Gly Phe Val Ser Ala Trp Val Leu Ile Gly Leu Asn Ala Leu Ala Ala
            340                 345                 350

Arg Leu Lys Phe Asp Asp Pro Leu Glu Ala Ala Gln Leu His Gly Gly
        355                 360                 365

Cys Gly Ala Trp Gly Val Ile Phe Thr Ala Leu Phe Ala Arg Lys Glu
    370                 375                 380

Tyr Val Asp Gln Ile Phe Gly Gln Pro Gly Arg Pro Tyr Gly Leu Phe
385                 390                 395                 400

Met Gly Gly Gly Gly Arg Leu Leu Gly Ala His Ile Val Val Ile Leu
                405                 410                 415

Val Ile Ala Ala Trp Val Ser Phe Thr Met Ala Pro Leu Phe Leu Val
            420                 425                 430

Leu Asn Lys Leu Gly Leu Leu Arg Ile Ser Ala Glu Asp Glu Met Ala
        435                 440                 445

Gly Met Asp Gln Thr Arg His Gly Gly Phe Ala Tyr Ala Tyr His Asp
    450                 455                 460

Asp Asp Ala Ser Gly Lys Pro Asp Arg Ser Val Gly Phe Met Leu
465                 470                 475                 480

Lys Ser Ala His Gly Thr Gln Val Ala Ala Glu Met Gly Gly His Val
                485                 490                 495

<210> SEQ ID NO 55
<211> LENGTH: 1870
<212> TYPE: DNA
<213> ORGANISM: Oryza sativa

<400> SEQUENCE: 55
cactagtact ccctccgtcc caatataagt gcatttagga caggatgtga tatatcctag    60
gactacaaat ctggacagtt gtctgttcat attcgtagtc ctaggatatg tcacatacta   120
tactaggtgt atttatattg ggacggaggg agcagtactt aaagtatatt tgcaactttt   180
tactgaactt ggtgtgctgt gtcaggcgac tactccagag gattgattac ttcatgcctt   240

```
gacaatgatg tgaagtagca tgaccttgcg attcatatgg tcggggatcg aggcatatat      300
acacccaacc cagttcattg agtgatcagt agagagattc ttcccctctt ctcctgccag      360
ctcttccagg ttctgagttc tgaccatggc ggctggagcg attccaatgg cgtaccagac      420
cactccgtca tcgccagact ggctgaacaa gggcgacaac gcatggcaga tgacatcggc      480
gaccctcgtc ggcctgcaga gcatgccagg gctggtgatc ctgtacggca gcattgtcaa      540
gaagaagtgg gctatcaact cggcgttcat ggcgctgtat gccttcgctg ctgtctggat      600
ctgctgggtt gtctgggcat acaacatgtc gttcggcgac cgcctcctgc cattctgggg      660
taaggcacgg ccagcgctcg ggcagagctt cctcgtggcg cagtctgagc tcactgctac      720
cgctattcgc taccacaatg gtcagctgag ggcgcccatg ctcaagccgt tgtacccagt      780
cgccaccatg gtgtacttcc agtgcatgtt tgcgagcatc accatcatca tcctcgcagg      840
ctcactgctt gggcgcatga acatcaaggc gtggatggcc tttgtgccgc tctggatcac      900
cttctcttac acggtctgcg ccttctcgct ctggggtggc ggtttcctct tccagtgggg      960
tgtcatagac tactctggtg ctatgtcat ccatctctct tctggcatcg caggcctcac     1020
tgctgcctac tgggttggac caaggtcagc atcagatagg gagagattcc cgcccaacaa     1080
catactgctg gtgctagcag gggcggggct gctgtggctt gggtggacag gtttcaatgg     1140
aggagaccca tattcagcca atattgattc atccatggca gtgctcaaca cacatatctg     1200
cgcatccacc agcctactcg tgtggacaat cctggatgtc ttcttcttcg ggaagccatc     1260
ggtaattggc gcggtgcagg gcatgatcac tggcctggta tgcatcaccc ctggtgcagg     1320
cctggtgcaa ggttgggcag ctattgtgat gggaattctc tctggtagca ttccatggta     1380
caccatgatg gtgctgcaca agaaatggtc attcatgcag aggattgatg acacgcttgg     1440
tgtcttccac acccatgcgg tggctgggtt ccttggtggc gccaccactg gactcttcgc     1500
cgagcccatc ctatgcagtc tcttcctatc tatcccagat tctaaaggtg cattctacgg     1560
tggccccggt ggatcacagt tcgggaagca gattgctggc gcactatttg tcactgcctg     1620
gaatattgtt atcacctcca tcatctgtgt catcatcagc ctaatcctgc ccctccgtat     1680
agctgatcaa gaactgctta ttggagatga tgctgtacac ggtgaggagg catatgctat     1740
ctgggcagag ggagagctca atgacatgac ccaccacaat gagagcacac atagtggtgt     1800
ctctgtagga gtgacacaga atgtttgaac agtacccact ttattgagga aaagaaata     1860 taattgtctt                                                            1870
```

<210> SEQ ID NO 56
<211> LENGTH: 480
<212> TYPE: PRT
<213> ORGANISM: Oryza sativa

<400> SEQUENCE: 56

Met Ala Ala Gly Ala Ile Pro Met Ala Tyr Gln Thr Thr Pro Ser Ser
 1               5                  10                  15

Pro Asp Trp Leu Asn Lys Gly Asp Asn Ala Trp Gln Met Thr Ser Ala
            20                  25                  30

Thr Leu Val Gly Leu Gln Ser Met Pro Gly Leu Val Ile Leu Tyr Gly
        35                  40                  45

Ser Ile Val Lys Lys Lys Trp Ala Ile Asn Ser Ala Phe Met Ala Leu
    50                  55                  60

Tyr Ala Phe Ala Ala Val Trp Ile Cys Trp Val Val Trp Ala Tyr Asn
65                  70                  75                  80

```
Met Ser Phe Gly Asp Arg Leu Leu Pro Phe Trp Lys Ala Arg Pro
             85                  90                  95

Ala Leu Gly Gln Ser Phe Leu Val Ala Gln Ser Glu Leu Thr Ala Thr
            100                 105                 110

Ala Ile Arg Tyr His Asn Gly Ser Ala Glu Ala Pro Met Leu Lys Pro
            115                 120                 125

Leu Tyr Pro Val Ala Thr Met Val Tyr Phe Gln Cys Met Phe Ala Ser
            130                 135                 140

Ile Thr Ile Ile Ile Leu Ala Gly Ser Leu Leu Gly Arg Met Asn Ile
145                 150                 155                 160

Lys Ala Trp Met Ala Phe Val Pro Leu Trp Ile Thr Phe Ser Tyr Thr
                165                 170                 175

Val Cys Ala Phe Ser Leu Trp Gly Gly Gly Phe Leu Phe Gln Trp Gly
                180                 185                 190

Val Ile Asp Tyr Ser Gly Gly Tyr Val Ile His Leu Ser Ser Gly Ile
                195                 200                 205

Ala Gly Leu Thr Ala Ala Tyr Trp Val Gly Pro Arg Ser Ala Ser Asp
            210                 215                 220

Arg Glu Arg Phe Pro Pro Asn Asn Ile Leu Leu Val Leu Ala Gly Ala
225                 230                 235                 240

Gly Leu Leu Trp Leu Gly Trp Thr Gly Phe Asn Gly Gly Asp Pro Tyr
                245                 250                 255

Ser Ala Asn Ile Asp Ser Ser Met Ala Val Leu Asn Thr His Ile Cys
                260                 265                 270

Ala Ser Thr Ser Leu Leu Val Trp Thr Ile Leu Asp Val Phe Phe Phe
            275                 280                 285

Gly Lys Pro Ser Val Ile Gly Ala Val Gln Gly Met Ile Thr Gly Leu
290                 295                 300

Val Cys Ile Thr Pro Gly Ala Gly Leu Val Gln Gly Trp Ala Ala Ile
305                 310                 315                 320

Val Met Gly Ile Leu Ser Gly Ser Ile Pro Trp Tyr Thr Met Met Val
                325                 330                 335

Leu His Lys Lys Trp Ser Phe Met Gln Arg Ile Asp Thr Leu Gly
                340                 345                 350

Val Phe His Thr His Ala Val Ala Gly Phe Leu Gly Gly Ala Thr Thr
            355                 360                 365

Gly Leu Phe Ala Glu Pro Ile Leu Cys Ser Leu Phe Leu Ser Ile Pro
370                 375                 380

Asp Ser Lys Gly Ala Phe Tyr Gly Gly Pro Gly Gly Ser Gln Phe Gly
385                 390                 395                 400

Lys Gln Ile Ala Gly Ala Leu Phe Val Thr Ala Trp Asn Ile Val Ile
                405                 410                 415

Thr Ser Ile Ile Cys Val Ile Ser Leu Ile Leu Pro Leu Arg Ile
                420                 425                 430

Ala Asp Gln Glu Leu Leu Ile Gly Asp Asp Ala Val His Gly Glu Glu
            435                 440                 445

Ala Tyr Ala Ile Trp Ala Glu Gly Glu Leu Asn Asp Met Thr His His
            450                 455                 460

Asn Glu Ser Thr His Ser Gly Val Ser Val Gly Val Thr Gln Asn Val
465                 470                 475                 480

<210> SEQ ID NO 57
<211> LENGTH: 981
<212> TYPE: DNA
<213> ORGANISM: Oryza sativa
```

<400> SEQUENCE: 57

```
atggcgtcgg cggcggtgcc ggagtggctg aacaagggcg acaatgcctg gcagatgctc      60
tccgccacgc tcgtcgccct tcagggcttc ccgggcctcg ccctcttcta cgtcggtgcc     120
gtcccccgca agtgggcgct cacctccgca ttcatggcgc tctacgccat ggccgccacc     180
atgccgtgct gggcgctctg gcgcacaac atggccttcg gccgccgcct cctccccttc      240
gtcggccgcc ccgccccggc gctcgcccag gactacatgc tcagccaggc gctgctcccc     300
tccaccctcc acctccgctc aacggcgag gttgagacgg ccgcggtggc gccgctgtac      360
ccgtcggcga gcatggtgtt cttccagtgg gccttcgccg gcgtcaccgt ggggctggtc     420
gccggcgccg tgctcgggcg catgagcgtc aaggcgtgga tggcgttcgt gccgctgtgg     480
acgacgctgt cctacacggt gggagcgtac agcatctggg gcggaggctt cctcttccac     540
tggggcgtca tggactactc cggcggctac gtcgtgctcc tcgccgccgg cgtctccggc     600
tacacggccc gtactgggt gggacccagg aggaaggagg aggacgagga ggaaatggca      660
acggcgagtg gtggcaacct ggtggtgatg gtggccggcg cgggcatcct gtggatgggg     720
tggaccggct caacggcgg cgaccccttc tccgccaaca ccgactcgtc ggtggcggtg      780
ctcaacacgc acatctgcgc caccaccagc atcgtcgctt gggtttgctg cgacgtcgcc     840
gtccgcggga ggccgtcggt ggtgggcgcg gtgcagggca tgatcaccgg cctggtgtgc     900
atcactccaa ggtcaaacat caagtacagc tttcttctag tagtaatttc tgatgagatg     960
cctgttcctg atctgagcta g                                                981
```

<210> SEQ ID NO 58
<211> LENGTH: 326
<212> TYPE: PRT
<213> ORGANISM: Oryza sativa

<400> SEQUENCE: 58

```
Met Ala Ser Ala Ala Val Pro Glu Trp Leu Asn Lys Gly Asp Asn Ala
  1               5                  10                  15

Trp Gln Met Leu Ser Ala Thr Leu Val Ala Leu Gln Gly Phe Pro Gly
             20                  25                  30

Leu Ala Leu Phe Tyr Val Gly Ala Val Pro Arg Lys Trp Ala Leu Thr
         35                  40                  45

Ser Ala Phe Met Ala Leu Tyr Ala Met Ala Thr Met Pro Cys Trp
     50                  55                  60

Ala Leu Trp Ala His Asn Met Ala Phe Gly Arg Arg Leu Leu Pro Phe
 65                  70                  75                  80

Val Gly Arg Pro Ala Pro Ala Leu Ala Gln Asp Tyr Met Leu Ser Gln
                 85                  90                  95

Ala Leu Leu Pro Ser Thr Leu His Leu Arg Ser Asn Gly Glu Val Glu
            100                 105                 110

Thr Ala Ala Val Ala Pro Leu Tyr Pro Ser Ala Ser Met Val Phe Phe
        115                 120                 125

Gln Trp Ala Phe Ala Gly Val Thr Val Gly Leu Val Ala Gly Ala Val
    130                 135                 140

Leu Gly Arg Met Ser Val Lys Ala Trp Met Ala Phe Val Pro Leu Trp
145                 150                 155                 160

Thr Thr Leu Ser Tyr Thr Val Gly Ala Tyr Ser Ile Trp Gly Gly
                165                 170                 175

Phe Leu Phe His Trp Gly Val Met Asp Tyr Ser Gly Gly Tyr Val Val
            180                 185                 190
```

```
Leu Leu Ala Ala Gly Val Ser Gly Tyr Thr Ala Ala Tyr Trp Val Gly
            195                 200                 205

Pro Arg Arg Lys Glu Glu Asp Glu Glu Glu Met Ala Thr Ala Ser Gly
210                 215                 220

Gly Asn Leu Val Val Met Val Ala Gly Ala Gly Ile Leu Trp Met Gly
225                 230                 235                 240

Trp Thr Gly Phe Asn Gly Gly Asp Pro Phe Ser Ala Asn Thr Asp Ser
                245                 250                 255

Ser Val Ala Val Leu Asn Thr His Ile Cys Ala Thr Thr Ser Ile Val
            260                 265                 270

Ala Trp Val Cys Cys Asp Val Ala Val Arg Gly Arg Pro Ser Val Val
        275                 280                 285

Gly Ala Val Gln Gly Met Ile Thr Gly Leu Val Cys Ile Thr Pro Arg
    290                 295                 300

Ser Asn Ile Lys Tyr Ser Phe Leu Leu Val Val Ile Ser Asp Glu Met
305                 310                 315                 320

Pro Val Pro Asp Leu Ser
                325

<210> SEQ ID NO 59
<211> LENGTH: 1377
<212> TYPE: DNA
<213> ORGANISM: Oryza sativa

<400> SEQUENCE: 59
atggcgtcgg tggcggtgcc ggagtggctg aacaagggcg acaacgcctg gcagatgctc      60
tccgccacgc tcgtcgccct gcagggcttc cccggtctcg ccctcttcta cgccggcgcc     120
gtcacccgca agtgcgcgct cacctccgca ttcatggcgc tctacgccat ggccgccacc     180
atgccgtgct gggcgctctg gcgcacaac atggccttcg ccaccgcct cctgcccttc      240 gtcggccgcc ccgccccggc gctcgcccag cactacatgc tcacccaggc gctgctcccc     300
ttcaccctcc acctccactc caacggcgag gtggagacgg ccgcggtggc gccgctgtac     360
ccgtcggcga gcatggtgtt cttccagtgg gcctccgccg cgtcaccgt ggggctggtc      420 gccggcgccg tgctcgggcg catgagcgtc aaggcgtgga tggcgttcgt gccgctgtgg     480
acgacgctgt cctatacggt gggagcgtac agcatttggg gcggggcctt cctcttccac     540
tggggcgtca tggactactc cggcggctac gtcgttcacc tcgccgccgg cgtctccggc     600
tacacggccg cgtactgggt gggaccaagg aggaaggagg aggaggaaat gacaatggcg     660
ggtggtggca acctggtggc gatggtggcc ggcgcgggca tcctgtggat ggggtggacc     720
ggcttcaacg gcggcgaccc cttctccgcc aacaccgact cgtcggtggc ggtgctcaac     780
acgcacatct gcaccaccac cagcatcctc gcttgggttt gctgcgacat cgccgtccgc     840
gggaggccgt cggtggtggg gcggtgcag ggcatgatca ccggcctggt gtgcataact       900
ccggcggcag ggctggtgca ggggtgggca gctctgctaa tgggcgtcgc gtcggggaca     960
ctgccatgct acaccatgaa cgccgccatg tcgttcaagg tagacgacac gctgggcatc    1020
ctgcacaccc acgcggtgtc cggtgttctg ggcggcgtcc tcaccggcgt tttcgcgcac    1080
cctactctct gtgacatgtt ccttccggtg accggctcaa gggcctcgt ctacggcgtc     1140 cgcgccggcg gggtgcaggt gttgaagcag gtcgccgccg cattgttcgt tgccgcatgg    1200
aacgtggccg ccacgtccat catcttggtc gtcgtcaggg cgttcgtgcc gctgaggatg    1260
acggaagatg agctgctcgc cggagacatt gccgtacatg gggaacaagc ttattatttt    1320
```
tcgagtggca ccaattgtag tttaagccat gagaccattg aggtcggaaa ttcataa    1377

<210> SEQ ID NO 60
<211> LENGTH: 458
<212> TYPE: PRT
<213> ORGANISM: Oryza sativa

<400> SEQUENCE: 60

Met Ala Ser Val Ala Val Pro Glu Trp Leu Asn Lys Gly Asp Asn Ala
1               5                   10                  15

Trp Gln Met Leu Ser Ala Thr Leu Val Ala Leu Gln Gly Phe Pro Gly
                20                  25                  30

Leu Ala Leu Phe Tyr Ala Gly Ala Val Thr Arg Lys Cys Ala Leu Thr
            35                  40                  45

Ser Ala Phe Met Ala Leu Tyr Ala Met Ala Ala Thr Met Pro Cys Trp
        50                  55                  60

Ala Leu Trp Ala His Asn Met Ala Phe Gly His Arg Leu Leu Pro Phe
65                  70                  75                  80

Val Gly Arg Pro Ala Pro Ala Leu Ala Gln His Tyr Met Leu Thr Gln
                85                  90                  95

Ala Leu Leu Pro Phe Thr Leu His Leu His Ser Asn Gly Glu Val Glu
            100                 105                 110

Thr Ala Ala Val Ala Pro Leu Tyr Pro Ser Ala Ser Met Val Phe Phe
        115                 120                 125

Gln Trp Ala Ser Ala Gly Val Thr Val Gly Leu Val Ala Gly Ala Val
    130                 135                 140

Leu Gly Arg Met Ser Val Lys Ala Trp Met Ala Phe Val Pro Leu Trp
145                 150                 155                 160

Thr Thr Leu Ser Tyr Thr Val Gly Ala Tyr Ser Ile Trp Gly Gly Gly
                165                 170                 175

Phe Leu Phe His Trp Gly Val Met Asp Tyr Ser Gly Gly Tyr Val Val
            180                 185                 190

His Leu Ala Ala Gly Val Ser Gly Tyr Thr Ala Ala Tyr Trp Val Gly
        195                 200                 205

Pro Arg Arg Lys Glu Glu Glu Met Thr Met Ala Gly Gly Gly Asn
    210                 215                 220

Leu Val Ala Met Val Ala Gly Ala Gly Ile Leu Trp Met Gly Trp Thr
225                 230                 235                 240

Gly Phe Asn Gly Gly Asp Pro Phe Ser Ala Asn Thr Asp Ser Ser Val
                245                 250                 255

Ala Val Leu Asn Thr His Ile Cys Thr Thr Ser Ile Leu Ala Trp
            260                 265                 270

Val Cys Cys Asp Ile Ala Val Arg Gly Arg Pro Ser Val Val Gly Ala
        275                 280                 285

Val Gln Gly Met Ile Thr Gly Leu Val Cys Ile Thr Pro Ala Ala Gly
    290                 295                 300

Leu Val Gln Gly Trp Ala Ala Leu Leu Met Gly Val Ala Ser Gly Thr
305                 310                 315                 320

Leu Pro Cys Tyr Thr Met Asn Ala Ala Met Ser Phe Lys Val Asp Asp
                325                 330                 335

Thr Leu Gly Ile Leu His Thr His Ala Val Ser Gly Val Leu Gly Gly
            340                 345                 350

Val Leu Thr Gly Val Phe Ala His Pro Thr Leu Cys Asp Met Phe Leu
        355                 360                 365

Pro Val Thr Gly Ser Arg Gly Leu Val Tyr Gly Val Arg Ala Gly Gly

|     |     |     |     |     |     |     |     |     |     |
| --- | --- | --- | --- | --- | --- | --- | --- | --- | --- |
|     |     | 370 |     |     | 375 |     |     | 380 |     |
| Val | Gln | Val | Leu | Lys | Gln | Val | Ala | Ala | Ala |
| 385 |     |     |     |     | 390 |     |     |     | 395 |

Leu Phe Val Ala Ala Trp
                    400

Asn Val Ala Ala Thr Ser Ile Ile Leu Val Val Val Arg Ala Phe Val
            405                 410                 415

Pro Leu Arg Met Thr Glu Asp Glu Leu Leu Ala Gly Asp Ile Ala Val
            420                 425                 430

His Gly Glu Gln Ala Tyr Tyr Phe Ser Ser Gly Thr Asn Cys Ser Leu
            435                 440                 445

Ser His Glu Thr Ile Glu Val Gly Asn Ser
    450                 455

<210> SEQ ID NO 61
<211> LENGTH: 1750
<212> TYPE: DNA
<213> ORGANISM: Glycine max

<400> SEQUENCE: 61

```
atttcatata tgtatatata gcatcagaga gagaacaatt ctttgaaggg tgaaaaacct      60
tgatcaagaa ttgaagcatt aatcttcaac catggccaca cccttggcct accaagagca     120
ccttccggcg gcacccggtt ggctgaacaa aggtgacaac gcatggcagt aacagcagc      180
caccctcgtt ggtcttcaaa gcatgccggg tctcgtgatc ctctacgcaa gcatagtgaa     240
gaagaaatgg gcagtgaatt cagctttcat ggctctctat gcctttgcag cagttctaat     300
atgttgggtg cttgtgtgtt accgcatggc ctttggagaa gaacttttac ccttctgggg     360
taagggtgct ccagcactag gccagaagtt cctcacaaaa cgagccgtag tcaatgaaac     420
catccaccac tttgataatg gcactgttga atcacctcct gaggaaccct tttaccctat     480
ggcctcgctt gtgtatttcc aattcacttt tgctgctatt actcttattt tgttggctgg     540
ctctgtcctt ggccgaatga acatcaaggc ttggatggct tttgtgcctc tttggttgat     600
cttttcctac acagtcgggg cttttagtct ttggggtggt ggctttctct accaatgggg     660
cgttattgat tattctggcg gctatgtcat acacctttct tctggaatcg ctggcttcac     720
tgctgcttac tgggttggac aaggttgaa gagtgatagg gagaggttcc caccaaacaa      780
tgtgcttctc atgcttgctg gtgctgggtt gttgtggatg ggttggtcag ggttcaacgg     840
tggagcacca tatgctgcaa acattgcatc ttcaattgcg gtgttgaaca caaacatttg     900
tgcagccact agcttccttg tgtggacaac tttggatgtc attttttttg ggaaaccttc     960
ggtgattgga gctgtgcagg gcatgatgac tggacttgta tgcatcaccc caggggcagg    1020
gcttgtgcat tcatgggctg ttatagtgat gggaatatta tttgggagca ttccatgggt    1080
gactatgatg attttgcata aaaagtcaac tttgctacag aaggtagatg acacccttgg    1140
tgtgtttcac acacatgctg tggctggcct tttgggtggt ctcctcacag gtctattagc    1200
agaaccagcc ctttgtagac ttctattgcc agtaacaaat tcaaggggtg cattctatgg    1260
tggaggtggt ggtgtgcagt tcttcaagca attggtggcg gccatgtttg ttattggatg    1320
gaacttggtg tccaccacca ttattctcct tgtcataaaa ttgttcatac ccttgaggat    1380
gccggacgag cagctggaaa tcggtgacga cgccgtccac ggtgaggaag cttatgccct    1440
ttgggggtgat ggagaaaaat atgacccaac taggcatggt tccttgcaaa gtggcaacac    1500
tactgtctca ccttatgtta atggtgcaag aggggtgact ataaacttat gagtcaagaa    1560
attaggctgt gccttgctca cacatgcatg tgtataaatt tatatgatta acaaatgtga    1620
tgaatccgtg agtggtataa gtagatattt gattttgtca tgaaagaaaa tttccaaatt    1680
```

```
ttgagatgtg atgttcctct ggtcatcttg cattcgaaga ctctggtcat atatttctgg   1740
cacagaatgt                                                          1750
```

<210> SEQ ID NO 62
<211> LENGTH: 486
<212> TYPE: PRT
<213> ORGANISM: Glycine max

<400> SEQUENCE: 62

Met Ala Thr Pro Leu Ala Tyr Gln Glu His Leu Pro Ala Ala Pro Gly
1               5                   10                  15

Trp Leu Asn Lys Gly Asp Asn Ala Trp Gln Leu Thr Ala Ala Thr Leu
            20                  25                  30

Val Gly Leu Gln Ser Met Pro Gly Leu Val Ile Leu Tyr Ala Ser Ile
        35                  40                  45

Val Lys Lys Lys Trp Ala Val Asn Ser Ala Phe Met Ala Leu Tyr Ala
    50                  55                  60

Phe Ala Ala Val Leu Ile Cys Trp Val Leu Val Cys Tyr Arg Met Ala
65                  70                  75                  80

Phe Gly Glu Glu Leu Leu Pro Phe Trp Gly Lys Gly Ala Pro Ala Leu
                85                  90                  95

Gly Gln Lys Phe Leu Thr Lys Arg Ala Val Val Asn Glu Thr Ile His
            100                 105                 110

His Phe Asp Asn Gly Thr Val Glu Ser Pro Pro Glu Glu Pro Phe Tyr
        115                 120                 125

Pro Met Ala Ser Leu Val Tyr Phe Gln Phe Thr Phe Ala Ala Ile Thr
    130                 135                 140

Leu Ile Leu Leu Ala Gly Ser Val Leu Gly Arg Met Asn Ile Lys Ala
145                 150                 155                 160

Trp Met Ala Phe Val Pro Leu Trp Leu Ile Phe Ser Tyr Thr Val Gly
                165                 170                 175

Ala Phe Ser Leu Trp Gly Gly Gly Phe Leu Tyr Gln Trp Gly Val Ile
            180                 185                 190

Asp Tyr Ser Gly Gly Tyr Val Ile His Leu Ser Ser Gly Ile Ala Gly
        195                 200                 205

Phe Thr Ala Ala Tyr Trp Val Gly Pro Arg Leu Lys Ser Asp Arg Glu
    210                 215                 220

Arg Phe Pro Pro Asn Asn Val Leu Leu Met Leu Ala Gly Ala Gly Leu
225                 230                 235                 240

Leu Trp Met Gly Trp Ser Gly Phe Asn Gly Gly Ala Pro Tyr Ala Ala
                245                 250                 255

Asn Ile Ala Ser Ser Ile Ala Val Leu Asn Thr Asn Ile Cys Ala Ala
            260                 265                 270

Thr Ser Phe Leu Val Trp Thr Thr Leu Asp Val Ile Phe Phe Gly Lys
        275                 280                 285

Pro Ser Val Ile Gly Ala Val Gln Gly Met Met Thr Gly Leu Val Cys
    290                 295                 300

Ile Thr Pro Gly Ala Gly Leu Val His Ser Trp Ala Val Ile Val Met
305                 310                 315                 320

Gly Ile Leu Phe Gly Ser Ile Pro Trp Val Thr Met Met Ile Leu His
                325                 330                 335

Lys Lys Ser Thr Leu Leu Gln Lys Val Asp Asp Thr Leu Gly Val Phe
            340                 345                 350

His Thr His Ala Val Ala Gly Leu Leu Gly Gly Leu Leu Thr Gly Leu 355                 360                 365
Leu Ala Glu Pro Ala Leu Cys Arg Leu Leu Pro Val Thr Asn Ser
            370                 375                 380

Arg Gly Ala Phe Tyr Gly Gly Gly Gly Val Gln Phe Phe Lys Gln
385                 390                 395                 400

Leu Val Ala Ala Met Phe Val Ile Gly Trp Asn Leu Val Ser Thr Thr
                405                 410                 415

Ile Ile Leu Leu Val Ile Lys Leu Phe Ile Pro Leu Arg Met Pro Asp
                420                 425                 430

Glu Gln Leu Glu Ile Gly Asp Asp Ala Val His Gly Glu Glu Ala Tyr
            435                 440                 445

Ala Leu Trp Gly Asp Gly Glu Lys Tyr Asp Pro Thr Arg His Gly Ser
            450                 455                 460

Leu Gln Ser Gly Asn Thr Thr Val Ser Pro Tyr Val Asn Gly Ala Arg
465                 470                 475                 480

Gly Val Thr Ile Asn Leu
                485

<210> SEQ ID NO 63
<211> LENGTH: 2191
<212> TYPE: DNA
<213> ORGANISM: Glycine max

<400> SEQUENCE: 63
cgtaatacac taaccaaccc accatgtcgc tgcctgcttg tcccgccgaa caactggccc      60
aacttctcgg cccaaacacc acagacgcct ccgccgccgc ctcccttatc tgcggccatt     120
tcgccgccgt ggacagcaag ttcgtcgaca cggccttcgc cgtcgacaac acctacctcc     180
tcttttccgc ctacctcgtt ttttctatgc agctcggctt cgccatgctc tgcgccggct     240
ccgtccgcgc caagaacacc atgaacatca tgctcaccaa cgtcctggac gctgccgccg     300
gcggcctctt ctactacctc ttcggcttcg ccttcgcttt cggctccccc tccaacggct     360
tcatcggtaa acatttcttc ggcctcaagg acatccctttc atcctcctac gactacagct     420
acttcctcta ccaatgggcc ttcgccatcg ccgccgccgg catcaccagc ggaagcatcg     480
ccgaacgcac acagttcgtg gcctatctca tctactcctc cttcctcacc ggcttcgtct     540
atccggtggt ctcccactgg ttctggtccc cagacggctg ggcctctgcc tttaagatca     600
ccgaccggct attttccacc ggcgtaatag acttcgccgg ttccggcgta gtccacatgg     660
tcggcggaat agccggccta tggggagcgc tgatcgaagg cccaagaatg ggacgtttcg     720
atcatgcagg acgagctgtg gccttgcgag gccacagcgc gtccttagta gtcctgggaa     780
ccttcttgct ttggttcggt tggtacggat taaccccgg ttcatttaac aaaatcctac      840
ttacttacgg taactcagga aattactacg gtcaatggag cgcggttggc agaaccgcgg     900
tcaccactac cctagcgggg tcaacagctg ccttgaccac gctattcggt aaacgggtga     960
tatccggtca ctggaacgtg accgatgtct gcaacgggct gttaggcggt tcgcggcga    1020 taacagccgg ttgctccgtg gttgagccat gggcagccat cgtatgcggt tttgttgctt    1080
ctatagtatt aatagcttgc aacaaattag cagagaaggt taagttcgac gatcctctgg    1140
aggcggcgca gttgcacggt gggtgtggca cgtgggggt gatattcacg gcgttgttcg    1200
caaaaaagga gtatgtgaag gaggtttacg ggttgggag ggcgcacggg ttgctcatgg     1260
ggggtggtgg gaagttgctg gcggcgcacg tgattcagat tctggtgatt gctgggtggg    1320
ttagtgcgac catgggaccc ttgttttggg ggttgaataa actgaagctg ttgaggattt    1380

-continued

```
cttcagagga tgagcttgcg gggatggaca tgactcgcca tggaggcttt gcttatgctt    1440
atgaggatga tgagacgcac aagcatggga tgcagttgag gagggttggg cccaacgcgt    1500
cttccacacc caccactgat gaatgatctt ttttttccat atgcatgtct cattagtcaa    1560
acattaaatt tggatacata ttccttgtaa ggattcaaac cttggttact tgttacttct    1620
gttagatcca actccggttg atactcatga cttttactt ctttttttt tatttgtctt    1680 gggtcttctt ttttcgtaga tttttctttt tatgatgatg ggcaattagg gattttgatt    1740
tgtaattgtc attggtcgtg cattggtgga tgctggaagt taaagattct ggtggaagat    1800
gcgtacgttt ctgtgggggg tggttgttga ctaaggcatg ttggtcctgg aaatgacaga    1860
tggctgtgga aaatggaaat ttgtgggatt tatttttgta gttttcacca aaaagaagg    1920 aagaagattg gtatatagta gaaatactac tgtttggccg tgaggcatat agtttttttt    1980
tcttttcctt aatttgagac ttttatgtta aacttttca ttatgtctaa tgtaaatata    2040
tggaagtagt ttttatattt tactgcctga atgtttgttt tttgtgttat atgttttgt     2100 ttatatggaa ttgaaatcga ttgtaatatg ttacgtggaa gtaatgtaag ttaaaagatg    2160
atgtaggtag tgttatttag tgttttttttt t                                  2191
```

<210> SEQ ID NO 64
<211> LENGTH: 500
<212> TYPE: PRT
<213> ORGANISM: Glycine max

<400> SEQUENCE: 64

```
Met Ser Leu Pro Ala Cys Pro Ala Glu Gln Leu Ala Gln Leu Leu Gly
 1               5                  10                  15

Pro Asn Thr Thr Asp Ala Ser Ala Ala Ala Ser Leu Ile Cys Gly His
             20                  25                  30

Phe Ala Ala Val Asp Ser Lys Phe Val Asp Thr Ala Phe Ala Val Asp
         35                  40                  45

Asn Thr Tyr Leu Leu Phe Ser Ala Tyr Leu Val Phe Ser Met Gln Leu
     50                  55                  60

Gly Phe Ala Met Leu Cys Ala Gly Ser Val Arg Ala Lys Asn Thr Met
 65                  70                  75                  80

Asn Ile Met Leu Thr Asn Val Leu Asp Ala Ala Gly Gly Leu Phe
                 85                  90                  95

Tyr Tyr Leu Phe Gly Phe Ala Phe Ala Phe Gly Ser Pro Ser Asn Gly
            100                 105                 110

Phe Ile Gly Lys His Phe Phe Gly Leu Lys Asp Ile Pro Ser Ser Ser
        115                 120                 125

Tyr Asp Tyr Ser Tyr Phe Leu Tyr Gln Trp Ala Phe Ala Ile Ala Ala
    130                 135                 140

Ala Gly Ile Thr Ser Gly Ser Ile Ala Glu Arg Thr Gln Phe Val Ala
145                 150                 155                 160

Tyr Leu Ile Tyr Ser Ser Phe Leu Thr Gly Phe Val Tyr Pro Val Val
                165                 170                 175

Ser His Trp Phe Trp Ser Pro Asp Gly Trp Ala Ser Ala Phe Lys Ile
            180                 185                 190

Thr Asp Arg Leu Phe Ser Thr Gly Val Ile Asp Phe Ala Gly Ser Gly
        195                 200                 205

Val Val His Met Val Gly Gly Ile Ala Gly Leu Trp Gly Ala Leu Ile
    210                 215                 220

Glu Gly Pro Arg Met Gly Arg Phe Asp His Ala Gly Arg Ala Val Ala
225                 230                 235                 240
```

Leu Arg Gly His Ser Ala Ser Leu Val Val Leu Gly Thr Phe Leu Leu
            245                 250                 255

Trp Phe Gly Trp Tyr Gly Phe Asn Pro Gly Ser Phe Asn Lys Ile Leu
            260                 265                 270

Leu Thr Tyr Gly Asn Ser Gly Asn Tyr Tyr Gly Gln Trp Ser Ala Val
            275                 280                 285

Gly Arg Thr Ala Val Thr Thr Thr Leu Ala Gly Ser Thr Ala Ala Leu
            290                 295                 300

Thr Thr Leu Phe Gly Lys Arg Val Ile Ser Gly His Trp Asn Val Thr
305                 310                 315                 320

Asp Val Cys Asn Gly Leu Leu Gly Gly Phe Ala Ile Thr Ala Gly
            325                 330                 335

Cys Ser Val Val Glu Pro Trp Ala Ala Ile Val Cys Gly Phe Val Ala
            340                 345                 350

Ser Ile Val Leu Ile Ala Cys Asn Lys Leu Ala Glu Lys Val Lys Phe
            355                 360                 365

Asp Asp Pro Leu Glu Ala Ala Gln Leu His Gly Gly Cys Gly Thr Trp
            370                 375                 380

Gly Val Ile Phe Thr Ala Leu Phe Ala Lys Lys Glu Tyr Val Lys Glu
385                 390                 395                 400

Val Tyr Gly Leu Gly Arg Ala His Gly Leu Leu Met Gly Gly Gly
            405                 410                 415

Lys Leu Leu Ala Ala His Val Ile Gln Ile Leu Val Ile Ala Gly Trp
            420                 425                 430

Val Ser Ala Thr Met Gly Pro Leu Phe Trp Gly Leu Asn Lys Leu Lys
            435                 440                 445

Leu Leu Arg Ile Ser Ser Glu Asp Glu Leu Ala Gly Met Asp Met Thr
            450                 455                 460

Arg His Gly Gly Phe Ala Tyr Ala Tyr Glu Asp Asp Glu Thr His Lys
465                 470                 475                 480

His Gly Met Gln Leu Arg Arg Val Gly Pro Asn Ala Ser Ser Thr Pro
            485                 490                 495

Thr Thr Asp Glu
            500

<210> SEQ ID NO 65
<211> LENGTH: 800
<212> TYPE: DNA
<213> ORGANISM: Glycine max

<400> SEQUENCE: 65
gcttctccca cctcaaacgc cgtcgtttcg accaccttct tcggtcgcgg cacaaccaat      60
aaccatgtcg ctgccagatt gtcccgccgt ccaacttgcc caactcctgg gcccaaatac     120
cacaaacgct gccgccgccg cctccttcat ctgcgaccgg ttcaccgccg tggacaacaa     180
gttcgtcgac acggccttcg cggtcgacaa cacttacctc ctcttctccg cctacctcgt     240
cttctcgatg cagctcggct tcgccatgct ctgcgccggc tccgtccgcg ccaagaacac     300
catgaacatc atgctcacca acgtcctcga cgccgccgcc ggcggcctct tctactacct     360
cttcggcttc gccttcgcct tcggctcccc tccaacggc ttcattggca aacacttctt     420
cggcctcaag gaactcccct cccaaagctt cgactacagc aactttctct atcaatgggc     480
cttcgccatc gccgccgccg gcatcaccag cggctccatc gccgaacgca cacagttcgt     540
ggcctatctc atctactcct ccttcctcac cggcttcgtc taccccgtcg tctcccactg     600

| | | | |
|---|---|---|---|
| gttctggtcc gcagacggct gggcttctgc catttccccc ggagaccggc tattttccac | | | 660 |
| cggcgtgata gacttcgccg gctccggcgt agtccacatg gttggtggag tagccggctt | | | 720 |
| ctggggcgca ctgatagaag gcccgagaat cggacgcttc gaccacgcgg gacgcgccgt | | | 780 |
| tgccctcaga ggccacagcg | | | 800 |

<210> SEQ ID NO 66
<211> LENGTH: 245
<212> TYPE: PRT
<213> ORGANISM: Glycine max

<400> SEQUENCE: 66

Met Ser Leu Pro Asp Cys Pro Ala Val Gln Leu Ala Gln Leu Leu Gly
 1               5                  10                  15

Pro Asn Thr Thr Asn Ala Ala Ala Ala Ser Phe Ile Cys Asp Arg
             20                  25                  30

Phe Thr Ala Val Asp Asn Lys Phe Val Asp Thr Ala Phe Ala Val Asp
         35                  40                  45

Asn Thr Tyr Leu Leu Phe Ser Ala Tyr Leu Val Phe Ser Met Gln Leu
     50                  55                  60

Gly Phe Ala Met Leu Cys Ala Gly Ser Val Arg Ala Lys Asn Thr Met
 65                  70                  75                  80

Asn Ile Met Leu Thr Asn Val Leu Asp Ala Ala Gly Gly Leu Phe
                 85                  90                  95

Tyr Tyr Leu Phe Gly Phe Ala Phe Ala Phe Gly Ser Pro Ser Asn Gly
            100                 105                 110

Phe Ile Gly Lys His Phe Phe Gly Leu Lys Glu Leu Pro Ser Gln Ser
        115                 120                 125

Phe Asp Tyr Ser Asn Phe Leu Tyr Gln Trp Ala Phe Ala Ile Ala Ala
    130                 135                 140

Ala Gly Ile Thr Ser Gly Ser Ile Ala Glu Arg Thr Gln Phe Val Ala
145                 150                 155                 160

Tyr Leu Ile Tyr Ser Ser Phe Leu Thr Gly Phe Val Tyr Pro Val Val
                165                 170                 175

Ser His Trp Phe Trp Ser Ala Asp Gly Trp Ala Ser Ala Ile Ser Pro
            180                 185                 190

Gly Asp Arg Leu Phe Ser Thr Gly Val Ile Asp Phe Ala Gly Ser Gly
        195                 200                 205

Val Val His Met Val Gly Gly Val Ala Gly Phe Trp Gly Ala Leu Ile
    210                 215                 220

Glu Gly Pro Arg Ile Gly Arg Phe Asp His Ala Gly Arg Ala Val Ala
225                 230                 235                 240

Leu Arg Gly His Ser
                245

<210> SEQ ID NO 67
<211> LENGTH: 644
<212> TYPE: DNA
<213> ORGANISM: Glycine max

<400> SEQUENCE: 67

| | | | |
|---|---|---|---|
| cggtgcttaa caccaacatt tgcgccgcca ccagcctcct cgtatggacg tggttggacg | | | 60 |
| ttattttctt caagaaaccc tcagttattg agccgttca gggcatgata actggccttg | | | 120 |
| tttgcatcac tcccggagct ggtctggttc aaggatgggc tgccatagtg atggacttc | | | 180 |
| tttcaggcag tgtcccatgg ttcagcatga tggtattagg gaaaaagctg aaattgtttc | | | 240 |

-continued

```
aaatggttga tgacacccctt gctgtgttcc acactcatgc tgtggctggc cttcttggag      300
gcatactcac tggcctatt gccgaacctc gtctgtgtgc actctttcta cctgtcacca       360
actccaaaag aggagtctat ggaggccctg gtggagtcca atccttaaa caaatcgtgg        420 gagctttgtt catcattggg tggaaccttg tggtcacttc aattatttgt gtggttatta      480
gtttcatagt tccacttaga atgacagagg aagagcttct cattggagat gatgcggttc      540
atggggaaga ggcttatgct ctgtggggtg atggagagaa acttagcatc tacaaagatg      600
ataccactca ccatggagtt gtgtctagtg gtgccactca agtg                       644
```

<210> SEQ ID NO 68
<211> LENGTH: 204
<212> TYPE: PRT
<213> ORGANISM: Glycine max

<400> SEQUENCE: 68

```
Val Leu Asn Thr Asn Ile Cys Ala Ala Thr Ser Leu Leu Val Trp Thr
 1               5                  10                  15

Trp Leu Asp Val Ile Phe Phe Lys Lys Pro Ser Val Ile Gly Ala Val
                20                  25                  30

Gln Gly Met Ile Thr Gly Leu Val Cys Ile Thr Pro Gly Ala Gly Leu
            35                  40                  45

Val Gln Gly Trp Ala Ala Ile Val Met Gly Leu Leu Ser Gly Ser Val
        50                  55                  60

Pro Trp Phe Ser Met Met Val Leu Gly Lys Lys Leu Lys Leu Phe Gln
 65                  70                  75                  80

Met Val Asp Asp Thr Leu Ala Val Phe His Thr His Ala Val Ala Gly
                85                  90                  95

Leu Leu Gly Gly Ile Leu Thr Gly Leu Phe Ala Glu Pro Arg Leu Cys
            100                 105                 110

Ala Leu Phe Leu Pro Val Thr Asn Ser Lys Arg Gly Val Tyr Gly Gly
        115                 120                 125

Pro Gly Gly Val Gln Ile Leu Lys Gln Ile Val Gly Ala Leu Phe Ile
    130                 135                 140

Ile Gly Trp Asn Leu Val Val Thr Ser Ile Ile Cys Val Val Ile Ser
145                 150                 155                 160

Phe Ile Val Pro Leu Arg Met Thr Glu Glu Glu Leu Leu Ile Gly Asp
                165                 170                 175

Asp Ala Val His Gly Glu Glu Ala Tyr Ala Leu Trp Gly Asp Gly Glu
            180                 185                 190

Lys Leu Ser Ile Tyr Lys Asp Asp Thr Thr His His
        195                 200
```

<210> SEQ ID NO 69
<211> LENGTH: 749
<212> TYPE: DNA
<213> ORGANISM: Glycine max

<400> SEQUENCE: 69

```
gccacaaaca attcatcagc tcatacacgt aatttctttt cctcttttcc tcttatccaa       60
ttctaatcac gatcagacat taaatgtaaa cacttctcta tcaaaaattt gaacttagtt      120
cgcctcacac ttttgttttg tcaccttgtg agagactaat tccctctaat aaacgcaacg      180
ttgttcatca gtggcacata catatacagc atcacaattc tttgaagggt gaaaaagctt      240
gatcaagaat tgaagcatat tgatcttcag ccatggctac acccttggcc taccaagagc      300
accttccggc ggcacccgaa tggctgaaca aggtgacaa cgcatggcag ctaacagcag       360
```

-continued

```
ccaccctcgt cggtcttcaa agcatgccgg gtctcgtgat cctctacgcc agcatagtga    420
agaaaaaatg ggcagtgaac tcagctttca tggctctcta cgcctttgcg gcggttctaa    480
tatgttgggt gcttgtgtgt taccgcatgg cctttggaga aaaactttta cccttctggg    540
ggaagggtgc tcccagactt aggccagaat cgtcacaaa acgagccgga gtcaatgaaa     600
cgctgcacca ctttgatagt ggcactgtag aatcccctcg cgaagagcca ctttacccta    660
atggcgtact tgtgtatgtc cgattgactt ttgctgctat gtaccatata gtgatggctg    720
gctctgtgct gccacgaaga acatcgaag                                      749
```

<210> SEQ ID NO 70
<211> LENGTH: 159
<212> TYPE: PRT
<213> ORGANISM: Glycine max

<400> SEQUENCE: 70

```
Met Ala Thr Pro Leu Ala Tyr Gln Glu His Leu Pro Ala Ala Pro Glu
  1               5                  10                  15

Trp Leu Asn Lys Gly Asp Asn Ala Trp Gln Leu Thr Ala Ala Thr Leu
             20                  25                  30

Val Gly Leu Gln Ser Met Pro Gly Leu Val Ile Leu Tyr Ala Ser Ile
         35                  40                  45

Val Lys Lys Lys Trp Ala Val Asn Ser Ala Phe Met Ala Leu Tyr Ala
     50                  55                  60

Phe Ala Ala Val Leu Ile Cys Trp Val Leu Val Cys Tyr Arg Met Ala
 65                  70                  75                  80

Phe Gly Glu Lys Leu Leu Pro Phe Trp Gly Lys Gly Ala Pro Arg Leu
                 85                  90                  95

Arg Pro Glu Phe Val Thr Lys Arg Ala Gly Val Asn Glu Thr Leu His
            100                 105                 110

His Phe Asp Ser Gly Thr Val Glu Ser Pro Arg Glu Gly Pro Leu Tyr
        115                 120                 125

Pro Asn Gly Val Leu Val Tyr Val Arg Leu Thr Phe Ala Ala Met Tyr
    130                 135                 140

His Ile Val Met Ala Gly Ser Val Leu Pro Arg Arg Thr Ser Lys
145                 150                 155
```

<210> SEQ ID NO 71
<211> LENGTH: 1871
<212> TYPE: DNA
<213> ORGANISM: Glycine max

<400> SEQUENCE: 71

```
ctctaacagc caaagcatgg cttctctctc ttgctccgcc aacgaccttg ccccactctt     60
caacgacacc gccgccgcca actacctctg cgcccaattc gattccattt ctagaaagct    120
cgccgaaaca acctacgccg tcgacaacac ctaccttctg ttttcagcgt atcttgtctt    180
cgccatgcag ctcggcttcg ccatgctctg cgccggctcc gtcagagcca aaaacaccat    240
gaacatcatg ctcaccaacg tcctcgacgc cgccgccggc ggtctctcct actacctatt    300
cggctttgca ttcgccttcg gcggcccctc caacggcttc atcggccgcc acttcttcgg    360
cctacgagat tacccaatgg ctcctctccc ctccggcgac tacagcttct tcctctacca    420
gtgggccttc gccatcgccc cgcaggaat caccagcggc tccatcgccg agagaacaca    480
gttcgtggct tacctatctc actcttcttt cttaaccggt ttcgtttacc ccatcgtttc    540
gcattggttc tggtcctcag acggttgggc cagcgcgact cgtagccacg gaaatgtttt    600
```

```
attcgggtct ggagtcatcg acttcgcggg ctcaggcgtt gttcacatgg ttggcgggat    660
agcgggcctg tgggggcttt aattgaagg cccgagaatc ggccggttcg accgttcggg    720
ccggtcggtt gctttacgtg ccacagcgc gtctttagtt gtgcttggta cgttttttgtt   780 atggttcggc tggtacggct tcaaccctgg ttcgtttgtg acaatagaca aggggtatga    840
aagtggaggg tattatggtc aatggagcgc tatagggagg acagctgtca cgacgacatt    900
ggctgggagc actgcggctc tgacgacgtt gttcagcaag cggttattgg ttggccactg    960
gaacgtgatt gacgtgtgta acggcctgct tggcgggttc gctgccatta catcgggctg   1020
tgccgttgtg gaaccgtggg ccgcgattgt gtgtgggttt gtggcggcgt gggttttgat   1080
tgggcttaat aagcttgccg cgaaggtaga gtacgatgat ccgttggagg cggcgcagct   1140
tcacggcggg tgcggcgcgt ggggtgtttt cttcacggga ttgtttgcga agaaagtgta   1200
cgtggaggag atttacggtg ttggaaggcc gttcggggct ttgatgggtg cggaggggag   1260
gctgctggcg gcgcaggtga ttcagatatt ggtggtgtgc gggtgggtta cggcgaccat   1320
ggcgccgttg ttctatgggc ttcataagat gaaactgttg agaatttcga gggatgatga   1380
gactgcgggg atggatttga cgaggcatgg tgggtttgct tatgcatacc atgatgatga   1440
agatggttca agcaggggag tagggttcat gctgcgtaga attgagcctg ctgctagtac   1500
cactccctct cccccccgctg caccacaagt ttaatcaaaa tgtggtttat gattttcaag   1560 cgtttttttag tttcgtacct gcacatagct atgggcaaag ctagccttgt caaaaccata   1620
tacaagcaag acacgaggga tgcatatatg aagtataaaa attaatgcgt gggggtcaac   1680
atttaggaaa tgtcttctag agttactgta cattttaaaa tgtttgttgg cttggtttat   1740 tatttcatc tttgaattcc aagactagtt tggtcgactg ttgtcacgtt agtttgtatc    1800
ctgctgcaga ataacttgct tgtaattgta tactgattag ttggtatata gtgatatatt   1860
atatatacta a                                                        1871

<210> SEQ ID NO 72
<211> LENGTH: 505
<212> TYPE: PRT
<213> ORGANISM: Glycine max

<400> SEQUENCE: 72

Met Ala Ser Leu Ser Cys Ser Ala Asn Asp Leu Ala Pro Leu Phe Asn
  1               5                  10                  15

Asp Thr Ala Ala Ala Asn Tyr Leu Cys Ala Gln Phe Asp Ser Ile Ser
             20                  25                  30

Arg Lys Leu Ala Glu Thr Thr Tyr Ala Val Asp Asn Thr Tyr Leu Leu
         35                  40                  45

Phe Ser Ala Tyr Leu Val Phe Ala Met Gln Leu Gly Phe Ala Met Leu
     50                  55                  60

Cys Ala Gly Ser Val Arg Ala Lys Asn Thr Met Asn Ile Met Leu Thr
 65                  70                  75                  80

Asn Val Leu Asp Ala Ala Ala Gly Gly Leu Ser Tyr Tyr Leu Phe Gly
                 85                  90                  95

Phe Ala Phe Ala Phe Gly Gly Pro Ser Asn Gly Phe Ile Gly Arg His
            100                 105                 110

Phe Phe Gly Leu Arg Asp Tyr Pro Met Gly Ser Ser Pro Ser Gly Asp
        115                 120                 125

Tyr Ser Phe Phe Leu Tyr Gln Trp Ala Phe Ala Ile Ala Ala Ala Gly
    130                 135                 140
```

Ile Thr Ser Gly Ser Ile Ala Glu Arg Thr Gln Phe Val Ala Tyr Leu
145                 150                 155                 160

Ile Tyr Ser Ser Phe Leu Thr Gly Phe Val Tyr Pro Ile Val Ser His
            165                 170                 175

Trp Phe Trp Ser Asp Gly Trp Ala Ser Ala Thr Arg Ser His Gly
        180                 185                 190

Asn Val Leu Phe Gly Ser Gly Val Ile Asp Phe Ala Gly Ser Gly Val
        195                 200                 205

Val His Met Val Gly Gly Ile Ala Gly Leu Trp Gly Ala Leu Ile Glu
210                 215                 220

Gly Pro Arg Ile Gly Arg Phe Asp Arg Ser Gly Arg Ser Val Ala Leu
225                 230                 235                 240

Arg Gly His Ser Ala Ser Leu Val Val Leu Gly Thr Phe Leu Leu Trp
            245                 250                 255

Phe Gly Trp Tyr Gly Phe Asn Pro Gly Ser Phe Val Thr Ile Asp Lys
            260                 265                 270

Gly Tyr Glu Ser Gly Gly Tyr Tyr Gly Gln Trp Ser Ala Ile Gly Arg
        275                 280                 285

Thr Ala Val Thr Thr Leu Ala Gly Ser Thr Ala Ala Leu Thr Thr
290                 295                 300

Leu Phe Ser Lys Arg Leu Leu Val Gly His Trp Asn Val Ile Asp Val
305                 310                 315                 320

Cys Asn Gly Leu Leu Gly Gly Phe Ala Ala Ile Thr Ser Gly Cys Ala
            325                 330                 335

Val Val Glu Pro Trp Ala Ala Ile Val Cys Gly Phe Val Ala Ala Trp
            340                 345                 350

Val Leu Ile Gly Leu Asn Lys Leu Ala Ala Lys Val Glu Tyr Asp Asp
        355                 360                 365

Pro Leu Glu Ala Ala Gln Leu His Gly Gly Cys Gly Ala Trp Gly Val
        370                 375                 380

Phe Phe Thr Gly Leu Phe Ala Lys Lys Val Tyr Val Glu Glu Ile Tyr
385                 390                 395                 400

Gly Val Gly Arg Pro Phe Gly Ala Leu Met Gly Gly Gly Gly Arg Leu
            405                 410                 415

Leu Ala Ala Gln Val Ile Gln Ile Leu Val Val Cys Gly Trp Val Thr
        420                 425                 430

Ala Thr Met Ala Pro Leu Phe Tyr Gly Leu His Lys Met Lys Leu Leu
        435                 440                 445

Arg Ile Ser Arg Asp Asp Glu Thr Ala Gly Met Asp Leu Thr Arg His
450                 455                 460

Gly Gly Phe Ala Tyr Ala Tyr His Asp Asp Glu Asp Gly Ser Ser Arg
465                 470                 475                 480

Gly Val Gly Phe Met Leu Arg Arg Ile Glu Pro Ala Ala Ser Thr Thr
            485                 490                 495

Pro Ser Pro Pro Ala Ala Pro Gln Val
                500                 505

<210> SEQ ID NO 73
<211> LENGTH: 1053
<212> TYPE: DNA
<213> ORGANISM: Glycine max

<400> SEQUENCE: 73
tttcacacac atgctgtggc tggccttttg ggtggtctcc tcacaggtct attagcagaa      60
ccagcccttt gtagactact attgccagtt accaactcaa ggggtgcatt ctatggtggt     120

| | |
|---|---|
| ggtggtggta tgcagttctt caagcaattg gtggcggcca tgtttgtcat tggatggaac | 180 |
| ttggtgtcca ccaccatcat tctccttgtc ataaaattgt tcatacccct gaggatgccg | 240 |
| gatgagcagc tggaaatcgg cgacgacgcc gtccacggcg aggaagctta tgccctctgg | 300 |
| ggtgatggag aaaaatatga cccaactagg catggttcct gcaaagtgg caacactttt | 360 |
| gtgtcacctt atgttaatgg tgcaagaggg gtgaccataa acttatgagt caagaaattc | 420 |
| ggctgtgctt tgctcacaca tatgtataaa gttatgtgat gaatccgtga gtggtgtaag | 480 |
| tagaaatttg attttgtcat gaaagaaaat tcaagttttg agatctgatg ttcctctggc | 540 |
| catccagcat tcgaagacct gatcatatat ttctggcaca gattgtgttg acatgtttat | 600 |
| aaaatttaga tttgtcaatt tttgaaggag cttgtgatta gttttctttt ccacttatat | 660 |
| gttttaatta ctagaagaat atcaaatttt cttttacga aatgcttagt acataattgt | 720 |
| taaaaaaaat catcatgtaa tgggtacgaa atatttatca attctatgaa tgagtatttt | 780 |
| tttcttagat aacttcagtg accactttta gaaaatttat cctatgtata aatttaaaa | 840 |
| gaatggtttt aactccaaaa ttttcaccta gtccttgtca aacaaatttt attttggctc | 900 |
| acttaaaggt aaaattattt agttatgcat ttcagaatga agtttggttc gaaatatttt | 960 |
| gacagtgtgt caaatataaa ttcttcaaaa gaaaaagcca agactacttt acaacaaaat | 1020 |
| agataagttt ctcataaact gagcacaagt ttt | 1053 |

<210> SEQ ID NO 74
<211> LENGTH: 135
<212> TYPE: PRT
<213> ORGANISM: Glycine max

<400> SEQUENCE: 74

Phe His Thr His Ala Val Ala Gly Leu Leu Gly Gly Leu Leu Thr Gly
 1               5                  10                  15

Leu Leu Ala Glu Pro Ala Leu Cys Arg Leu Leu Leu Pro Val Thr Asn
            20                  25                  30

Ser Arg Gly Ala Phe Tyr Gly Gly Gly Gly Met Gln Phe Phe Lys
        35                  40                  45

Gln Leu Val Ala Ala Met Phe Val Ile Gly Trp Asn Leu Val Ser Thr
    50                  55                  60

Thr Ile Ile Leu Leu Val Ile Lys Leu Phe Ile Pro Leu Arg Met Pro
65                  70                  75                  80

Asp Glu Gln Leu Glu Ile Gly Asp Asp Ala Val His Gly Glu Glu Ala
                85                  90                  95

Tyr Ala Leu Trp Gly Asp Gly Glu Lys Tyr Asp Pro Thr Arg His Gly
            100                 105                 110

Ser Leu Gln Ser Gly Asn Thr Phe Val Ser Pro Tyr Val Asn Gly Ala
        115                 120                 125

Arg Gly Val Thr Ile Asn Leu
    130                 135

<210> SEQ ID NO 75
<211> LENGTH: 799
<212> TYPE: DNA
<213> ORGANISM: Glycine max

<400> SEQUENCE: 75

| | |
|---|---|
| gtgtgtggtt ttgtcgcttc agtgtttctg atagcgtgca acaaattagc agagaaggtt | 60 |
| aagttcgatg atcctttgga agcggcgcag ttacacggtg ggtgtggcgc gtgggggtg | 120 |

-continued

```
atattcacgg cgctgttcgc gaaaaaggag tatgtgagcc aggtttatgg ggaggggagg      180
gcgcacgggt tgttcatgag gggtggaggg aagttgctgg cggcgcacgt gattcagatt      240
ttggttattg ttgggtgggt gagtgcgacc atgggaccct tgttttgggg gttgaataaa      300
ttgaaattgt tgaggatttc ttccgaggat gagcttgcgg ggatggatct tacccgtcat      360
ggaggatttg cttatgctta tgaggatgat gagtcgcaca agcatgggat tcagctgagg      420
aaggttgggc ccaacgcgtc gtccacaccc accactgatg aatgattacg atcacgatta      480
attcggcccc gacagtatta tcttcaattg aaattacgtg tgacttagaa aagaaaaaa      540 agatgatgat gattttgttt gtaatttatt ttatttgttt tgggtttttt ttttaattt      600 gtagattttt cttttatga tgggtaagta gggattttaa tttgtaattg ttattggccg      660
tatattggta gatgctggaa attgaagatt ctgctggaag atgcgaacgt ttctgaaaat      720
gatagatggc tgtggaaaat gaaatatttt tatttgtggg atttaatttt cgtagttttc      780
gccaaaaaag aaggaagag                                                  799
```

<210> SEQ ID NO 76
<211> LENGTH: 154
<212> TYPE: PRT
<213> ORGANISM: Glycine max

<400> SEQUENCE: 76

```
Val Cys Gly Phe Val Ala Ser Val Phe Leu Ile Ala Cys Asn Lys Leu
 1               5                  10                  15

Ala Glu Lys Val Lys Phe Asp Asp Pro Leu Glu Ala Ala Gln Leu His
            20                  25                  30

Gly Gly Cys Gly Ala Trp Gly Val Ile Phe Thr Ala Leu Phe Ala Lys
        35                  40                  45

Lys Glu Tyr Val Ser Gln Val Tyr Gly Glu Gly Arg Ala His Gly Leu
    50                  55                  60

Phe Met Arg Gly Gly Lys Leu Leu Ala Ala His Val Ile Gln Ile
65                  70                  75                  80

Leu Val Ile Val Gly Trp Val Ser Ala Thr Met Gly Pro Leu Phe Trp
                85                  90                  95

Gly Leu Asn Lys Leu Lys Leu Leu Arg Ile Ser Ser Glu Asp Glu Leu
            100                 105                 110

Ala Gly Met Asp Leu Thr Arg His Gly Gly Phe Ala Tyr Ala Tyr Glu
        115                 120                 125

Asp Asp Glu Ser His Lys His Gly Ile Gln Leu Arg Lys Val Gly Pro
    130                 135                 140

Asn Ala Ser Ser Thr Pro Thr Thr Asp Glu
145                 150
```

<210> SEQ ID NO 77
<211> LENGTH: 90
<212> TYPE: DNA
<213> ORGANISM: Glycine max

<400> SEQUENCE: 77

```
tttctctacc aatggggggt tattgactat tctggcggct atgtcatcca cctttcttct      60
ggaatcgctg gtttaactgc tgcttactgg                                       90
```

<210> SEQ ID NO 78
<211> LENGTH: 30
<212> TYPE: PRT
<213> ORGANISM: Glycine max

-continued

<400> SEQUENCE: 78

Phe Leu Tyr Gln Trp Gly Val Ile Asp Tyr Ser Gly Gly Tyr Val Ile
1               5                   10                  15

His Leu Ser Ser Gly Ile Ala Gly Leu Thr Ala Ala Tyr Trp
            20                  25                  30

<210> SEQ ID NO 79
<211> LENGTH: 459
<212> TYPE: DNA
<213> ORGANISM: Glycine max

<400> SEQUENCE: 79

```
caaattcgct ttacatacag tatggtaatt gtccaaattt ttacgaccga tttgtcaggt      60
acatcattta atgcatggca acatacatga taagatgaat caataaatac attccagctt     120
ccacgtacgt acgtctgcca acatagccgg cctcataatg tctcatccaa gtaaataaaa     180
cgacaaaatg attgattgta taaacctgct gcaaataact cagtatcata aagccttggc     240
cttgaacacc ctcactcgag ttttcagcca attaaccaaa tcacactgaa acactgaagt     300
actagttatt caactactag taataagcat aattaaatat agaggagccg aagacgaagc     360
aagcccagaa aggttgaaca aaggagacaa cgcatggcag ttaatggcag ccacagtggt     420
gggtatggtg attctctatg aagcctaga gtgaaaaag                              459
```

<210> SEQ ID NO 80
<211> LENGTH: 28
<212> TYPE: PRT
<213> ORGANISM: Glycine max

<400> SEQUENCE: 80

Pro Glu Arg Leu Asn Lys Gly Asp Asn Ala Trp Gln Leu Met Ala Ala
1               5                   10                  15

Thr Val Val Gly Met Val Ile Leu Tyr Gly Ser Leu
            20                  25

<210> SEQ ID NO 81
<211> LENGTH: 451
<212> TYPE: DNA
<213> ORGANISM: Glycine max

<400> SEQUENCE: 81

```
acttgtgcta cccatggcca ctcccacagc ataccaagaa cacctccctg catcccccca      60
ctggctaaac aaaggggaca acgcatggca gctgacagca gccactctcg taggtctcca     120
aagcatgccg ggtctggtga tcctctacgc cagcatggtg aagaagaaat gggccgtgaa     180
ctctgcattc atggccctct acgcctttgc agcagtccta atatgctggg tgctcgtttg     240
tcaccgaatg gccttcggtg acaaactcct tcccttctgg gggaagggcg ccccagcact     300
aggccagaag ttttaacac accgcgccaa agtccccgaa agcacgcact attataacaa     360
tggtacggtc gaaagcgcga cttcggaacc gttgtttgcc acggcttctc ttgtgtattt     420
tcaattcacg tttgcggcta tcacgcttat c                                    451
```

<210> SEQ ID NO 82
<211> LENGTH: 146
<212> TYPE: PRT
<213> ORGANISM: Glycine max

<400> SEQUENCE: 82

Met Ala Thr Pro Thr Ala Tyr Gln Glu His Leu Pro Ala Ser Pro His
1               5                   10                  15

```
Trp Leu Asn Lys Gly Asp Asn Ala Trp Gln Leu Thr Ala Ala Thr Leu
            20                  25                  30

Val Gly Leu Gln Ser Met Pro Gly Leu Val Ile Leu Tyr Ala Ser Met
            35                  40                  45

Val Lys Lys Lys Trp Ala Val Asn Ser Ala Phe Met Ala Leu Tyr Ala
    50                  55                  60

Phe Ala Ala Val Leu Ile Cys Trp Val Leu Val Cys His Arg Met Ala
65                      70                  75                  80

Phe Gly Asp Lys Leu Leu Pro Phe Trp Gly Lys Gly Ala Pro Ala Leu
                85                  90                  95

Gly Gln Lys Phe Leu Thr His Arg Ala Lys Val Pro Glu Ser Thr His
                100                 105                 110

Tyr Tyr Asn Asn Gly Thr Val Glu Ser Ala Thr Ser Glu Pro Leu Phe
            115                 120                 125

Ala Thr Ala Ser Leu Val Tyr Phe Gln Phe Thr Phe Ala Ala Ile Thr
    130                 135                 140

Leu Ile
145
```